United States Patent
Olson et al.

(10) Patent No.: US 11,919,925 B2
(45) Date of Patent: Mar. 5, 2024

(54) VIRUS FILTRATION

(71) Applicant: Alexion Pharmaceuticals, Inc., Boston, MA (US)

(72) Inventors: Bianca Olson, Watertown, CT (US); Saravanamoorthy Rajendran, Middletown, CT (US); Ryan Tedstone, New Haven, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 17/724,958

(22) Filed: Apr. 20, 2022

(65) Prior Publication Data

US 2022/0332755 A1 Oct. 20, 2022

Related U.S. Application Data

(63) Continuation of application No. 15/558,932, filed as application No. PCT/US2016/023746 on Mar. 23, 2016, now abandoned.

(Continued)

(51) Int. Cl.

| | |
|---|---|
| *A61K 39/395* | (2006.01) |
| *B01D 61/58* | (2006.01) |
| *B01D 69/08* | (2006.01) |
| *B01D 71/10* | (2006.01) |
| *B01D 71/34* | (2006.01) |
| *B01D 71/56* | (2006.01) |
| *B01D 71/68* | (2006.01) |
| *C07K 1/34* | (2006.01) |

(Continued)

(52) U.S. Cl.
CPC ............. *C07K 1/34* (2013.01); *B01D 61/58* (2013.01); *B01D 69/08* (2013.01); *B01D 71/10* (2013.01); *B01D 71/34* (2013.01); *B01D 71/56* (2013.01); *B01D 71/68* (2013.01); *C07K 16/065* (2013.01); *C07K 16/18* (2013.01); *B01D 2311/04* (2013.01); *B01D 2311/18* (2013.01); *C07K 2317/24* (2013.01)

(58) Field of Classification Search
None
See application file for complete search history.

(56) References Cited

U.S. PATENT DOCUMENTS

| | | |
|---|---|---|
| 9,079,949 B1 | 7/2015 | Andrien, Jr. et al. |
| 9,107,861 B1 | 8/2015 | Andrien, Jr. et al. |

(Continued)

FOREIGN PATENT DOCUMENTS

| | | |
|---|---|---|
| EP | 2527429 A2 | 11/2012 |
| EP | 2725033 A1 | 4/2014 |

(Continued)

OTHER PUBLICATIONS

Hongo-Hirasaki et al., "Effect of antibody solution conditions on filter performance for virus removal filter PlanovaTM 20N," Biotechnology progress, Jul. 2010, 26(4):1080-7.

(Continued)

*Primary Examiner* — M Franco G Salvoza
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are methods of performing viral filtration on a fluid including a recombinant antibody, and the use of these methods in methods of manufacturing or producing the recombinant antibody.

13 Claims, 28 Drawing Sheets
Specification includes a Sequence Listing.

Related U.S. Application Data

(60) Provisional application No. 62/137,187, filed on Mar. 23, 2015.

(51) Int. Cl.
  C07K 16/06  (2006.01)
  C07K 16/18  (2006.01)

(56) References Cited

U.S. PATENT DOCUMENTS

| | | | |
|---|---|---|---|
| 9,206,251 | B2 | 12/2015 | Andrien, Jr. et al. |
| 9,371,377 | B2 | 6/2016 | Andrien, Jr. et al. |
| 9,663,574 | B2 | 5/2017 | Andrien, Jr. et al. |
| 9,718,880 | B2 | 8/2017 | Bell et al. |
| 9,725,504 | B2 | 8/2017 | Bell et al. |
| 9,732,149 | B2 | 8/2017 | Bell et al. |
| 9,803,007 | B1 | 10/2017 | Andrien, Jr. et al. |
| 10,227,400 | B2 | 3/2019 | Andrien, Jr. et al. |
| 10,584,164 | B2 | 3/2020 | Andrien, Jr. et al. |
| 10,590,189 | B2 | 3/2020 | Bell et al. |
| 10,703,809 | B1 | 7/2020 | Bell et al. |
| 2007/0071675 | A1 | 3/2007 | Wu et al. |
| 2011/0034674 | A1 | 2/2011 | Mehta |
| 2012/0077963 | A1 | 3/2012 | Hongo et al. |
| 2012/0237515 | A1 | 9/2012 | Bell et al. |
| 2012/0282654 | A1 | 11/2012 | Yao et al. |
| 2013/0344535 | A1 | 12/2013 | Mundt et al. |
| 2014/0072585 | A1 | 3/2014 | Herigstad et al. |
| 2014/0116941 | A1 | 5/2014 | Thorm et al. |
| 2015/0299305 | A1 | 10/2015 | Andrien, Jr. et al. |
| 2016/0108115 | A1 | 4/2016 | Andrien, Jr. et al. |
| 2016/0244516 | A1 | 8/2016 | Bell et al. |
| 2016/0251433 | A1 | 9/2016 | Andrien, Jr. et al. |
| 2016/0376355 | A1 | 12/2016 | Bell et al. |
| 2017/0015741 | A1 | 1/2017 | Bell et al. |
| 2017/0349652 | A1 | 12/2017 | Bell et al. |
| 2018/0009885 | A1 | 1/2018 | Andrien, Jr. et al. |
| 2018/0072769 | A1 | 3/2018 | Olson et al. |
| 2019/0263897 | A1 | 8/2019 | Andrien, Jr. et al. |
| 2020/0157200 | A1 | 5/2020 | Andrien, Jr. et al. |
| 2020/0199211 | A1 | 6/2020 | Bell et al. |

FOREIGN PATENT DOCUMENTS

| | | |
|---|---|---|
| JP | 2010-510963 A | 4/2010 |
| JP | 2012-244993 A | 12/2012 |
| JP | 2013-501075 A | 1/2013 |
| JP | 2014-517047 A | 7/2014 |
| JP | 2017512463 A | 5/2017 |
| WO | 2009017491 A1 | 2/2009 |
| WO | 2010/001659 A1 | 1/2010 |
| WO | 2010/109920 A1 | 9/2010 |
| WO | 2011/031397 A1 | 3/2011 |
| WO | 2012/135345 A1 | 10/2012 |
| WO | 2012/176876 A1 | 12/2012 |
| WO | 2013170977 A1 | 11/2013 |
| WO | 16/034726 A1 | 3/2016 |

OTHER PUBLICATIONS

International Preliminary Report on Patentability in International Application No. PCT/US2016/023746, dated Sep. 26, 2017, 7 pages.

International Search Report/Written Opinion dated Jun. 7, 2016 issued by the European Patent Office; 100 pages.

| Run Order | Pre-Filter | pH | mM L-Arginine | mM NaCL | Product Concentration (g/L) | Throughput at 50% Flow Decay (L/m2) | Throughput at 50% Flow Decay (g/m2) |
|---|---|---|---|---|---|---|---|
| 1 | 0.1 | 7.6 | 50 | 65 | 3.09 | 68 | 210.12 |
| 2 | 0.1 | 5.5 | 50 | 300 | 2.91 | 56 | 162.96 |
| 3 | 0.1 | 5.5 | 0 | 300 | 3.37 | 20.8 | 70.096 |
| 4 | 0.1 | 5.5 | 0 | 65 | 3.54 | 18 | 63.72 |
| 5 | 0.1 | 7.6 | 0 | 300 | 3.36 | 9.5 | 31.92 |
| 6 | max | 5.5 | 50 | 65 | 3.06 | >283 | >866 |
| 7 | max | 5.5 | 0 | 65 | 3.54 | 229 | 810.66 |
| 8 | max | 5.5 | 0 | 300 | 3.37 | 300 | 1011 |
| 9 | max | 7.6 | 0 | 65 | 3.53 | 44.6 | 157.438 |
| 10 | 0.1 | 7.6 | 0 | 65 | 3.53 | 27.2 | 96.016 |
| 11 | 0.1 | 5.5 | 50 | 65 | 3.06 | 79 | 241.74 |
| 12 | 0.1 | 6.55 | 25 | 182.5 | 3.27 | 25 | 81.75 |
| 13 | max | 5.5 | 50 | 300 | 2.91 | >402 | >1172 |
| 14 | max | 7.6 | 0 | 300 | 3.36 | 63 | 211.68 |
| 15 | max | 7.6 | 50 | 65 | 3.09 | >291 | >899 |
| 16 | max | 7.6 | 50 | 300 | 2.92 | >298 | >870 |
| 17 | 0.1 | 7.6 | 50 | 300 | 2.92 | 64 | 186.88 |
| 21 | max | 7.6 | 25 | 65 | 3.34 | 254 | 848.36 |

FIG. 2

| Sorted Parameter Estimates | |
|---|---|
| Term | Prob>\|t\| |
| Pre-Filter[0.1] | 0.0003* |
| Pre-Filter[0.1]*(Hydrodynamic Radius - 5.91667) | 0.0064* |
| (pH-6.60833)*(Stabilizer-25) | 0.0086* |
| Hydrodynamic Radius | 0.0089* |
| (Stabilizer-25)*(Hydrodynamic Radius-5.91667) | 0.0092* |
| pH | 0.0094* |
| (mM NaCL-175.972)*(% Aggregate-0.73333) | 0.0099* |
| mM NaCL | 0.0103* |
| Pre-Filter[0.1]*(Stabilizer-25) | 0.0161* |
| % Aggregate | 0.0199* |
| (Stabilizer-25)*(% Aggregate-0.73333) | 0.0472* |
| Pre-Filter[0.1]*(% Aggregate-0.73333) | 0.0515 |
| (pH-6.60833)*(Hydrodynamic Radius-5.91667) | 0.2303 |
| Stabilizer | 0.2629 |

SEQUENCE LISTING

```
<160> NUMBER OF SEQ ID NOS: 40

<210> SEQ ID NO 1
<211> LENGTH: 10
<212> TYPE: PRT
<213> ORGANISM: Artificial Sequence
<220> FEATURE:
<223> OTHER INFORMATION: BNJ441 Heavy chain CDR1

<400> SEQUENCE: 1

Gly His Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: BNJ441 Heavy chain CDR2

<400> SEQUENCE: 2

Glu Ile Leu Pro Gly Ser Gly His Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: BNJ441 Heavy chain CDR3

<400> SEQUENCE: 3

Tyr Phe Phe Gly Ser Ser Pro Asn Trp Tyr Phe Asp Val
1               5                   10

<210> SEQ ID NO 4
<211> LENGTH: 122
<212> TYPE: PRT
<213> ORGANISM: Artificial Sequence
```

-continued

<220> FEATURE:
<223> OTHER INFORMATION: BNJ441 Heavy chain variable region

<400> SEQUENCE: 4

```
Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120
```

<210> SEQ ID NO 5
<211> LENGTH: 448
<212> TYPE: PRT
<213> ORGANISM: Artificial Sequence
<220> FEATURE:
<223> OTHER INFORMATION: BNJ441 Heavy chain

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
```

```
                210                 215                 220
Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
                420                 425                 430

Leu His Ser His Tyr Thr Gln Lys Ser Leu Ser Leu Ser Leu Gly Lys
                435                 440                 445

<210> SEQ ID NO 6
<211> LENGTH: 11
<212> TYPE: PRT
<213> ORGANISM: Artificial Sequence
<220> FEATURE:
<223> OTHER INFORMATION: BNJ441 Light chain CDR1

<400> SEQUENCE: 6

Gly Ala Ser Glu Asn Ile Tyr Gly Ala Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: BNJ441 Light chain CDR2

<400> SEQUENCE: 7

Gly Ala Thr Asn Leu Ala Asp
1               5

<210> SEQ ID NO 8
<211> LENGTH: 9
<212> TYPE: PRT
<213> ORGANISM: Artificial Sequence
<220> FEATURE:
<223> OTHER INFORMATION: BNJ441 Light chain CDR3

<400> SEQUENCE: 8
```

```
Gln Asn Val Leu Asn Thr Pro Leu Thr
1               5
```

```
<210> SEQ ID NO 9
<211> LENGTH: 107
<212> TYPE: PRT
<213> ORGANISM: Artificial Sequence
<220> FEATURE:
<223> OTHER INFORMATION: BNJ441 Light chain variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105
```

```
<210> SEQ ID NO 10
<211> LENGTH: 214
<212> TYPE: PRT
<213> ORGANISM: Artificial Sequence
<220> FEATURE:
<223> OTHER INFORMATION: BNJ441 Light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180             185             190
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 11
<211> LENGTH: 10
<212> TYPE: PRT
<213> ORGANISM: Artificial Sequence
<220> FEATURE:
<223> OTHER INFORMATION: Eculizumab Heavy chain CDR1

<400> SEQUENCE: 11

```
Gly Tyr Ile Phe Ser Asn Tyr Trp Ile Gln
1               5                   10
```

<210> SEQ ID NO 12
<211> LENGTH: 17
<212> TYPE: PRT
<213> ORGANISM: Artificial Sequence
<220> FEATURE:
<223> OTHER INFORMATION: Eculizumab Heavy chain CDR2

<400> SEQUENCE: 12

```
Glu Ile Leu Pro Gly Ser Gly Ser Thr Glu Tyr Thr Glu Asn Phe Lys
1               5                   10                  15

Asp
```

<210> SEQ ID NO 13
<211> LENGTH: 13
<212> TYPE: PRT
<213> ORGANISM: Artificial Sequence
<220> FEATURE:
<223> OTHER INFORMATION: Eculizumab Heavy chain CDR3

<400> SEQUENCE: 13

```
Tyr Phe Phe Gly Ser Ser Pro Asn Trp Tyr Phe Asp Val
1               5                   10
```

<210> SEQ ID NO 14
<211> LENGTH: 122
<212> TYPE: PRT
<213> ORGANISM: Artificial Sequence
<220> FEATURE:
<223> OTHER INFORMATION: Eculizumab Heavy chain variable region

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110
```

Gly Gln Gly Thr Leu Val Thr Val Ser Ser
        115                 120

<210> SEQ ID NO 15
<211> LENGTH: 448
<212> TYPE: PRT
<213> ORGANISM: Artificial Sequence
<220> FEATURE:
<223> OTHER INFORMATION: Eculizumab Heavy chain

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 16
<211> LENGTH: 11
<212> TYPE: PRT
<213> ORGANISM: Artificial Sequence
<220> FEATURE:
<223> OTHER INFORMATION: Eculizumab Light chain CDR1

<400> SEQUENCE: 16

Gly Ala Ser Glu Asn Ile Tyr Gly Ala Leu Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Eculizumab  Light chain CDR2

<400> SEQUENCE: 17

Gly Ala Thr Asn Leu Ala Asp
1               5

<210> SEQ ID NO 18
<211> LENGTH: 9
<212> TYPE: PRT
<213> ORGANISM: Artificial Sequence
<220> FEATURE:
<223> OTHER INFORMATION: Eculizumab Light chain CDR3

<400> SEQUENCE: 18

Gln Asn Val Leu Asn Thr Pro Leu Thr
1               5

<210> SEQ ID NO 19
<211> LENGTH: 107
<212> TYPE: PRT
<213> ORGANISM: Artificial Sequence
<220> FEATURE:
<223> OTHER INFORMATION: Eculizumab Light chain variable region

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Asn Thr Pro Leu
                 85                  90                  95

Thr Phe Gly Gln Gly Thr Lys Val Glu Ile Lys
            100                 105
```

<210> SEQ ID NO 20
<211> LENGTH: 214
<212> TYPE: PRT
<213> ORGANISM: Artificial Sequence
<220> FEATURE:
<223> OTHER INFORMATION: Eculizumab Light chain

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Gly Ala Ser Glu Asn Ile Tyr Gly Ala
                 20                  25                  30

Leu Asn Trp Tyr Gln Gln Lys Pro Gly Lys Ala Pro Lys Leu Leu Ile
             35                  40                  45

Tyr Gly Ala Thr Asn Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asn Val Leu Asn Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210
```

<210> SEQ ID NO 21
<211> LENGTH: 5
<212> TYPE: PRT
<213> ORGANISM: Artificial Sequence
<220> FEATURE:
<223> OTHER INFORMATION: BNJ383 Heavy chain CDR1

<400> SEQUENCE: 21

```
Asp Tyr Ser Met Asp
 1               5
```

<210> SEQ ID NO 22
<211> LENGTH: 17
<212> TYPE: PRT

<213> ORGANISM: Artificial Sequence
<220> FEATURE:
<223> OTHER INFORMATION: BNJ383 Heavy chain CDR2

<400> SEQUENCE: 22

Ala Ile His Leu Asn Thr Gly Tyr Thr Asn Tyr Asn Gln Lys Phe Lys
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: BNJ383 Heavy chain CDR3

<400> SEQUENCE: 23

Gly Phe Tyr Asp Gly Tyr Ser Pro Met Asp Tyr
1               5                   10

<210> SEQ ID NO 24
<211> LENGTH: 120
<212> TYPE: PRT
<213> ORGANISM: Artificial Sequence
<220> FEATURE:
<223> OTHER INFORMATION: BNJ383 Heavy chain variable region

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Pro Gly Gln Gly Leu Glu Trp Met
            35                  40                  45

Gly Ala Ile His Leu Asn Thr Gly Tyr Thr Asn Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
                100                 105                 110

Gly Thr Thr Val Thr Val Ser Ser
            115                 120

<210> SEQ ID NO 25
<211> LENGTH: 446
<212> TYPE: PRT
<213> ORGANISM: Artificial Sequence
<220> FEATURE:
<223> OTHER INFORMATION: BNJ383 Heavy chain

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Pro Gly Gln Gly Leu Glu Trp Met
            35                  40                  45

Gly Ala Ile His Leu Asn Thr Gly Tyr Thr Asn Tyr Asn Gln Lys Phe
        50                  55                  60

```
Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 26
<211> LENGTH: 15
<212> TYPE: PRT
<213> ORGANISM: Artificial Sequence
<220> FEATURE:
```

```
<223> OTHER INFORMATION: BNJ383 Light chain CDR1

<400> SEQUENCE: 26

Arg Ala Ser Glu Ser Val Asp Ser Tyr Gly Asn Ser Phe Met His
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: BNJ383 Light chain CDR2

<400> SEQUENCE: 27

Arg Ala Ser Asn Leu Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: BNJ383 Light chain CDR3

<400> SEQUENCE: 28

Gln Gln Ser Asn Glu Asp Pro Tyr Thr
1               5

<210> SEQ ID NO 29
<211> LENGTH: 112
<212> TYPE: PRT
<213> ORGANISM: Artificial Sequence
<220> FEATURE:
<223> OTHER INFORMATION: BNJ383 Light chain variable region

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
                20                  25                  30

Gly Asn Ser Phe Met His Trp Tyr Gln Gln Lys Pro Gly Lys Ala Pro
            35                  40                  45

Lys Leu Leu Ile Tyr Arg Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

<210> SEQ ID NO 30
<211> LENGTH: 218
<212> TYPE: PRT
<213> ORGANISM: Artificial Sequence
<220> FEATURE:
<223> OTHER INFORMATION: BNJ383 Light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
                20                  25                  30
```

```
Gly Asn Ser Phe Met His Trp Tyr Gln Gln Lys Pro Gly Lys Ala Pro
            35                  40                  45

Lys Leu Leu Ile Tyr Arg Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Tyr Thr Phe Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 31
<211> LENGTH: 9
<212> TYPE: PRT
<213> ORGANISM: Artificial Sequence
<220> FEATURE:
<223> OTHER INFORMATION: Samalizumab Heavy chain CDR1

<400> SEQUENCE: 31

Tyr Ser Phe Thr Asp Tyr Ile Ile Leu
1               5

<210> SEQ ID NO 32
<211> LENGTH: 17
<212> TYPE: PRT
<213> ORGANISM: Artificial Sequence
<220> FEATURE:
<223> OTHER INFORMATION: Samalizumab Heavy chain CDR2

<400> SEQUENCE: 32

His Ile Asp Pro Tyr Tyr Gly Ser Ser Asn Tyr Asn Leu Lys Phe Lys
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: Samalizumab Heavy chain CDR3

<400> SEQUENCE: 33

Ser Lys Arg Asp Tyr Phe Asp Tyr
1               5
```

```
<210> SEQ ID NO 34
<211> LENGTH: 117
<212> TYPE: PRT
<213> ORGANISM: Artificial Sequence
<220> FEATURE:
<223> OTHER INFORMATION: Samalizumab Heavy chain variable domain

<400> SEQUENCE: 34

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Asp Tyr
                20                  25                  30

Ile Ile Leu Trp Val Arg Gln Asn Pro Gly Lys Gly Leu Glu Trp Ile
            35                  40                  45

Gly His Ile Asp Pro Tyr Tyr Gly Ser Ser Asn Tyr Asn Leu Lys Phe
        50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
                100                 105                 110

Leu Thr Val Ser Ser
        115

<210> SEQ ID NO 35
<211> LENGTH: 443
<212> TYPE: PRT
<213> ORGANISM: Artificial Sequence
<220> FEATURE:
<223> OTHER INFORMATION: Samalizumab Heavy chain

<400> SEQUENCE: 35

Gln Val Gln Leu Gln Gln Ser Gly Ser Glu Leu Lys Lys Pro Gly Ala
1               5                   10                  15

Ser Val Lys Ile Ser Cys Lys Ala Ser Gly Tyr Ser Phe Thr Asp Tyr
                20                  25                  30

Ile Ile Leu Trp Val Arg Gln Asn Pro Gly Lys Gly Leu Glu Trp Ile
            35                  40                  45

Gly His Ile Asp Pro Tyr Tyr Gly Ser Ser Asn Tyr Asn Leu Lys Phe
        50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
                100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190
```

```
Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 36
<211> LENGTH: 11
<212> TYPE: PRT
<213> ORGANISM: Artificial Sequence
<220> FEATURE:
<223> OTHER INFORMATION: Samalizumab Light chain CDR1

<400> SEQUENCE: 36

Lys Ala Ser Gln Asp Ile Asn Ser Tyr Leu Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Samalizumab Light chain CDR2

<400> SEQUENCE: 37

Arg Ala Asn Arg Leu Val Asp
1               5

<210> SEQ ID NO 38
<211> LENGTH: 9
<212> TYPE: PRT
<213> ORGANISM: Artificial Sequence
```

```
<220> FEATURE:
<223> OTHER INFORMATION: Samalizumab Light chain CDR3

<400> SEQUENCE: 38

Leu Gln Tyr Asp Glu Phe Pro Tyr Thr
1               5

<210> SEQ ID NO 39
<211> LENGTH: 107
<212> TYPE: PRT
<213> ORGANISM: Artificial Sequence
<220> FEATURE:
<223> OTHER INFORMATION: Samalizumab Light chain variable region

<400> SEQUENCE: 39

Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 40
<211> LENGTH: 214
<212> TYPE: PRT
<213> ORGANISM: Artificial Sequence
<220> FEATURE:
<223> OTHER INFORMATION: Samalizumab Light chain

<400> SEQUENCE: 40

Asp Ile Gln Met Thr Gln Ser Pro Ser Ser Leu Ser Ala Ser Ile Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

VIRUS FILTRATION

CROSS REFERENCE TO RELATED APPLICATIONS

This application is a continuation of U.S. patent application Ser. No. 15/558,932, filed on Feb. 12, 2018, which is a 35 U.S.C. 371 national stage filing of International Application No. PCT/US2016/023746, filed on Mar. 23, 2016, which claims priority to and the benefit of U.S. Provisional Patent Application No. 62/137,187, filed on Mar. 23, 2015. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 20, 2022, is named AXJ-293US-CN_Sequence_Listing.txt and is 36,419 bytes in size.

TECHNICAL FIELD

This invention relates generally to methods of purifying recombinant proteins and methods of manufacturing recombinant protein products.

BACKGROUND

Recombinant proteins, such as monoclonal antibodies (mAb), are an important and valuable class of therapeutic products for the treatment of diseases, such as paroxysmal nocturnal hemoglobinuria (PNH) and atypical hemolytic uremic syndrome (aHUS). Mammalian cells including a nucleic acid that encodes a recombinant protein are often used to produce the recombinant protein. The recombinant protein is then purified from the mammalian cell culture using a process that can include the passage of a fluid including the recombinant protein through a virus filter. These purification processes often experience slow flow rates and/or become fouled due to the plugging of a virus filter in the process. The slow flow rate and/or fouling of a virus filter in a purification process can result in recombinant protein loss, can negatively impact the safety of the resulting recombinant protein product, and/or reduce the efficiency of the purification process.

SUMMARY

The present disclosure is based, at least in part, on the discovery that a method of performing viral filtration that includes one or more steps of (e.g., two, three, or four) pre-filtering a fluid including a recombinant antibody (e.g., using a Sartorius Virosart® Max pre-filter), adjusting the pH of a fluid including a recombinant antibody, adding a stabilizing agent to a fluid including a recombinant antibody, and adjusting the sodium chloride concentration in a fluid including a recombinant antibody, prior to flowing the fluid through a virus filter, has a substantially improved throughput compared to methods of performing viral filtration that do not include these one or more steps, prior to flowing the fluid through a virus filter. In view of this discovery, provided herein are methods of performing viral filtration that include one or more (e.g., two, three, or four) steps of pre-filtering a fluid including a recombinant antibody, adjusting the pH of a fluid including a recombinant antibody, adding a stabilizing agent to a fluid including a recombinant antibody, and adjusting the sodium chloride concentration in a fluid including a recombinant antibody, prior to flowing the fluid through a virus filter, and methods of manufacturing or purifying a recombinant antibody that include any of the viral filtration methods described herein. Any of the viral filtration methods can be performed as a large scale process or as part of a large scale process.

Provided herein are methods of performing viral filtration that include: (a) adjusting (e.g., increasing or decreasing) the pH of a fluid including a recombinant antibody to between about 5.0 and about 6.7 (e.g., between about 5.0 and about 6.5, between about 5.0 and about 6.0, or between about 5.5 and about 6.0); and (b) flowing the fluid through a virus filter to produce a filtrate including the recombinant antibody. Some embodiments of any of the methods described herein further include, prior to (b): adding a stabilizing agent to the fluid in an amount sufficient to yield a final concentration of between about 0.1 mM and about 25 mM (e.g., between about 0.1 mM and about 24 mM, between about 0.1 mM and about 24 mM, between about 0.1 mM and about 22 mM, between about 0.1 mM and about 20 mM, between about 0.1 mM and about 10 mM, or between about 0.1 mM and about 5 mM) stabilizing agent in the fluid. Some embodiments of any of the methods described herein further include, immediately prior to (b): flowing the fluid through a pre-filter (e.g., a filter including a polyamide membrane or a depth filter (e.g., a depth filter including a porous filtration medium that is anionic and/or hydrophobic)). In some embodiments of any of the methods described herein, the fluid further includes between about 5 mM and about 300 mM (e.g., between about 50 mM and about 300 mM, about 100 mM and about 300 mM, or about 100 mM and about 250 mM) sodium chloride. In some embodiments of any of the methods described herein, prior to (a), the pH of the fluid is between about 7.4 and about 7.8 (e.g., between about 7.5 and about 7.7, or about 7.6).

Also provided are methods of performing viral filtration that include: (a) adding a stabilizing agent to a fluid including a recombinant antibody in an amount sufficient to yield a final concentration of between about 10 mM and about 100 mM (e.g., between about 10 mM and about 90 mM, between about 10 mM and about 80 mM, between about 10 mM and about 70 mM, between about 10 mM and about 60 mM, between about 10 mM and about 50 mM, between about 15 mM and about 50 mM, between about 20 mM and about 50 mM) stabilizing agent in the fluid, wherein prior to adding, the fluid has a pH of between about 6.7 and about 8.5 (e.g., between about 7.0 and about 7.8, between about 7.4 and about 7.8, or about 7.6); and (b) flowing the fluid through a virus filter to produce a filtrate including the recombinant antibody. Some embodiments of any of the methods described herein further include, immediately prior to (b): flowing the fluid through a pre-filter (e.g., a pre-filter including a polyamide membrane or a depth filter (e.g., a depth filter including a porous filtration medium that is anionic and/or hydrophobic). In some embodiments of any of the methods described herein the fluid includes between about 1 mM and about 100 mM (e.g., between about 1 mM and about 80 mM) sodium chloride. In some embodiments of any of the methods described herein, the stabilizing agent is selected from the group of: arginine (e.g., L-arginine or L-arginine HCl), alanine, aspartic acid, glutamic acid, leucine, lysine, histidine, glycine, sucrose, trehalose, mannitol, sorbitol, and Polysorbate 80.

In some embodiments of any of the methods described herein, the virus filter includes a polyethersulfone (PES)

membrane, a polyvinylidene fluoride (PVDF) membrane (e.g., a PVDF membrane that is a hollow fiber membrane), or cuprammonium-regenerated cellulose membrane (e.g., a cuprammonium-regenerated cellulose membrane that is a hollow fiber membrane).

In some embodiments of any of the methods described herein, prior to (a), the fluid includes between about 0.1 mg/mL and about 25 mg/mL (e.g., between about 0.1 mg/mL and about 15 mg/mL, between about 1 mg/mL and about 15 mg/mL, or between about 5 mg/mL and about 15 mg/mL) recombinant antibody. In some embodiments of any of the methods described herein, the fluid has a pH of between about 7.4 and about 7.8 (e.g., between about 7.5 and about 7.7, or about 7.6). In some embodiments of any of the methods described herein, the fluid includes between about 55 mM and about 90 mM (e.g., about 65 mM) sodium chloride.

In some embodiments of any of the methods described herein, the recombinant antibody includes one or both of: a heavy chain variable domain that includes a total of between one and six histidines in the set of CDR1, CDR2, and CDR3; and a light chain variable domain that includes a total of between one and six histidines in the set of CDR1, CDR2, and CDR3. In some embodiments of any one of the methods described herein, the recombinant antibody includes a heavy chain variable domain that includes a total of between one and five (e.g., between one and three, or two) histidines in the set of CDR1, CDR2, and CDR3. In some embodiments of any of the methods described herein, the CDR1 includes one histidine residue and the CDR2 includes one histidine residue. In some embodiments of any of the methods described herein, the CDR1 includes a sequence of SEQ ID NO: 1. In some embodiments of any of the methods described herein, the CDR2 includes a sequence of SEQ ID NO: 2. In some embodiments of any of the methods described herein, the CDR3 includes a sequence of SEQ ID NO: 3. In some embodiments of any of the methods described herein, the heavy chain variable domain includes a sequence of SEQ ID NO: 4. In some embodiments of any of the methods described herein, the recombinant antibody includes a heavy chain including a sequence of SEQ ID NO: 5. In some embodiments of any of the methods described herein, the recombinant antibody includes a light chain variable region including a CDR1 including a sequence of SEQ ID NO: 6, a CDR2 including a sequence of SEQ ID NO: 7, and a CDR3 including a sequence of SEQ ID NO: 8. In some embodiments of any of the methods described herein, the recombinant antibody includes a light chain variable region including a sequence of SEQ ID NO: 9. In some embodiments of any of the methods described herein, recombinant antibody includes a light chain including a sequence of SEQ ID NO: 10.

In any of the methods described herein, the recombinant antibody includes a heavy chain variable domain including a CDR1 including a sequence of SEQ ID NO: 11, a CDR2 including a sequence of SEQ ID NO: 12, and a CDR3 including a sequence of SEQ ID NO: 13. In any of the methods described herein, the heavy chain variable domain includes a sequence of SEQ ID NO: 14. In some embodiments of any of the methods described herein, the recombinant antibody includes a heavy chain including a sequence of SEQ ID NO: 15. In some embodiments of any of the methods described herein, the recombinant antibody includes a light chain variable domain including a CDR1 including a sequence of SEQ ID NO: 16, a CDR2 including a sequence of SEQ ID NO: 17, and a CDR3 including a sequence of SEQ ID NO: 18. In some embodiments of any of the methods described herein, the light chain variable domain includes a sequence of SEQ ID NO: 19. In some embodiments of any of the methods described herein, the recombinant antibody includes a light chain including a sequence of SEQ ID NO: 20.

In some embodiments of any of the methods described herein, the recombinant antibody specifically binds to human complement protein C5.

As used herein, the word "a" before a noun represents one or more of the particular noun. For example, the phrase "a stabilizing agent" represents "one or more stabilizing agents."

The term "mammalian cell" means any cell from or derived from any mammal (e.g., a human, a hamster, a mouse, a green monkey, a rat, a pig, a cow, or a rabbit). For example, a mammalian cell can be an immortalized cell. The mammalian cell can be a differentiated or undifferentiated cell. Non-limiting examples of mammalian cells are described herein. Additional examples of mammalian cells are known in the art.

The term "substantially free" means a composition (e.g., a filtrate) that is at least or about 90% free, such as at least or about 95%, 96%, 97%, 98%, or at least or about 99% free, or about 100% free of a specified substance, such as soluble antibody aggregates or host cell proteins.

The term "culturing" or "cell culturing" means maintenance or proliferation of a mammalian cell under a controlled set of physical conditions.

The term "culture of mammalian cells" means a culture medium (such as a liquid culture medium) including a plurality of mammalian cells that is maintained or proliferated under a controlled set of physical conditions.

The term "liquid culture medium" means a fluid that includes sufficient nutrients to allow a cell (such as a mammalian cell) to grow or proliferate in vitro. A liquid culture medium can include, for example, one or more of: amino acids (such as 20 amino acids), a purine (such as hypoxanthine), a pyrimidine (such as thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can include serum from a mammal. In some embodiments, a liquid culture medium does not include serum or another extract from a mammal (a defined liquid culture medium). A liquid culture medium can also include trace metals, a mammalian growth hormone, and/or a mammalian growth factor. An example of liquid culture medium is minimal medium (such as a medium including only inorganic salts, a carbon source, and water). Non-limiting examples of liquid culture medium are described herein. Additional examples of liquid culture medium are known in the art and are commercially available. A liquid culture medium can include any density of mammalian cells. For example, as used herein, a volume of liquid culture medium removed from a vessel (such as a bioreactor) can be substantially free of mammalian cells.

The term "antibody" means a polypeptide including an amino acid sequence of at least 10 amino acids (such as at least 15, 20, 30, 40, 50, 60, 70, 80, 90, or 100 amino acids) of an immunoglobulin protein (such as a variable domain sequence, a framework sequence, or a constant domain sequence of a heavy or light chain immunoglobulin). An antibody can be, e.g., an IgG, IgE, IgD, IgA, or IgM. The antibody may be any subclass of IgG, such as IgG1, IgG2, IgG3, or IgG4, or the chimeric IgG2/4 as found in eculizumab. The antibody may be an antigen-binding antibody fragment, such as a Fab fragment, a F(ab')$_2$ fragment, or an scFv fragment. The antibody may be a bi-specific antibody or a tri-specific antibody, or a dimer, trimer, or multimer antibody, or a diabody, an AFFIBODY®, or a NANO-BODY®. The antibody can be an engineered protein including at least one immunoglobulin domain (such as a fusion protein including a Fc domain). The antibody can be an engineered protein having four antibody binding domains such as DVD-Ig and CODV-Ig. See, e.g., US2007/0071675 and WO2012/135345. Non-limiting examples of antibodies are described herein and additional examples of antibodies are known in the art.

The term "capturing" means a step performed to partially purify or isolate (such as at least or about 10%, 15%, 20%, 25%, 30%, 40%, 45%, 50%, 55%, 60%, 65%, 70%, 75%, 80%, 85%, 90%, or 95%, or at least or about 99% pure by weight), concentrate, and/or stabilize a recombinant antibody from one or more other components present in a fluid including the recombinant antibody. Other components may include buffers, salts, DNA, RNA, host cell proteins, and aggregates of the desired recombinant antibody present in or secreted from a mammalian cell. Capturing can be performed using a chromatography resin that binds a recombinant antibody through the use of a specific recognition and binding interaction, such as with protein A chromatography or using antigen chromatography. Non-limiting methods for capturing a recombinant antibody from a fluid including the recombinant antibody or a clarified liquid culture medium are described herein and others are known in the art. A recombinant antibody can be captured from a liquid culture medium using at least one chromatography column (such as any of the chromatography columns described herein, such as a chromatography column packed with an affinity chromatography resin, an anionic exchange chromatography resin, a cationic exchange chromatography resin, a mixed-mode chromatography resin, a molecular sieve chromatography resin, or a hydrophobic interaction chromatography resin). Capturing can be performed using a chromatography resin that utilizes a protein A-binding capture mechanism, an antibody- or antibody fragment-binding capture mechanism, or an antigen-binding capture mechanism.

The term "purifying" means a method or step performed to isolate a recombinant antibody from one or more other impurities or components present in a fluid including a recombinant antibody. The components being separated include liquid culture medium proteins, host cell proteins, aggregates of the desired recombinant antibody, DNA, RNA, other proteins, endotoxins, and viruses present in or secreted from a mammalian cell. For example, a purifying step can be performed before or after an initial capturing step and/or before or after a step of flowing a recombinant antibody through a depth filter or a pre-filter and/or a virus filter. A purifying step can be performed using a resin, membrane, or any other solid support that binds either a recombinant antibody or contaminants (such as through the use of affinity chromatography, hydrophobic interaction chromatography, anion or cation exchange chromatography, mixed-mode chromatography resin, or molecular sieve chromatography). A recombinant antibody can be purified from a fluid including the recombinant antibody using at least one chromatography column and/or chromatographic membrane (such as any of the chromatography columns described herein).

The term "polishing" is a term of art and means a step performed to remove remaining trace or small amounts of contaminants or impurities from a fluid including a recombinant antibody that is close to a final desired purity. For example, polishing can be performed by passing a fluid including the recombinant antibody through a chromatographic column(s) or membrane absorber(s) that selectively binds to either the recombinant antibody or small amounts of remaining contaminants or impurities present in the fluid including the recombinant antibody. In such an example, the eluate/filtrate of the chromatographic column(s) or membrane absorber(s) includes the recombinant antibody. As described herein, one or more unit operations of polishing can be performed prior to flowing a fluid including the recombinant antibody through a virus filter.

The term "filtrate" is a term of art and means a fluid that is emitted from a filter (e.g., a depth filter, a pre-filter, or a virus filter) that includes a detectable amount of a recombinant antibody.

The term "filtering" means the removal of at least part of (such as at least 90%, 95%, 96%, 97%, 98%, or 99%) undesired biological contaminants (such as a mammalian cell, bacteria, yeast cells, viruses, mycobacteria, or mycoplasma), impurities (such as soluble antibody aggregates, host cell proteins, host cell DNA, and other chemicals used in a method for purifying a recombinant antibody or a method of manufacturing a recombinant antibody), and/or particulate matter (such as precipitated antibodies) from a fluid (such as a liquid culture medium or fluid present in any of the processes described herein).

The term "viral filtration" means the removal of at least part of (such as at least 90%, 95%, 96%, 97%, 98%, or 99%) viruses from a fluid (e.g., such as a liquid culture medium or fluid present in any of the processes described herein) that includes a recombinant antibody. Methods for performing viral filtration are described herein.

The term "virus filter" means a filter capable of removing at least part of (such as at least 90%, 95%, 96%, 97%, 98%, or 99%, or 100%) viruses from a fluid (e.g., such as a liquid culture medium or fluid present in any of the processes described herein) including a recombinant antibody when the fluid is flowed through the filter. Non-limiting examples of virus filters are described herein. Additional examples of virus filters are known in the art.

The term "pre-filter" is a filter capable of removing at least part of (such as at least 50%, 55%, 60%, 65%, 70%, 75%, 80%, 85%, 90%, 95%, 96%, 97%, 98%, or 99%, or 100%) soluble protein aggregates and/or particles from a fluid (e.g., such as a liquid culture medium or fluid present in any of the processes described herein) when the fluid is flowed through the pre-filter. A fluid can be, e.g., flowed through a pre-filter prior to flowing the fluid through a virus filter. Non-limiting examples of pre-filters are described herein. Additional examples of pre-filters are known in the art.

The term "secreted antibody" or "secreted recombinant antibody" means an antibody (such as a recombinant antibody) that originally included at least one secretion signal sequence when it is translated within a mammalian cell, and through, at least in part, enzymatic cleavage of the secretion signal sequence in the mammalian cell, is secreted at least partially into the extracellular space (such as a liquid culture medium). Skilled practitioners will appreciate that a "secreted" antibody need not dissociate entirely from the cell to be considered a secreted antibody.

The term "clarified liquid culture medium" means a liquid culture medium obtained from a mammalian, bacterial, or yeast cell culture that is substantially free (such as at least 90%, 92%, 94%, 96%, 98%, or 99% free) of mammalian, bacterial, or yeast cells. A clarified liquid culture medium can be prepared, for example, by filtering a cell culture (such as alternating tangential filtration or tangential flow filtration), by centrifuging a cell culture and collecting the supernatant, or by allowing the cells in the cell culture settle and obtaining a fluid that is substantially free of cells. The cells can also be separated from the medium by the use of a cell separation device, such as the ATF system from Refine Technology.

Purification or manufacture of recombinant antibodies usually requires in series performance of multiple independent purification operations or steps. The term "unit operation" is a term of art and means a discreet step or mini-process performed in a larger general process for purifying a recombinant antibody or a method of manufacturing a recombinant antibody (such as a method of manufacturing a recombinant antibody from a clarified liquid culture medium). For example, a unit of operation can be a step of capturing the recombinant antibody, ultrafiltration/diafiltration to concentrate the recombinant antibody in a fluid, ion exchange chromatography, hydrophobic interaction chromatography, polishing the recombinant antibody, viral inactivation, viral filtration, pre-filtration, adjustment of pH, adjustment of ionic strength, and adjustment of both pH and ionic strength of a fluid including the recombinant antibody.

The term "depth filter" is a term of art and means a filter that includes a porous filtration medium that captures contaminants and/or impurities (such as any of the contaminants and/or impurities described herein) within its 3-dimensional structure and not merely on the surface. Depth filters are characterized in that they retain the contaminants or impurities within the filter and can retain a relatively large quantity before becoming clogged. Depth filter construction may include multiple layers, multiple membranes, a single layer, or a resin material. Non-limiting examples of depth filters include CUNO® Zeta PLUS® Delipid filters (3M, St. Paul, MN), CUNO® Emphaze AEX filters (3M, St. Paul, MN), CUNO® 90ZA08A filters (3M, St. Paul, MN), CUNO® 90ZB08A filters (3M, St. Paul, MN), CUNO® DELI08A Delipid filters (3M, St. Paul, MN), CUNO® DELIP08A Delipid plus filters (3M, St. Paul, MN), Millipore XOHC filters (EMD Millipore, Billerica, MA), MIL-LISTAK® pads (EMD Millipore, Billerica, MA).

The term "soluble protein aggregates" is a term of art and means complexes of two or more proteins (such as recombinant antibodies) that are soluble in a fluid. Such complexes can form through hydrophobic and/or ionic interactions between individual recombinant protein molecules or fragments thereof.

The term "stabilizing agent" is an agent that reduces the hydrodynamic radius of a recombinant antibody in a fluid and/or minimizes the level of soluble and/or insoluble protein aggregates (e.g., soluble and/or insoluble recombinant antibody aggregates and/or soluble and/or insoluble host cell protein aggregates) in a fluid including a recombinant protein. Non-limiting examples of stabilizing agents are described herein. Additional examples of stabilizing agents are known in the art.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a table showing the throughput of a Virosart® CPV virus filter at the time point at which 50% flow decay was observed when a fluid including between 2.91 mg/mL to 3.54 mg/mL of BNJ441 human monoclonal antibody, between 65 mM to 300 mM sodium chloride, and 0 or 50 mM L-arginine, and having a pH of between 5.5 and 7.6 is passed through the filter. Each fluid passed through the Virosart® CPV virus filter had been pre-filtered using a 0.1 µm filter or a Sartorius Virosart® Max pre-filter.

Figure 8:
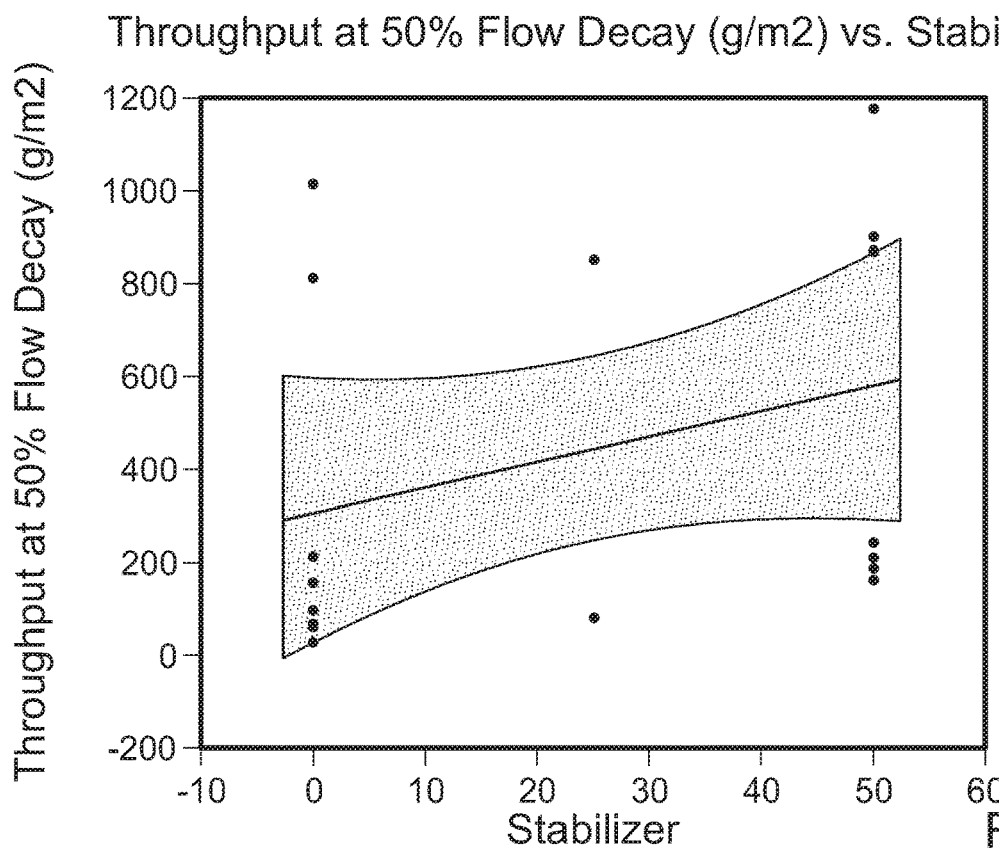

FIG. 8 is a graph showing the relationship of the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using a 0.1 μm filter or a Sartorius Virosart® Max pre-filter, to the amount of L-arginine present in each fluid.

Figure 9:
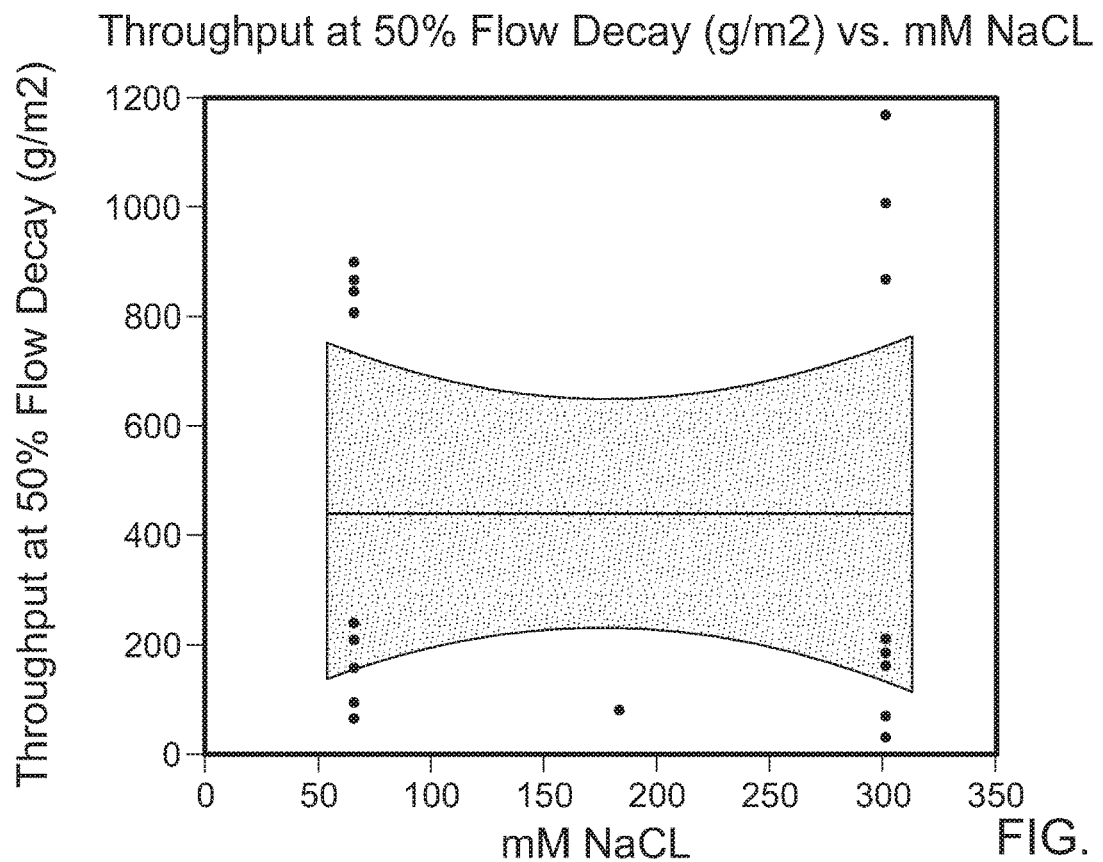

FIG. 9 is a graph showing the relationship of the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using a 0.1 μm filter or a Sartorius Virosart® Max pre-filter, to the concentration of sodium chloride present in each fluid.

Figure 10:
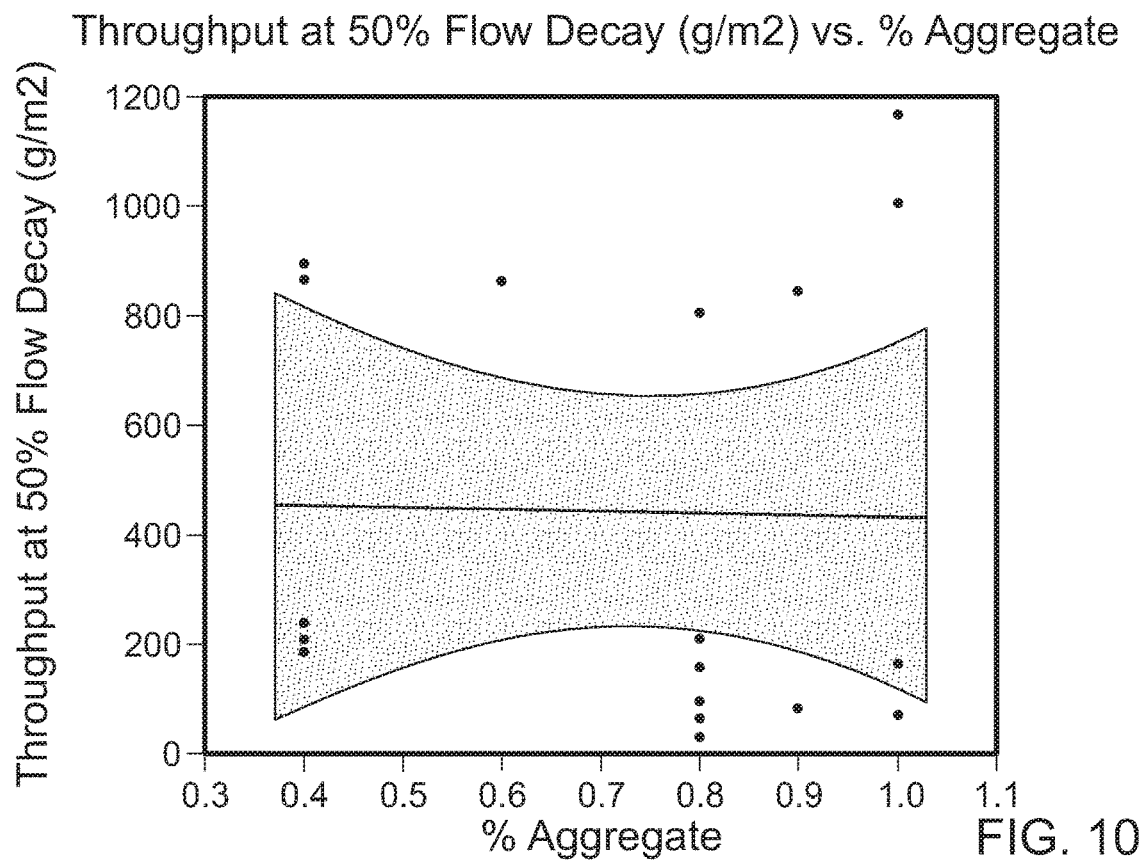

FIG. 10 is a graph showing the relationship of the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using 0.1 μm filter or a Sartorius Virosart® Max pre-filter, to the percentage of soluble protein aggregates present in each fluid.

Figure 11:
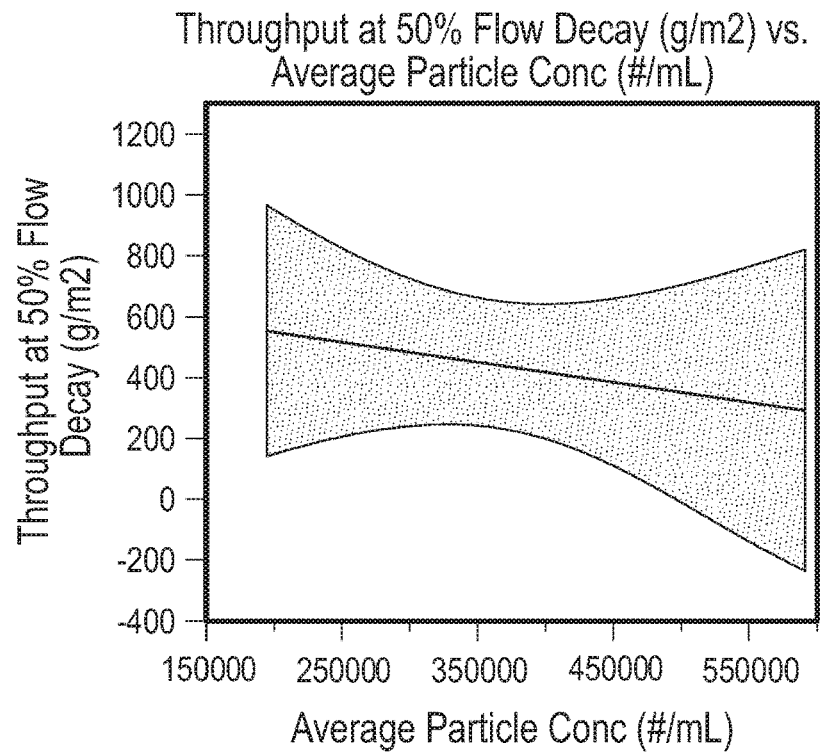

FIG. 11 is a graph showing the relationship of the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using 0.1 μm filter or a Sartorius Virosart® Max pre-filter, to the average particle concentration (number per mL of fluid).

Figure 12:
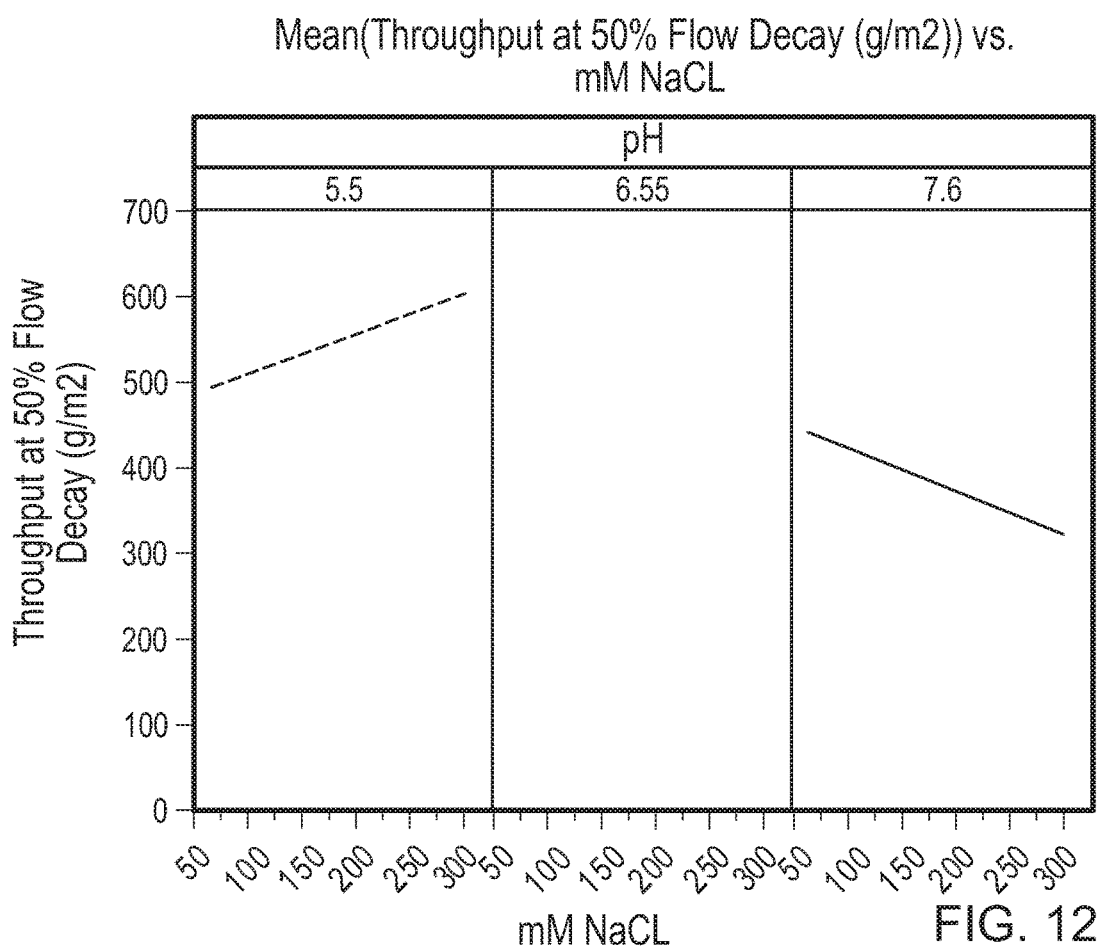

FIG. 12 is a graph showing the relationship between throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using 0.1 μm filter or a Sartorius Virosart® Max pre-filter; the concentration of sodium chloride in each fluid; and the pH of each fluid.

Figure 13:
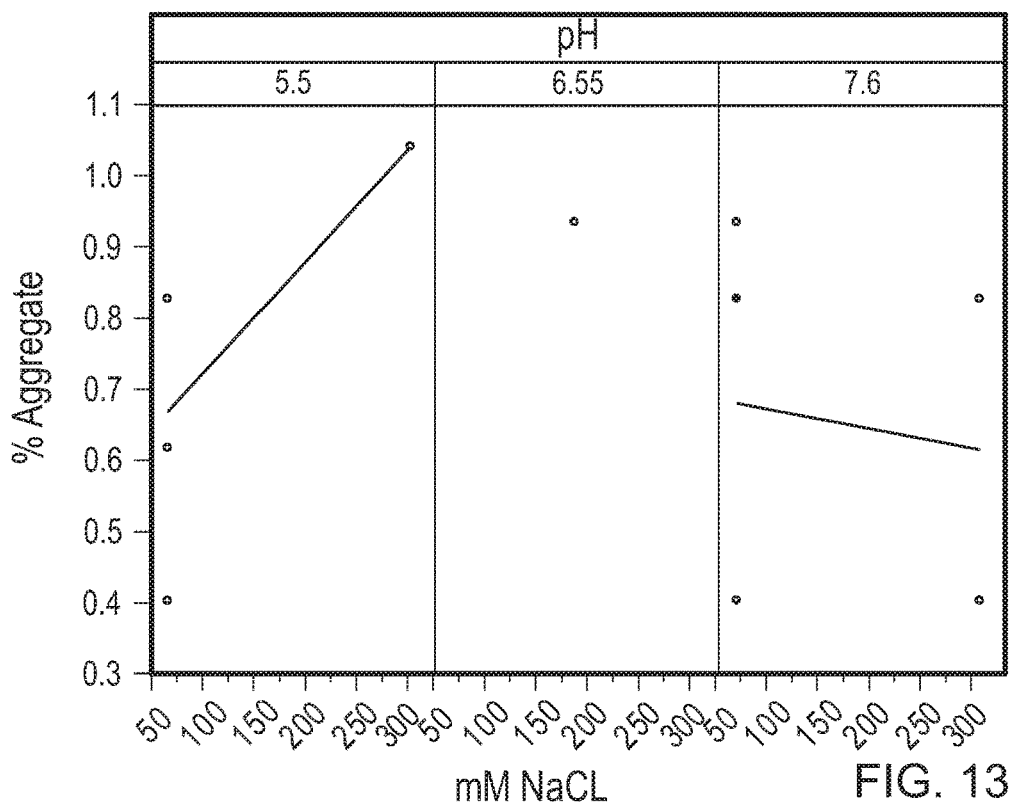

FIG. 13 is a graph showing the relationship between the percentage of soluble protein aggregates present in fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using 0.1 μm filter or a Virosart Sartorius® Max pre-filter; the concentration of sodium chloride in each fluid; and the pH of each fluid.

Figure 14:
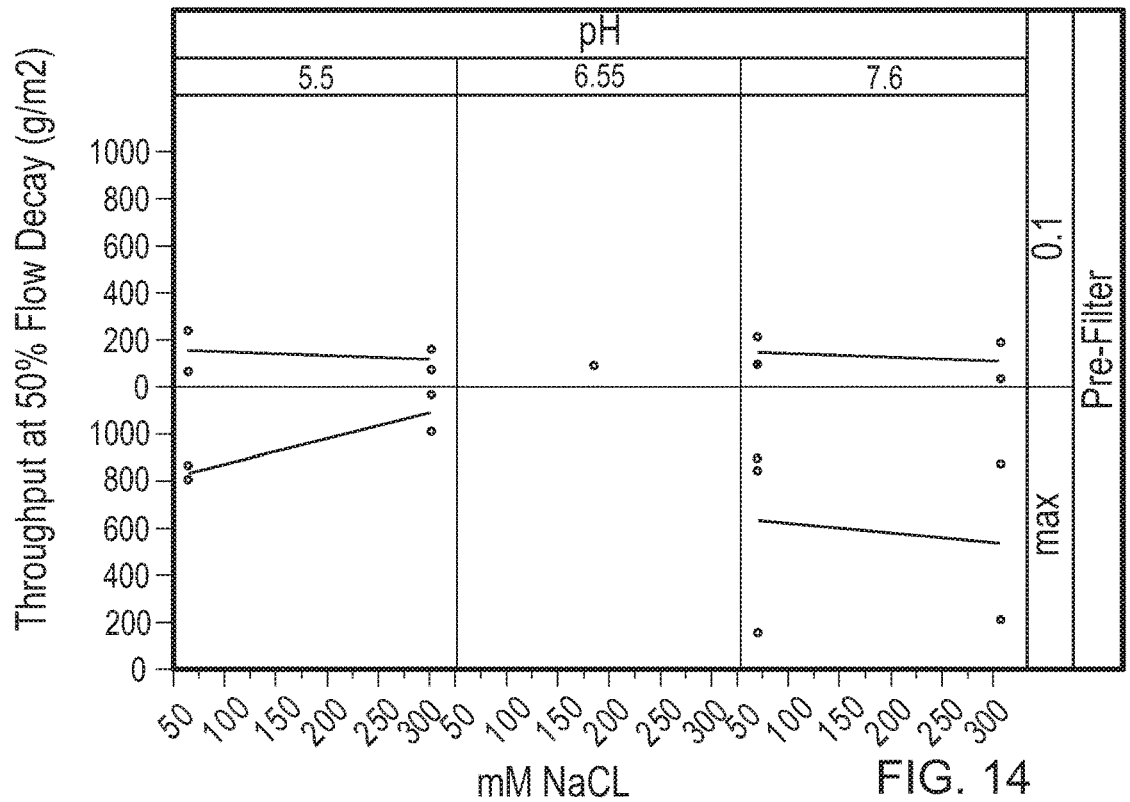

FIG. 14 is a graph showing the relationship between the throughput at 50% flow decay for a Virosart® CPV virus filter for fluids that had been pre-filtered using a 0.1 μm filter or a Sartorius Virosart® Max pre-filter, and including between 2.91 mg/mL to 3.54 mg/mL BNJ441 human monoclonal antibody, between 65 mM to 300 mM sodium chloride, and 0 or 50 mM L-arginine; the pH of each fluid; and the concentration of sodium chloride in each fluid.

Figure 15:
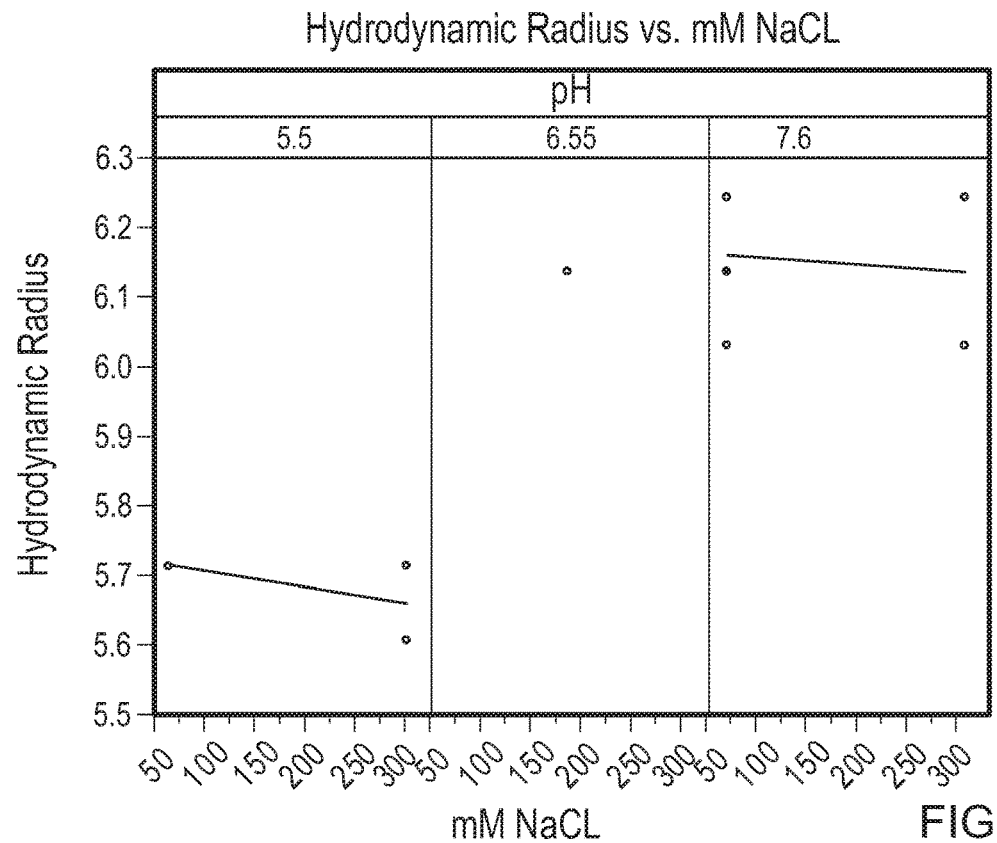

FIG. 15 is a graph showing the relationship between the hydrodynamic radius of BNJ441 human monoclonal antibody in fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either previously pre-filtered using 0.1 μm filter or a Sartorius Virosart® Max pre-filter; the pH of each fluid; and the sodium chloride concentration of each fluid.

Figure 16:
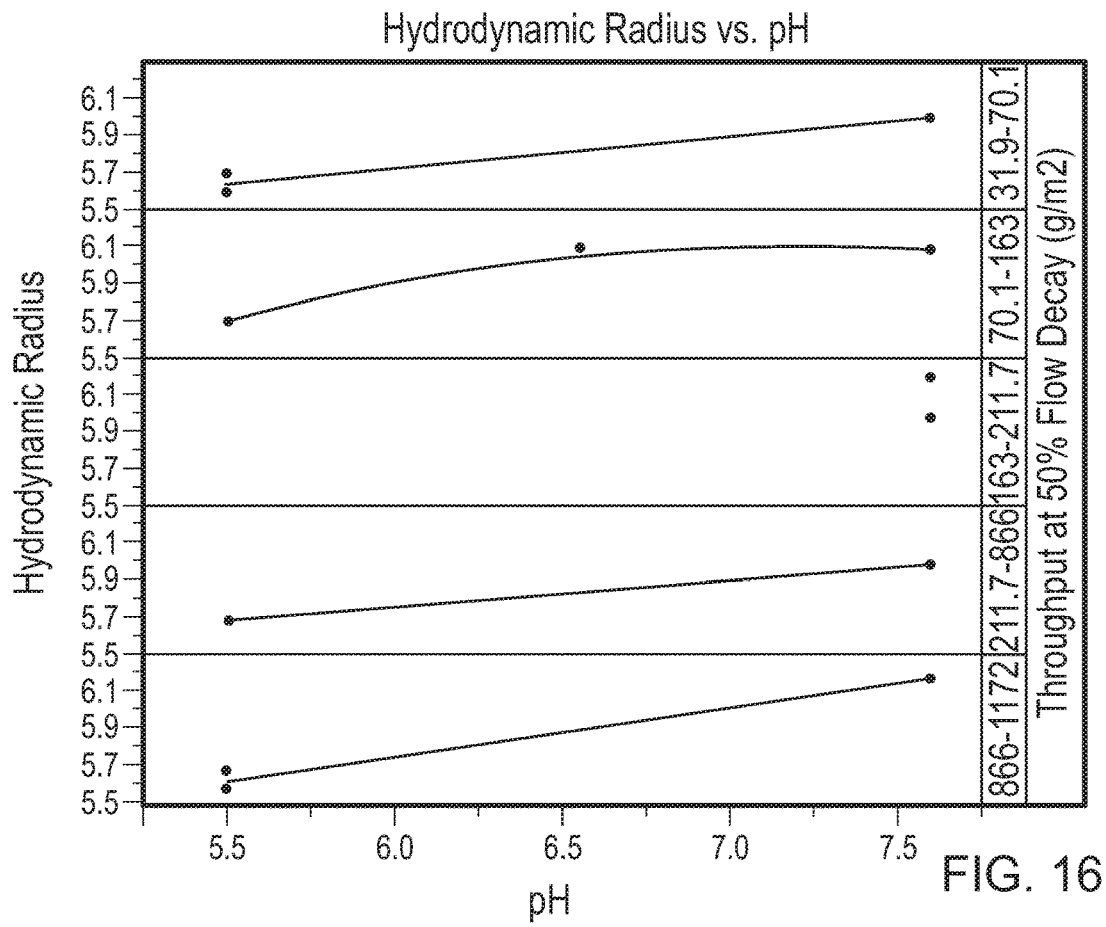

FIG. 16 is a graph showing the relationship between the hydrodynamic radius of BNJ441 human monoclonal antibody in fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either previously pre-filtered using 0.1 μm filter or a Sartorius Virosart® Max pre-filter; the pH of each fluid; and the throughput at 50% flow decay when each fluid is flowed through a Virosart® CPV virus filter.

Figure 17:
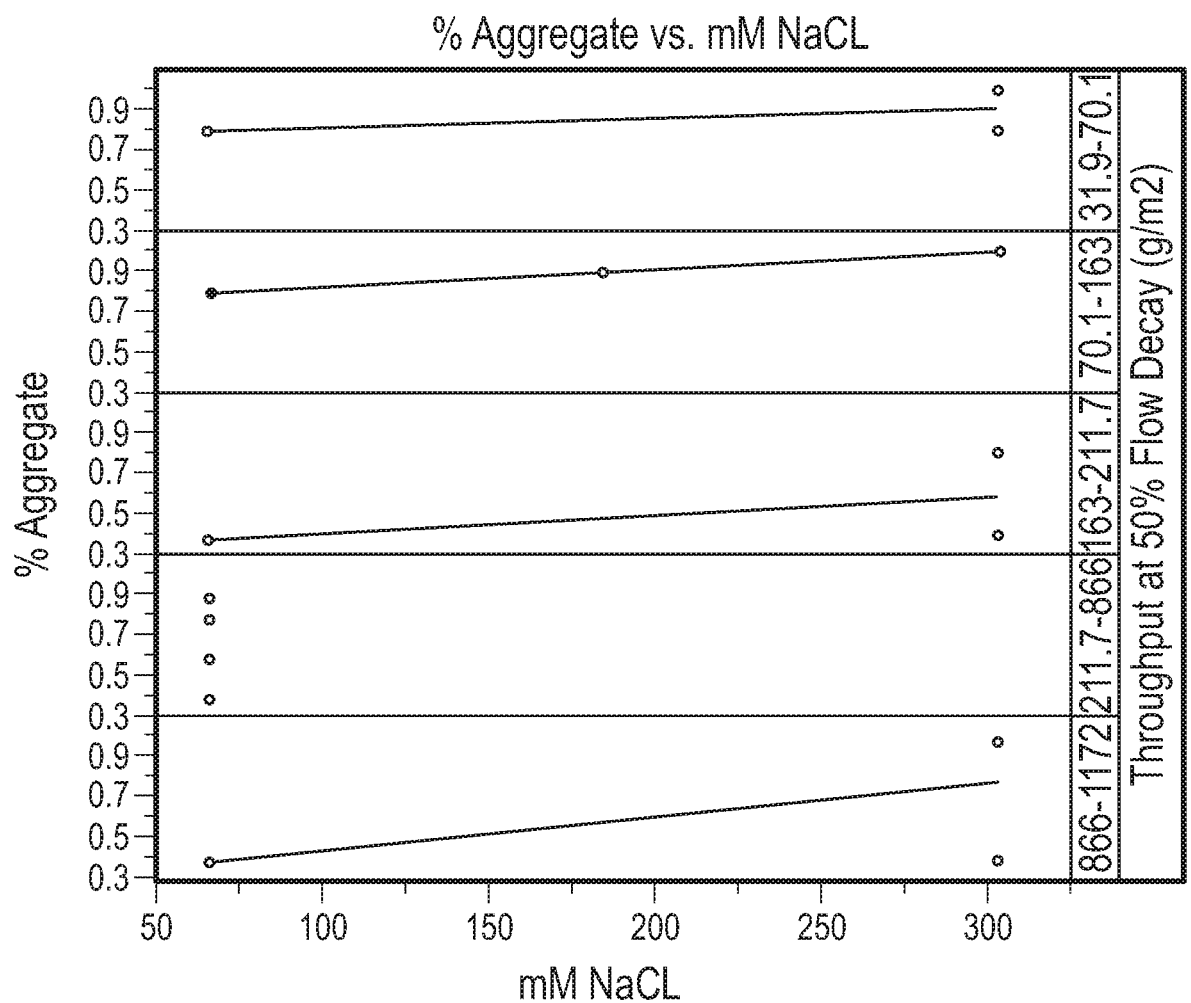

FIG. 17 is a graph showing the relationship between the percentage of aggregates of BNJ441 human monoclonal antibody in fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either previously pre-filtered using 0.1 μm filter or a Sartorius Virosart® Max pre-filter; the concentration of sodium chloride in each fluid; and the throughput at 50% flow decay when each fluid is flowed through a Virosart® CPV virus filter.

Figure 18:
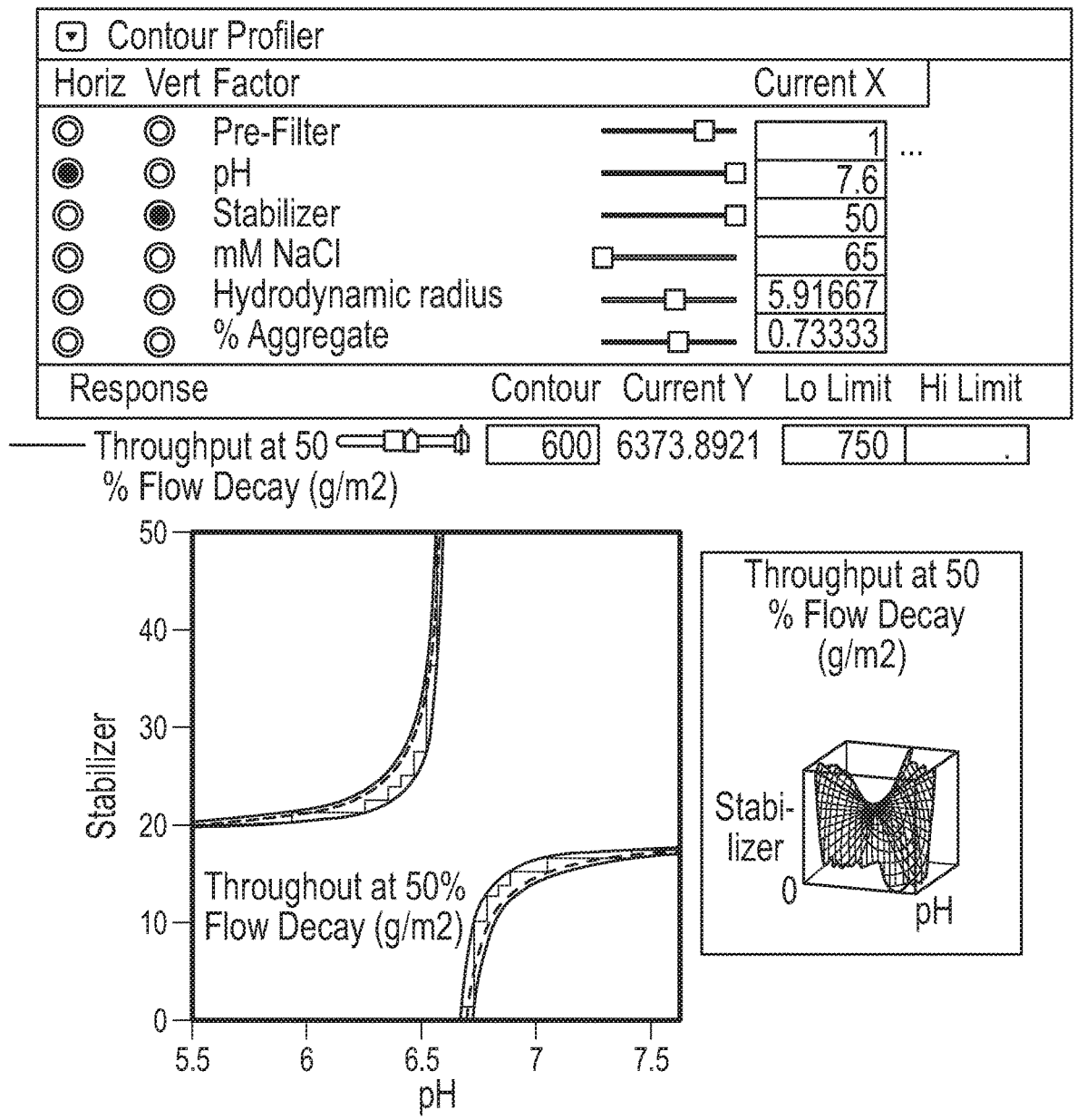

FIG. 18 is a graph showing the minimum concentration of stabilizing agent necessary to achieve a Virosart® CPV virus filter throughput of 750 g/m$^2$ or higher for a fluid having a pH of between 5.5 and 7.6, and including between 2.91 mg/mL to 3.54 mg/mL BNJ441 human monoclonal antibody.

Figure 19:
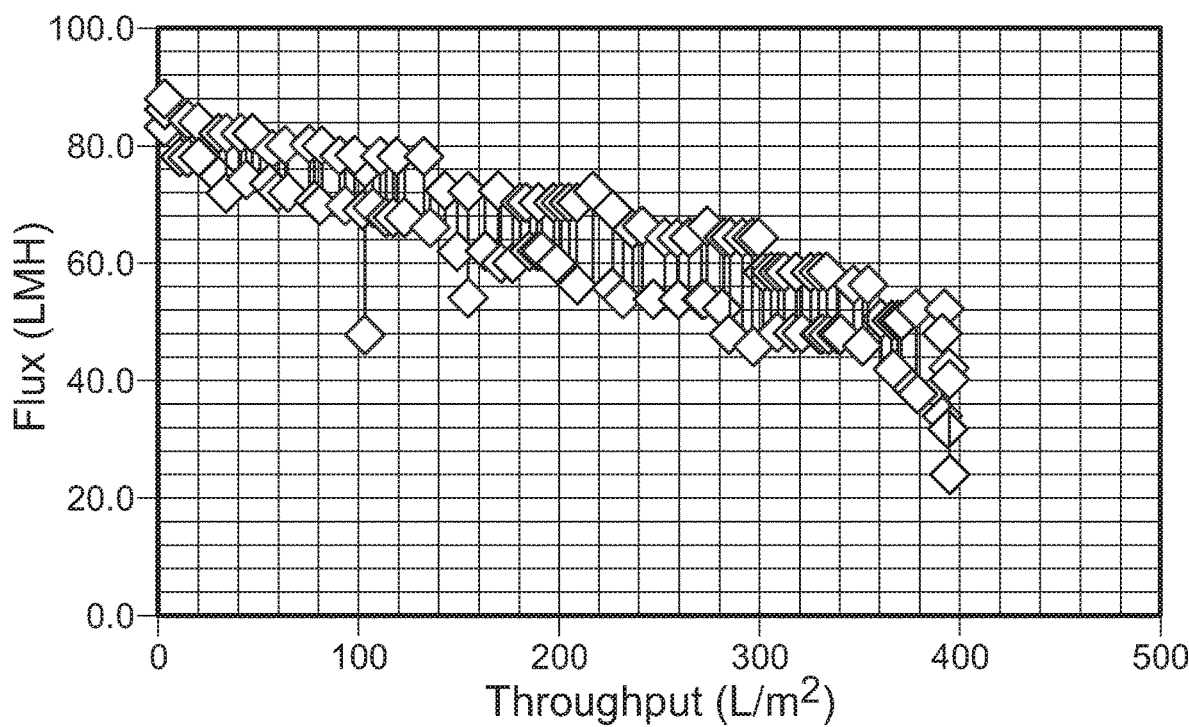

FIG. 19 is a graph showing the flux as compared to throughput when a fluid including 4 mg/mL BNJ441 human monoclonal antibody and 65 mM sodium chloride, and having a pH of 7.0 was flowed through an Asahi Planova® BioEx virus filter.

Figure 20:
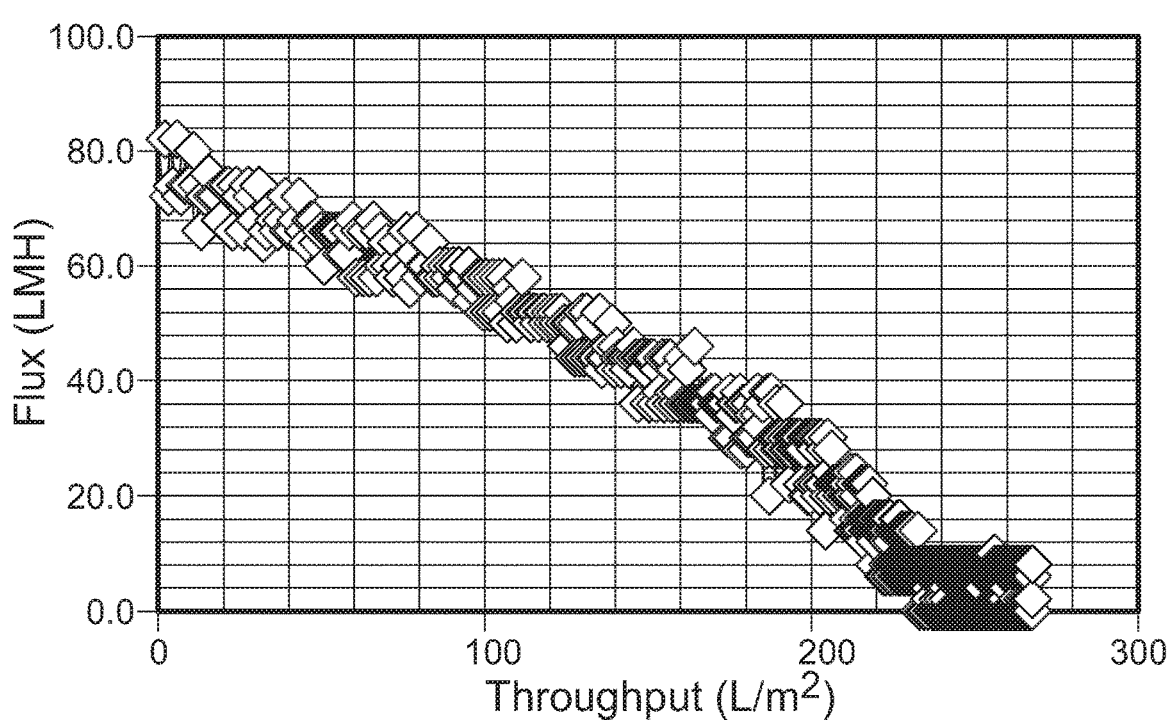

FIG. 20 is a graph showing the flux as compared to throughput when a fluid including 4 mg/mL BNJ441 human monoclonal antibody and 65 mM sodium chloride, and having a pH of 7.75 was flowed through an Asahi Planova® BioEx virus filter.

Figure 21:
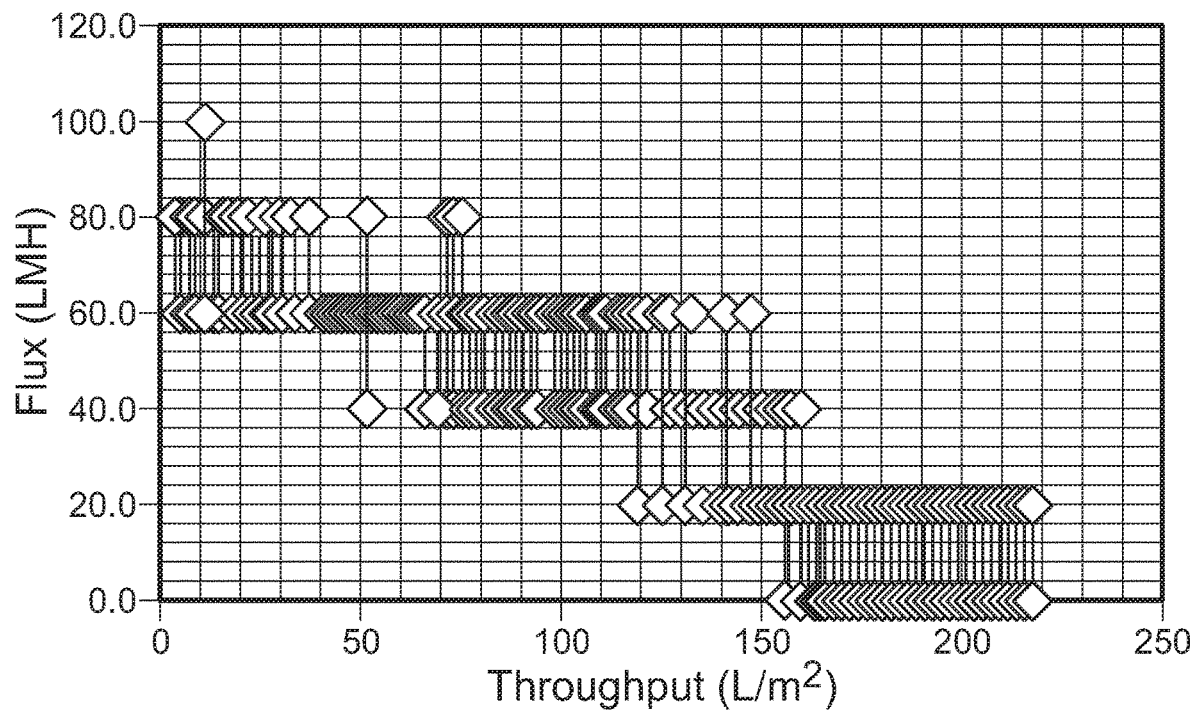

FIG. 21 is a graph showing the flux as compared to throughput when a fluid including 4 mg/mL BNJ441 human monoclonal antibody and 65 mM sodium chloride, and having a pH of 8.5 was flowed through an Asahi Planova® BioEx virus filter.

Figure 22:
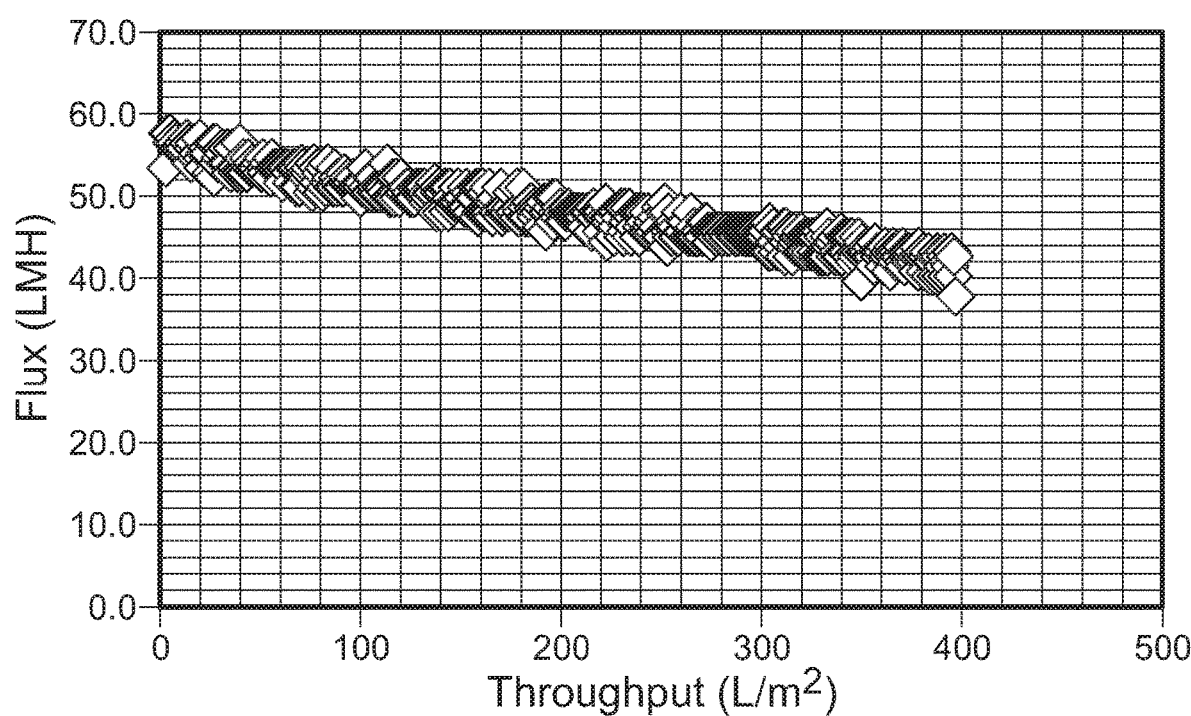

FIG. 22 is a graph showing the flux decay as compared to throughput when a fluid including 4 mg/mL BNJ441 human monoclonal antibody and 65 mM sodium chloride, and having a pH of 7.75 was flowed through an Asahi Planova® 20N virus filter.

Figure 23:
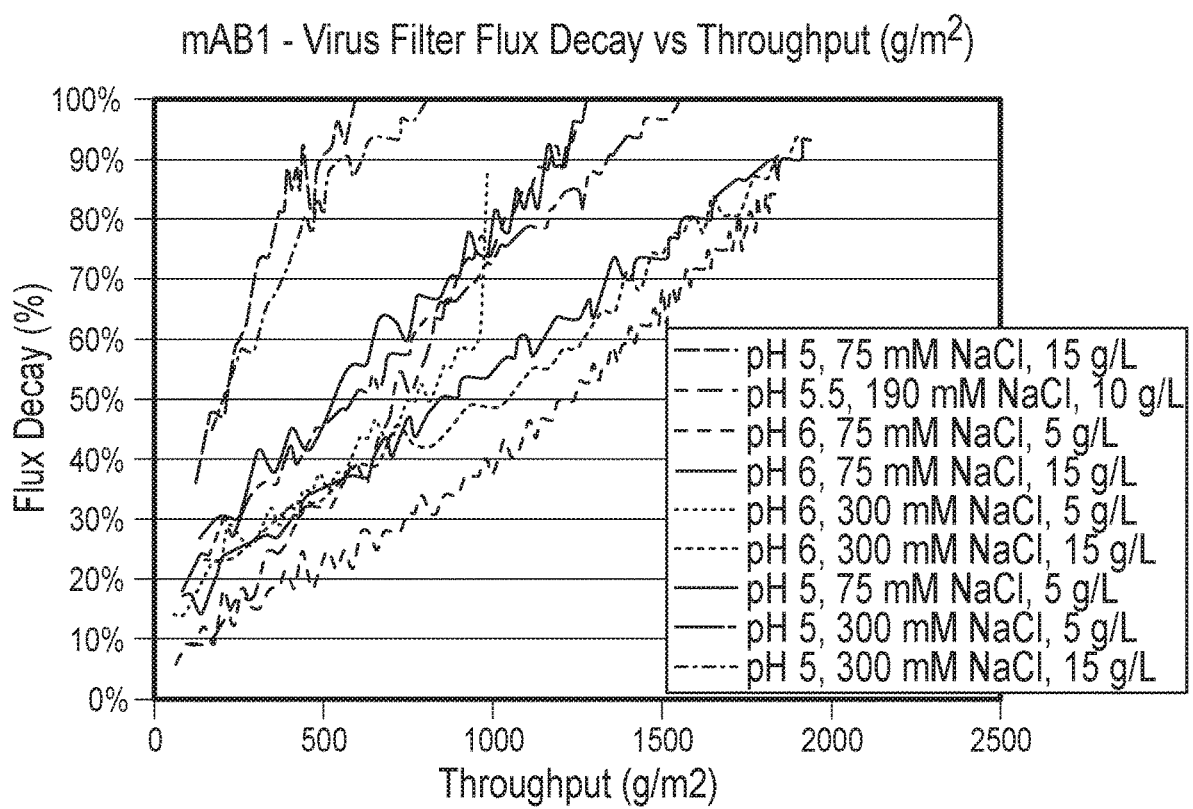

FIG. 23 is a graph showing the flux decay as compared to throughput when a variety of fluids including between 5 mg/mL to 15 mg/mL samalizumab and between 75 mM to 300 mM sodium chloride, and having a pH of 5.0, 5.5, or 6.0 were flowed through a Virosart® CPV virus filter.

Figure 24:
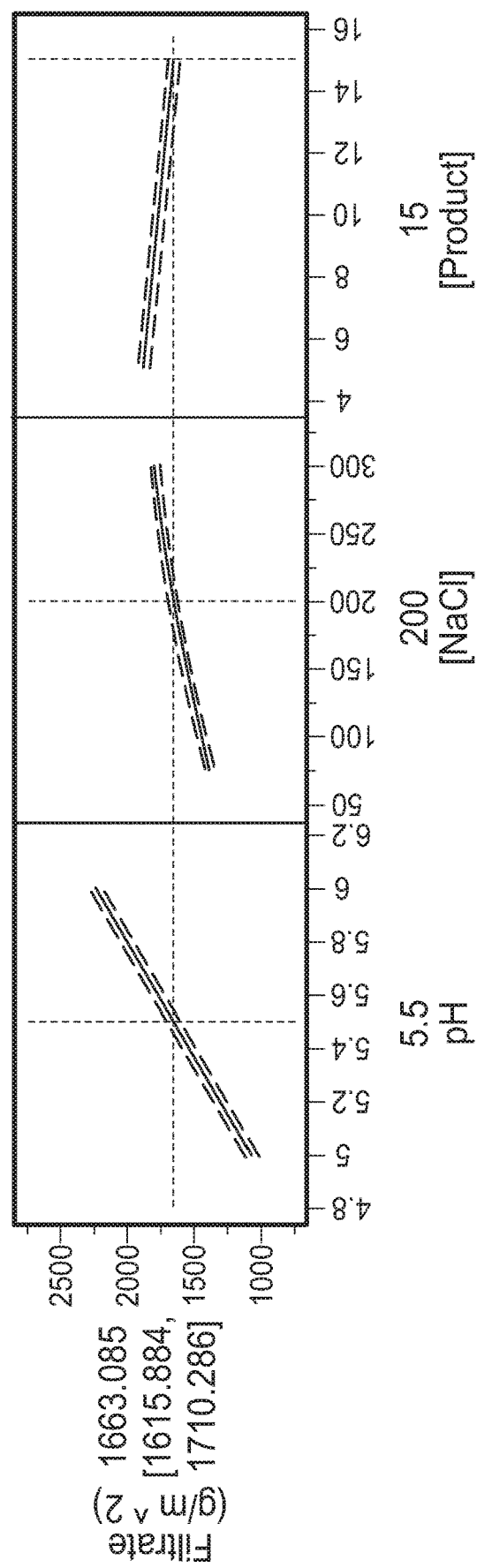

FIG. 24 is a set of three graphs showing the relationship between throughput of a variety of fluids including between 5 mg/mL to 15 mg/mL samalizumab and between 75 mM to 300 mM sodium chloride, and having a pH of 5.0, 5.5, or 6.0 were flowed through a Virosart® CPV virus filter and the pH of each fluid (left graph), the concentration of sodium chloride in each fluid (center graph), and the concentration of samalizumab present in each fluid (right graph). The relationships were determined using statistical analysis.

Figure 25:
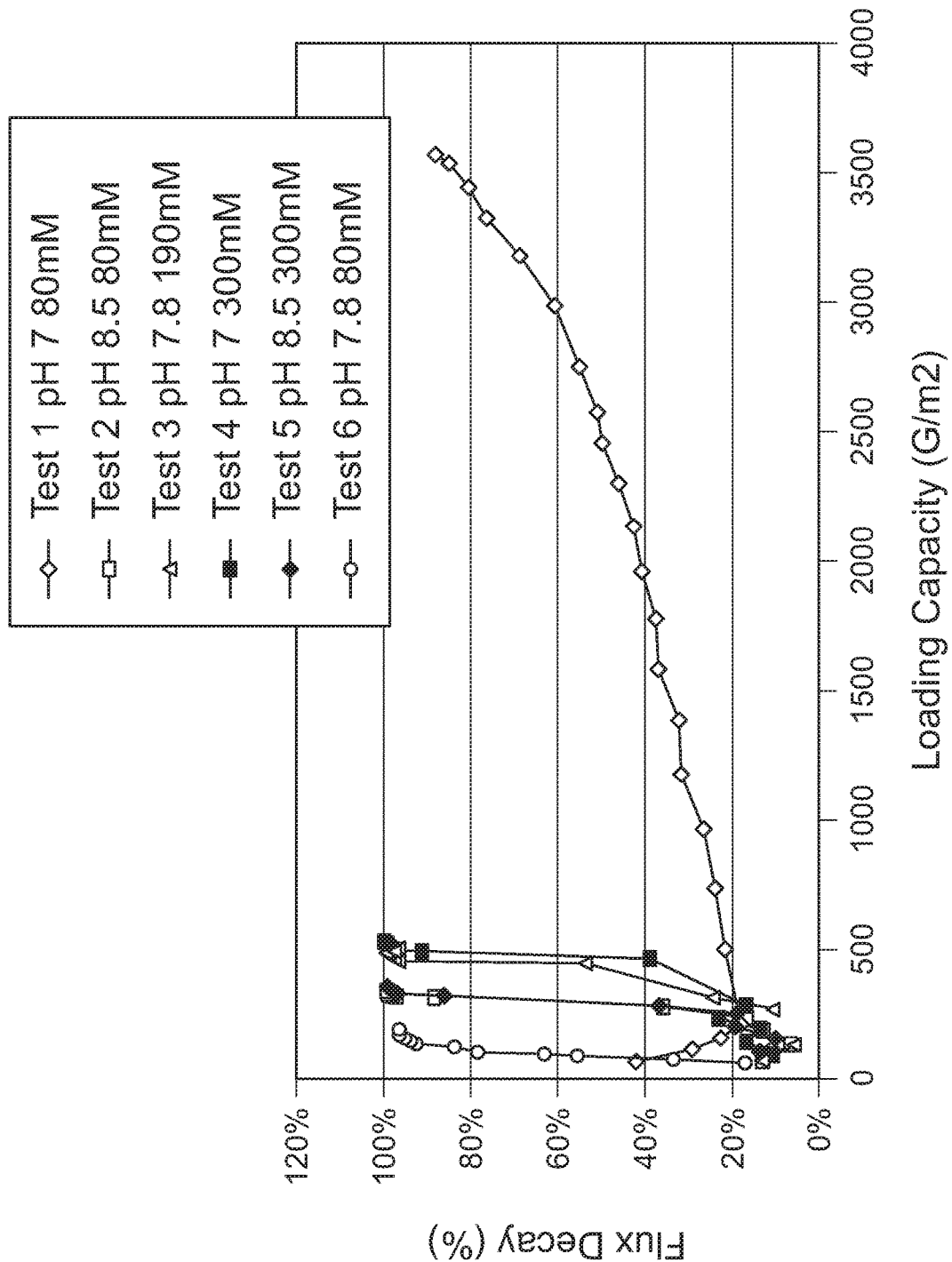

FIG. 25 is graph showing the flux decay as compared to throughput when a variety of fluids including between 9.3 mg/mL to 10 mg/mL BNJ383 monoclonal antibody and between 80 mM to 300 mM sodium chloride, and having a pH of between 7.0 and 8.5 were flowed through a Virosart® CPV virus filter or a Virosart® HF virus filter.

Figure 26:
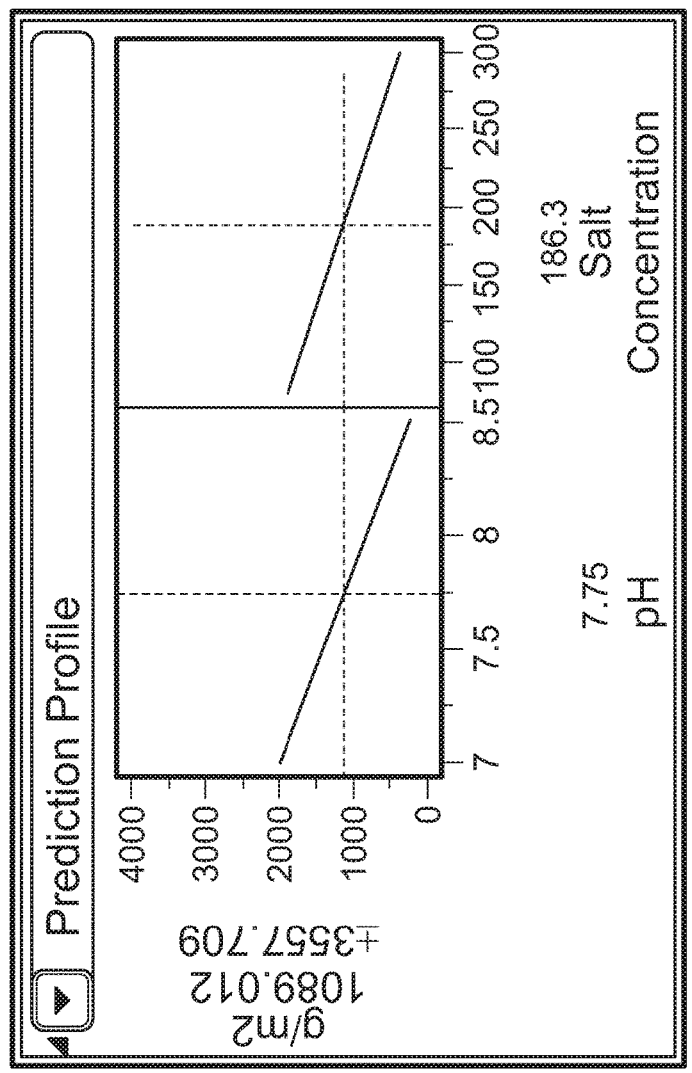

FIG. 26 is a set of two graphs showing the relationship between throughput of a variety of fluids including between 9.3 mg/mL to 10 mg/mL BNJ383 monoclonal antibody and between 80 mM to 300 mM sodium chloride, and having a pH of between 7.0 and 8.5 were flowed through a Virosart® CPV virus filter or a Virosart® HF filter and the pH of each fluid (left graph) and the concentration of sodium chloride in each fluid (right graph). The relationships were determined using statistical analysis.

Figure 27:
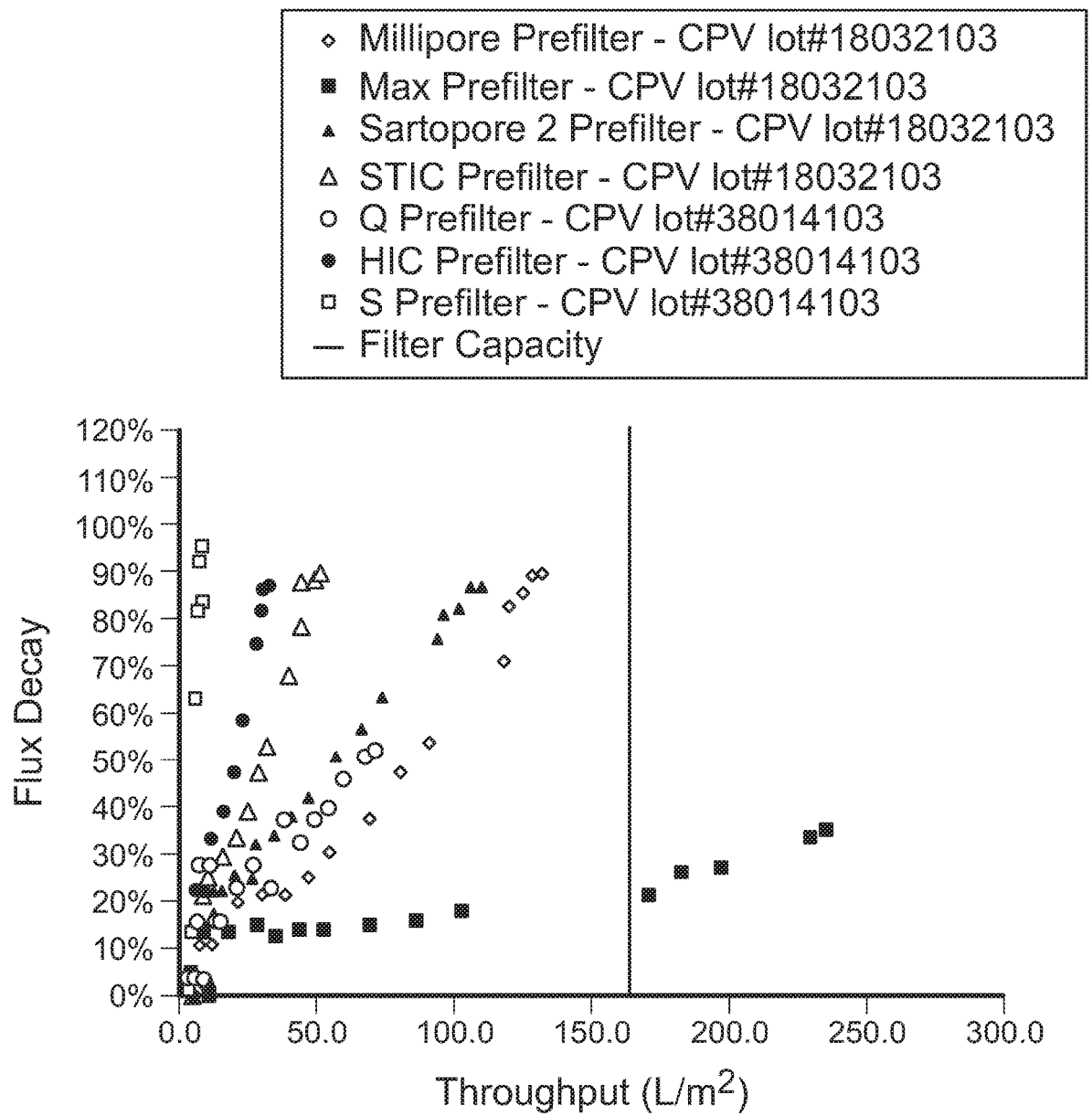

FIG. 27 is a graph showing the flux decay as compared to the throughput of fluid including 7.1 mg/mL eculizumab, 20 mM sodium phosphate, and 80 mM sodium chloride, and having a pH of 6.5, that had been previously pre-filtered using a Millipore 0.5/0.2 µm and 0.5/0.1 µm pre-filter, a Sartorius Virosart® Max pre-filter, a Sartopore® 2 pre-filter, Sartobind STIC® pre-filter, Sartobind® Q pre-filter, Sartobind® HIC Phenyl pre-filter, or a Sartobind® S pre-filter, that is passed through a Virosart® CPV virus filter.

Figure 28:
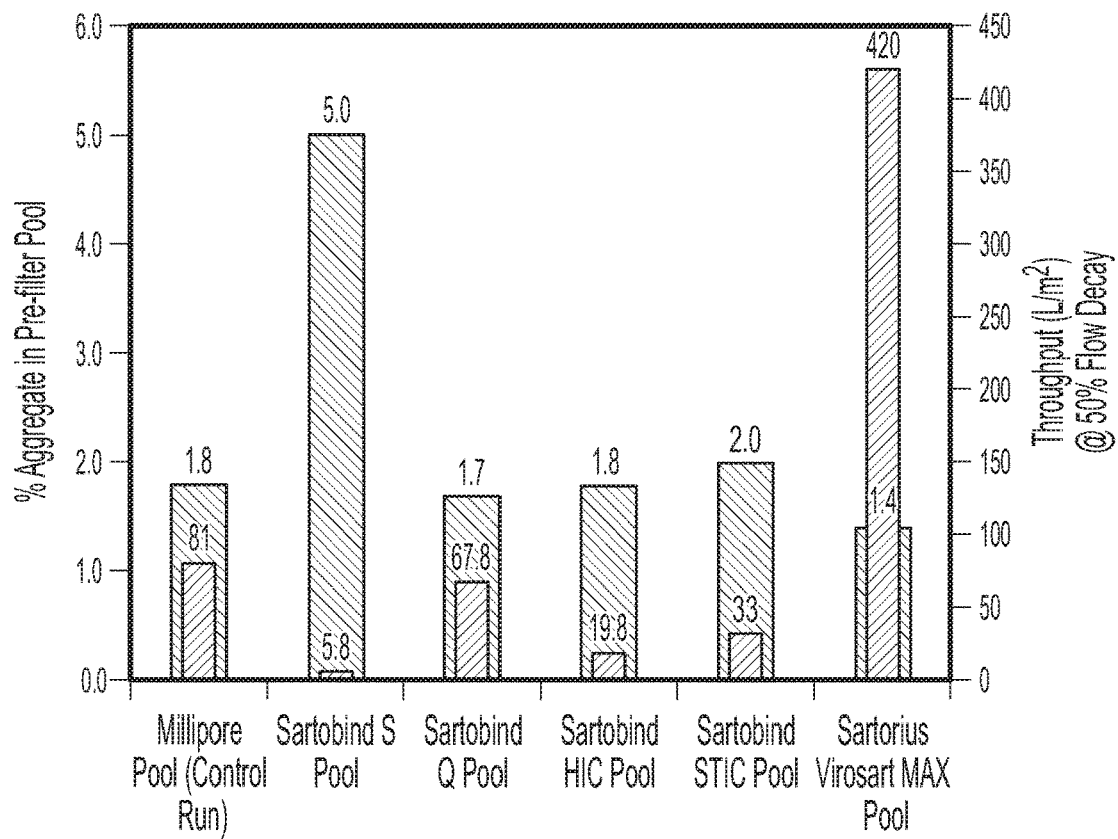

FIG. 28 is a graph showing the percentage of protein aggregates present in fluids including 7.1 mg/mL eculizumab, 20 mM sodium phosphate, and 80 mM sodium chloride, and having a pH of 6.5, after the fluid had been pre-filtered using a Millipore 0.5/0.2 µm and 0.5/0.1 µm pre-filter, a Sartorius Virosart® Max pre-filter, a Sartopore® 2 pre-filter, Sartobind STIC® pre-filter, Sartobind® Q pre-filter, Sartobind® HIC Phenyl pre-filter, or a Sartobind® S pre-filter, as compared to the throughput of a Virosart® CPV virus filter when each fluid is passed through the Virosart® CPV virus filter.

Figure 29:
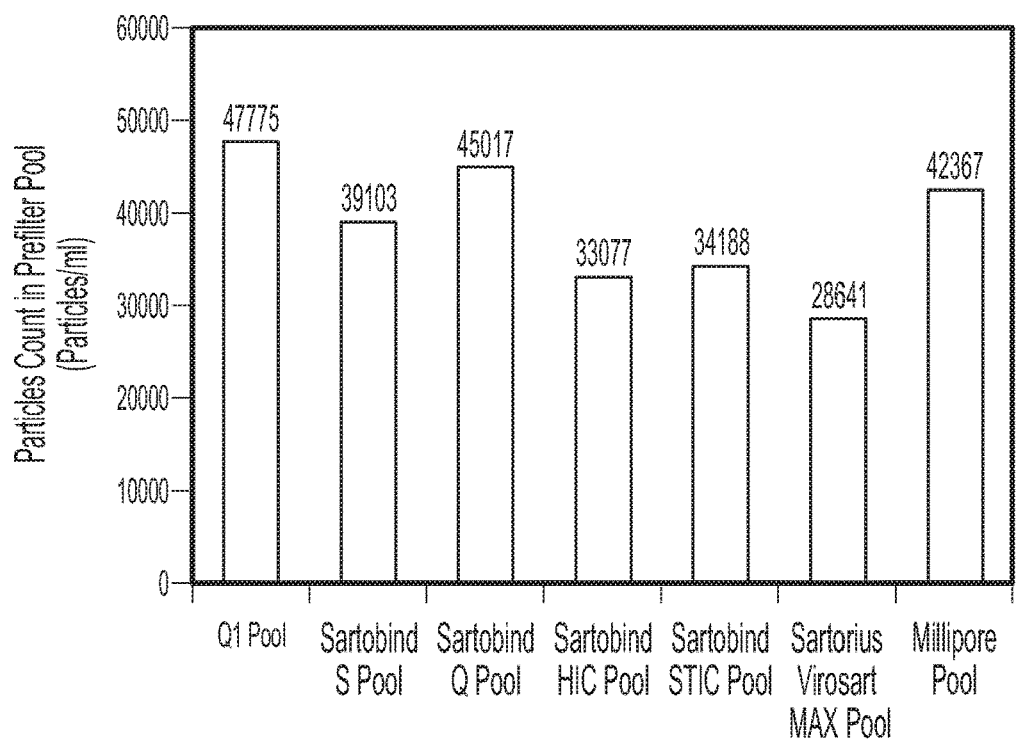

FIG. 29 is a graph showing the number of particles present in fluids including 7.1 mg/mL eculizumab, 20 mM sodium phosphate, and 80 mM sodium chloride, and having a pH of 6.5, after the fluid had been pre-filtered using Millipore 0.5/0.2 µm and 0.5/0.1 µm pre-filter, a Sartorius Virosart® Max pre-filter, a Sartopore 2 pre-filter, Sartobind STIC pre-filter, Sartobind Q pre-filter, Sartobind HIC Phenyl pre-filter, or a Sartobind S pre-filter, and prior to each fluid being subsequently flowed through a Virosart® CPV virus filter, as compared to the throughput of the Virosart® CPV virus filter when each fluid is passed through the Virosart® CPV virus filter.

Figure 30:
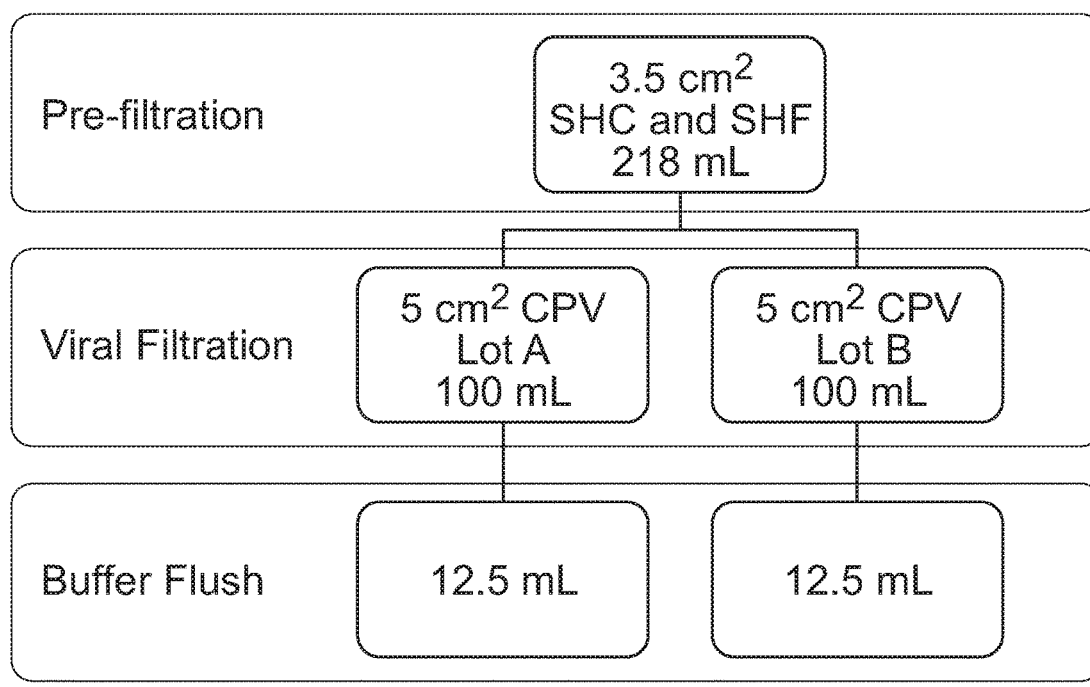

FIG. 30 is a schematic showing the experimental protocols used to perform pre-filtration and filtration with a Virosart® CPV virus filter in Example 6.

Figure 31:
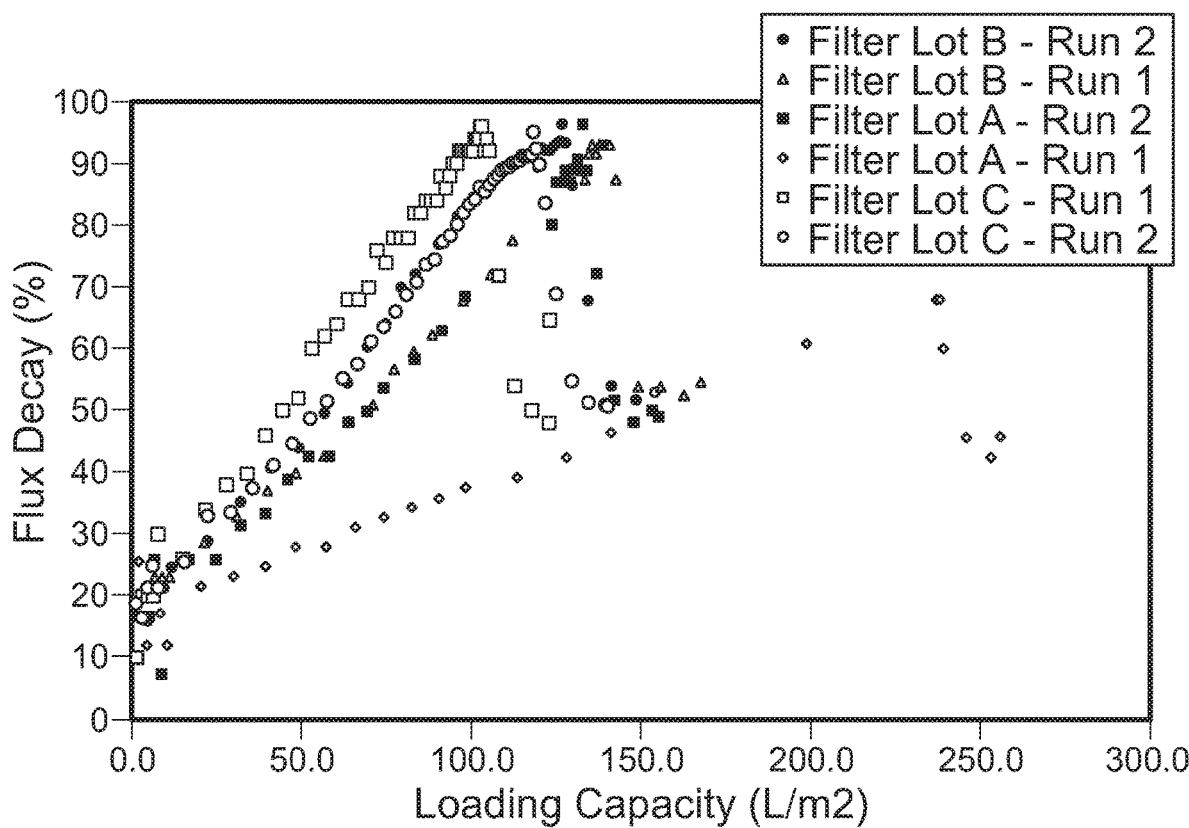

FIG. 31 is a graph of the percentage flux decay as a function of the loading capacity of a Virosart® CPV virus filter from three different lots (Lots A-C). The material loaded onto each Virosart® CPV virus filter was pre-filtered using a 3.5 cm² Millipore 0.5/0.2 µm pre-filter (SHC), and a 0.5 µm/0.1 µm pre-filter (SHR). A Virosart® CPV virus filter from each lot was run in duplicate.

Figure 32:
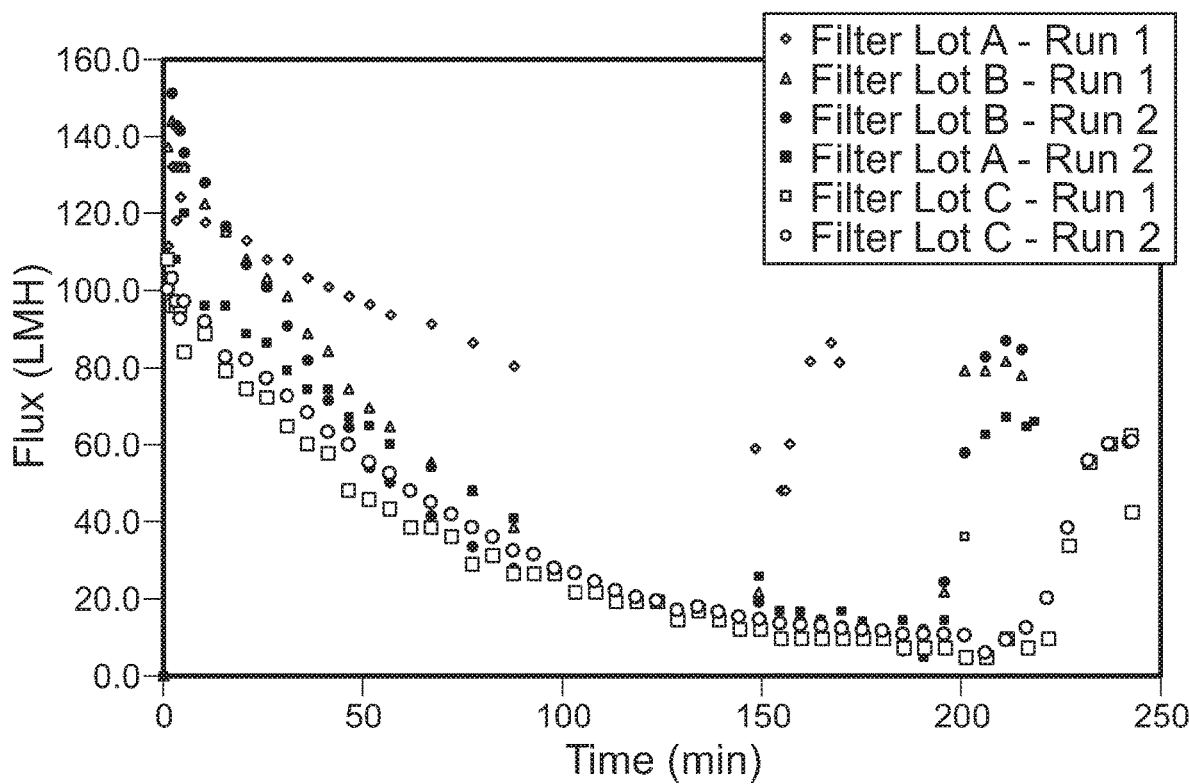

FIG. 32 is a graph of the flux over time of a Virosart® CPV virus filter from three different lots (Lots A-C). The material loaded onto each Virosart® CPV virus filter was pre-filtered using a 3.5 cm² Millipore 0.5/0.2 µm pre-filter (SHC), and a 0.5 µm/0.1 µm pre-filter (SHR). A Virosart® CPV virus filter from each lot was run in duplicate.

Figure 33:
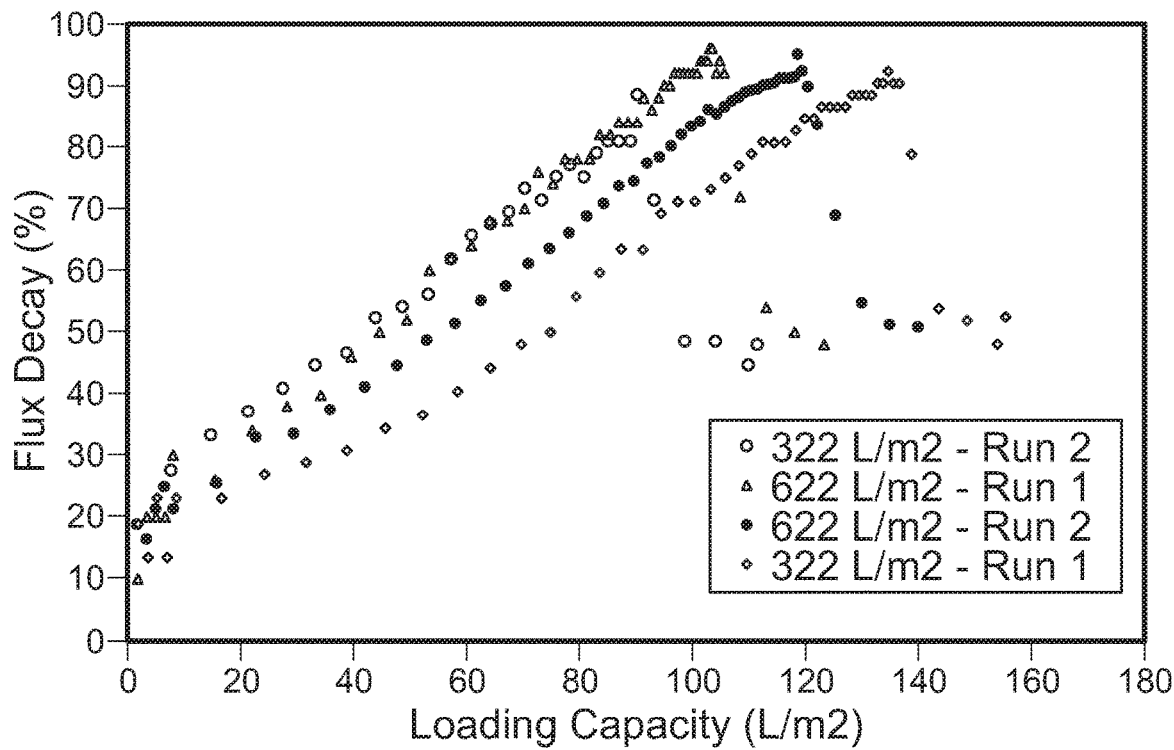

FIG. 33 is a graph of the percentage flux decay as a function of the loading capacity of a Virosart® CPV virus filter loaded with eluate produced using a 3.5 cm² Millipore 0.5/0.2 µm pre-filter (SHC), and a 3.5 cm² 0.5 µm/0.1 µm pre-filter (SHR) run under one of two different conditions: 622 L/m² (218 mL flowed through the 3.5 cm² SHC and 3.5 cm² SHR) or 311 L/m² (109 mL through the 3.5 cm² SHC and 3.5 cm² SHR).

Figure 34:
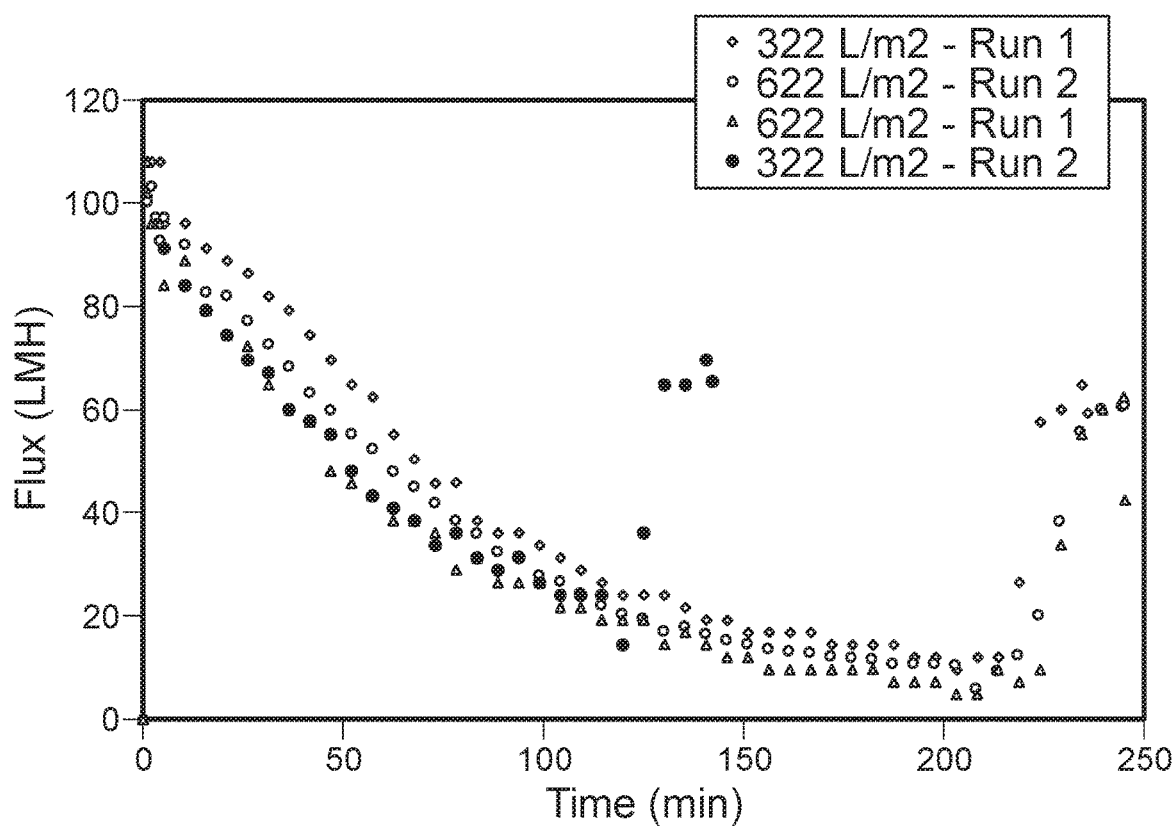

FIG. 34 is a graph of the flux over time of a Virosart® CPV virus filter loaded with eluate produced using a 3.5 cm² Millipore 0.5/0.2 µm pre-filter (SHC), and a 3.5 cm² 0.5 µm/0.1 µm pre-filter (SHR) run under one of two different conditions: 622 L/m² (218 mL flowed through the 3.5 cm² SHC and 3.5 cm² SEM) or 311 L/m² (109 mL through the 3.5 cm² SHC and 3.5 cm² SHR).

Figure 35:
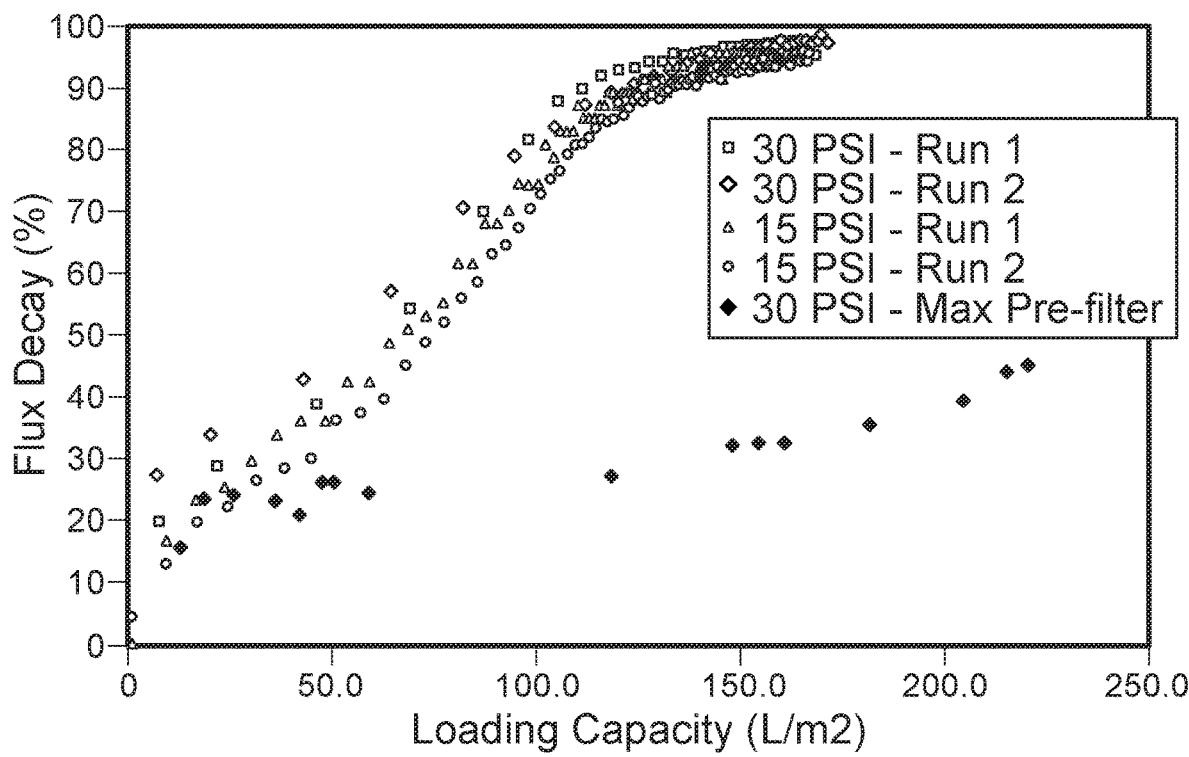

FIG. 35 is a graph of the percentage flux decay as a function of the loading capacity of a Virosart® CPV virus filter runs, with a feed pressure of either 15 psi or 30 psi. The material loaded onto the Virosart® CPV virus filter in-line with a 3.5 cm² Millipore 0.5/0.2 µm pre-filter (SHC), followed by a 3.5 cm² 0.5 µm/0.1 µm pre-filter (SHR), or in-line with a Sartorius Virosart® Max pre-filter (5 cm²).

Figure 36:
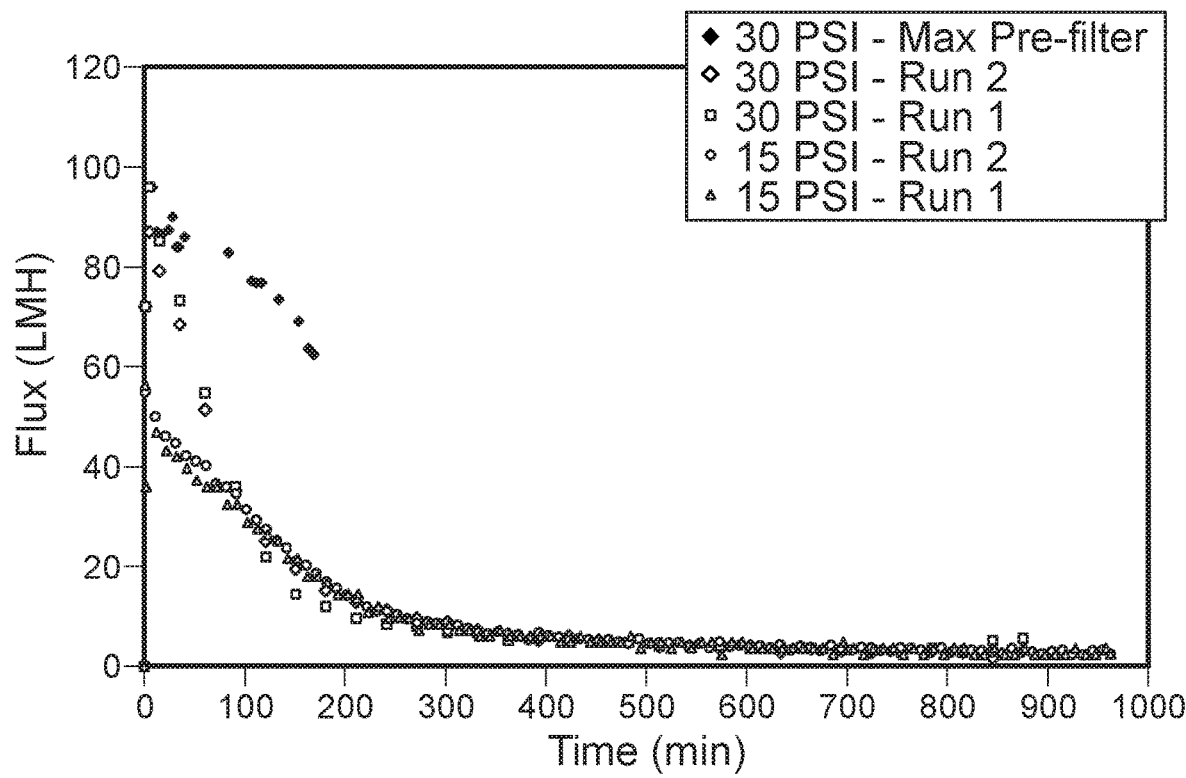

FIG. 36 is a graph of the flux over time of a Virosart® CPV virus filter runs with a feed pressure of either 15 psi or 30 psi. The material was loaded onto the Virosart® CPV virus filter in-line with a 3.5 cm² Millipore 0.5/0.2 µm pre-filter (SHC), followed by a 3.5 cm² 0.5 µm/0.1 µm pre-filter (SHR), or in-line with a Sartorius Virosart® Max pre-filter (5 cm²).

Figure 37:
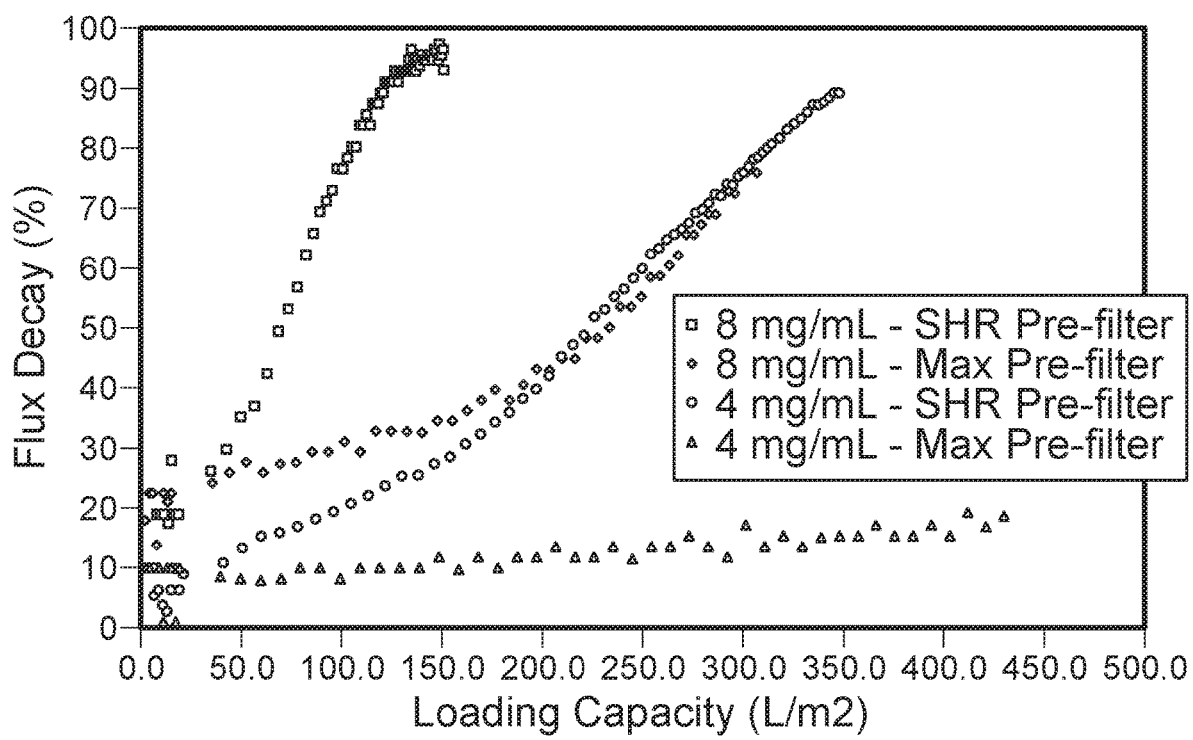

FIG. 37 is a graph of the percentage flux decay as a function of loading capacity of a Virosart® CPV virus filter run with a feed pressure of 27-33 psi, and a buffer chase of 12.5 mL. The material loaded onto the Virosart® CPV virus filter was generated by loading a liquid including 4 mg/mL or 8 mg/mL eculizumab at 623 L/m² onto a 3.5 cm² Millipore 0.5/0.2 µm pre-filter (SHC), and a 3.5 cm² 0.5 µm/0.1 µm pre-filter (SHR), or a Sartorius Virosart® Max pre-filter (5 cm²).

Figure 38:
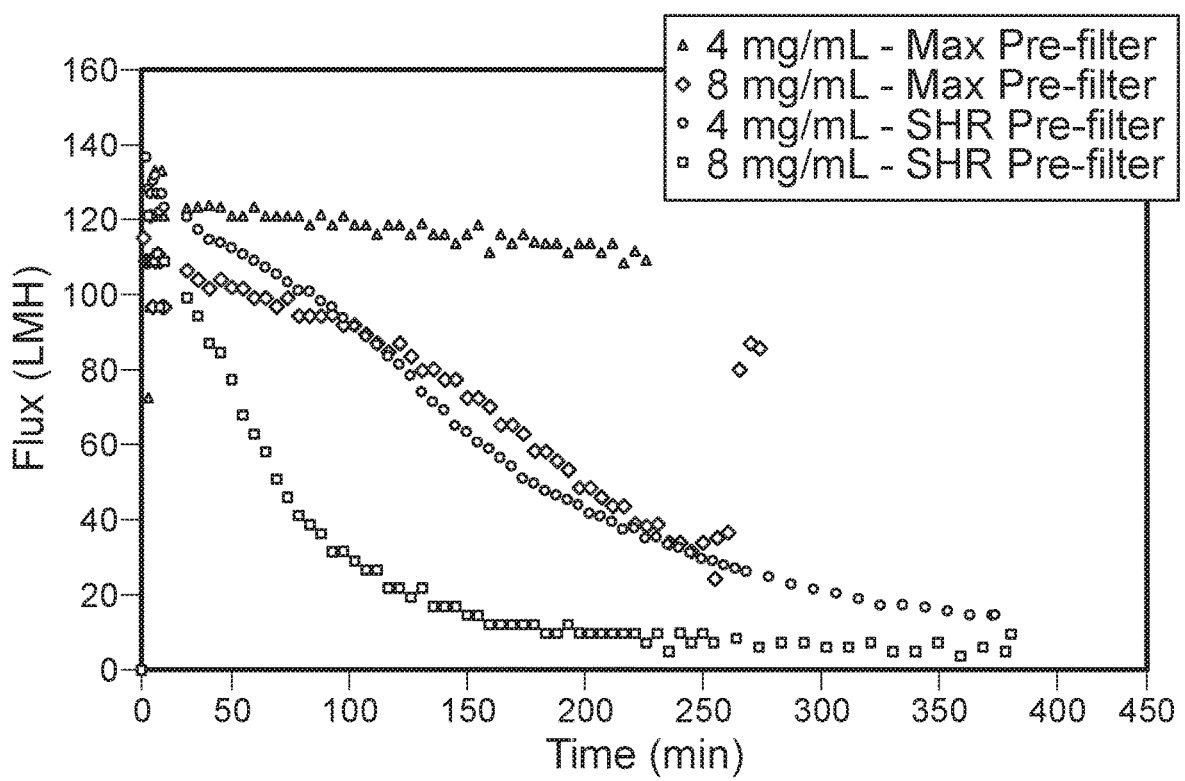

FIG. 38 is a graph of the flux over time of a Virosart® CPV virus filter run with a feed pressure of 27-33 psi, and a buffer chase of 12.5 mL. The material loaded onto the Virosart® CPV virus filter was generated by loading a liquid including 4 mg/mL or 8 mg/mL eculizumab at 623 L/m² onto a 3.5 cm² Millipore 0.5/0.2 µm pre-filter (SHC), and a 3.5 cm² 0.5 µm/0.1 µm pre-filter (SHR), or a Sartorius Virosart® Max pre-filter (5 cm²).

Figure 39:
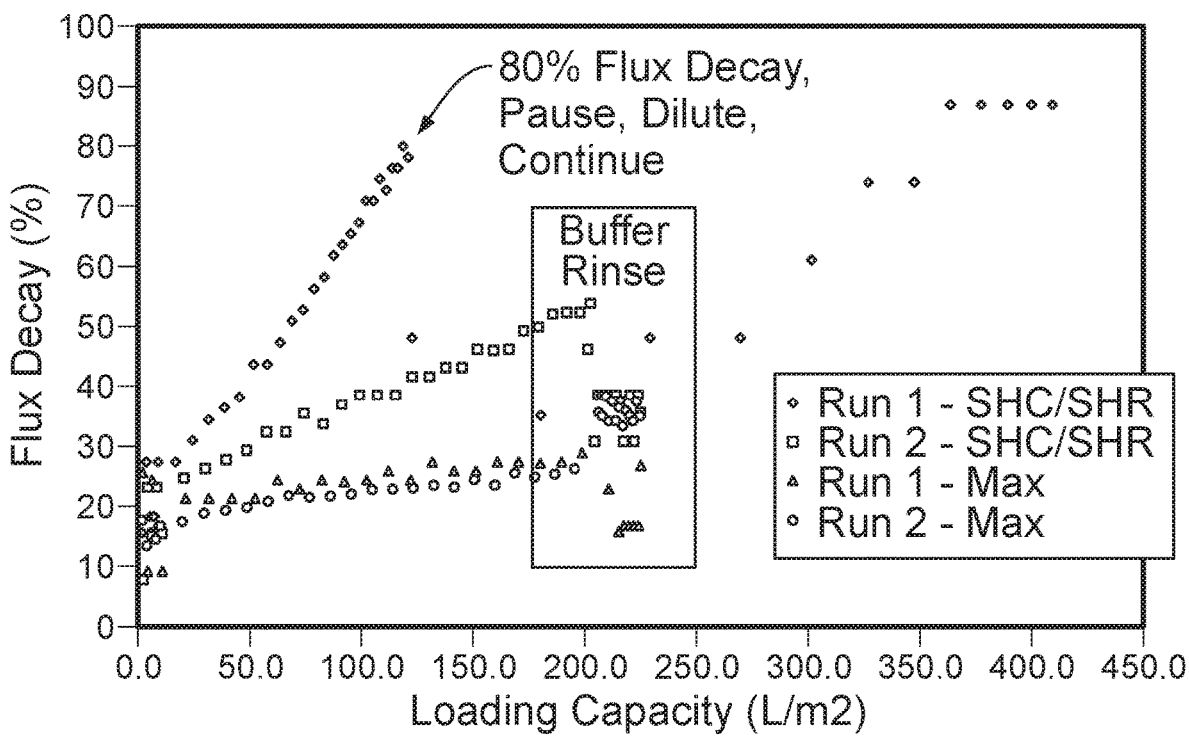

FIG. 39 is a graph of the percentage of flux decay as a function of loading capacity Virosart® CPV virus filter run at 200 L/m², with a feed pressure of 30 psi, and a buffer chase of 12.5 mL. The material loaded onto the Virosart® CPV virus filter was generated by loading a 3.5 cm² Millipore 0.5/0.2 µm pre-filter (SHC), and a 3.5 cm² 0.5 µm/0.1 µm pre-filter (SHR), or a Sartorius Virosart® Max pre-filter (5 cm²). During filtration with the Virosart® CPV virus filter, if an 80% flux decay was reached, the filtration was paused for 60 minutes and the pre-filter eluate loaded onto the Virosart® CPV virus filter was diluted 4-fold in buffer.

Figure 40:
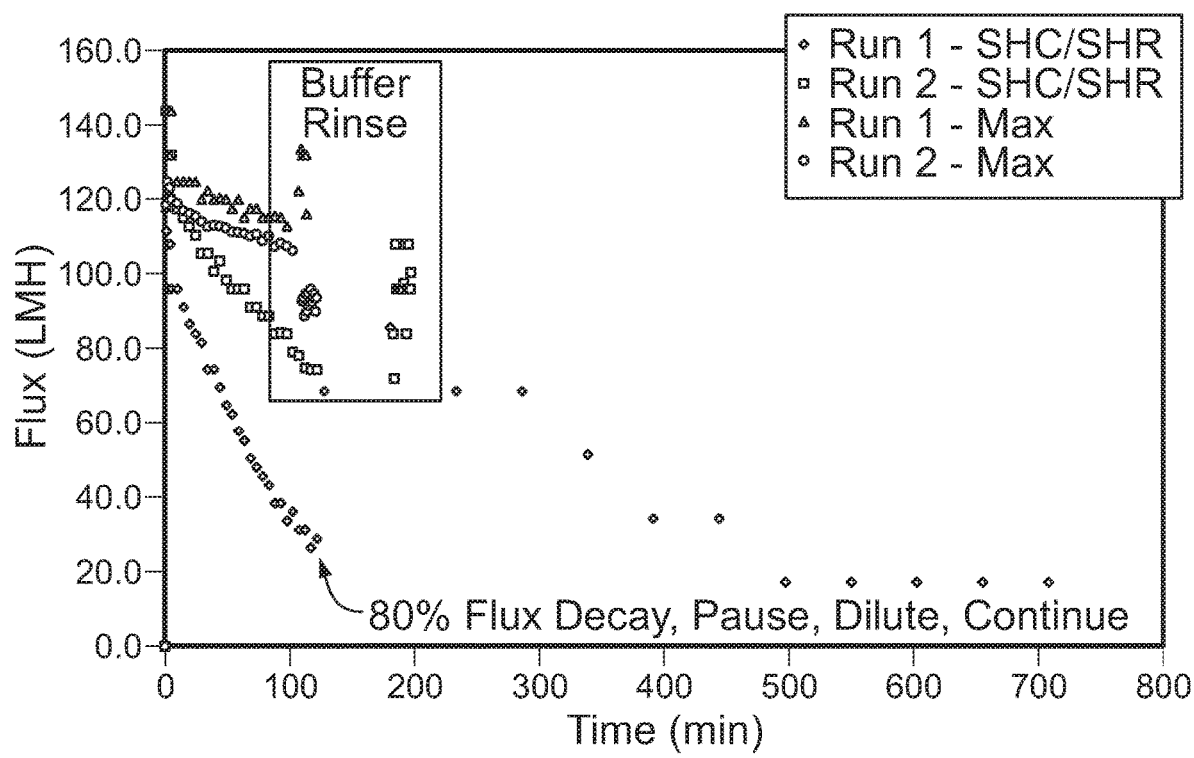

FIG. 40 is a graph of the flux over time of a Virosart® CPV virus filter run at 200 L/m², with a feed pressure of 30 psi, and a buffer chase of 12.5 mL. The material loaded onto the Virosart® CPV virus filter was generated by loading a 3.5 cm² Millipore 0.5/0.2 µm pre-filter (SHC), and a 3.5 cm² 0.5 µm/0.1 µm pre-filter (SHR), or a Sartorius Virosart® Max pre-filter (5 cm²). During filtration with the Virosart® CPV virus filter, if an 80% flux decay was reached, the filtration was paused for 60 minutes and the pre-filter eluate loaded onto the Virosart® CPV virus filter was diluted 4-fold in buffer.

Figure 41:
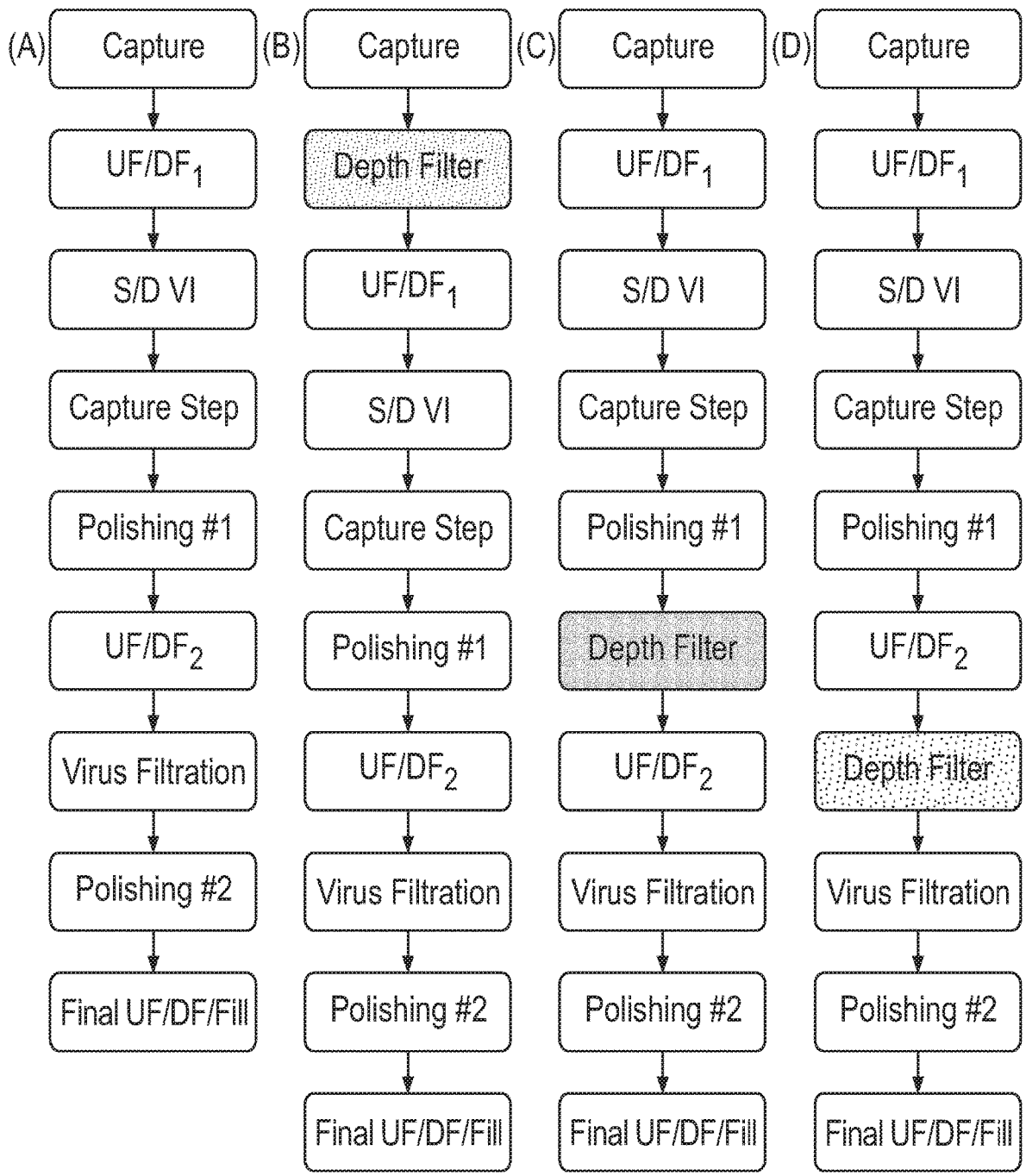

FIG. 41 is a schematic showing the different recombinant fusion protein purification processes tested in Example 10.

Figure 42:
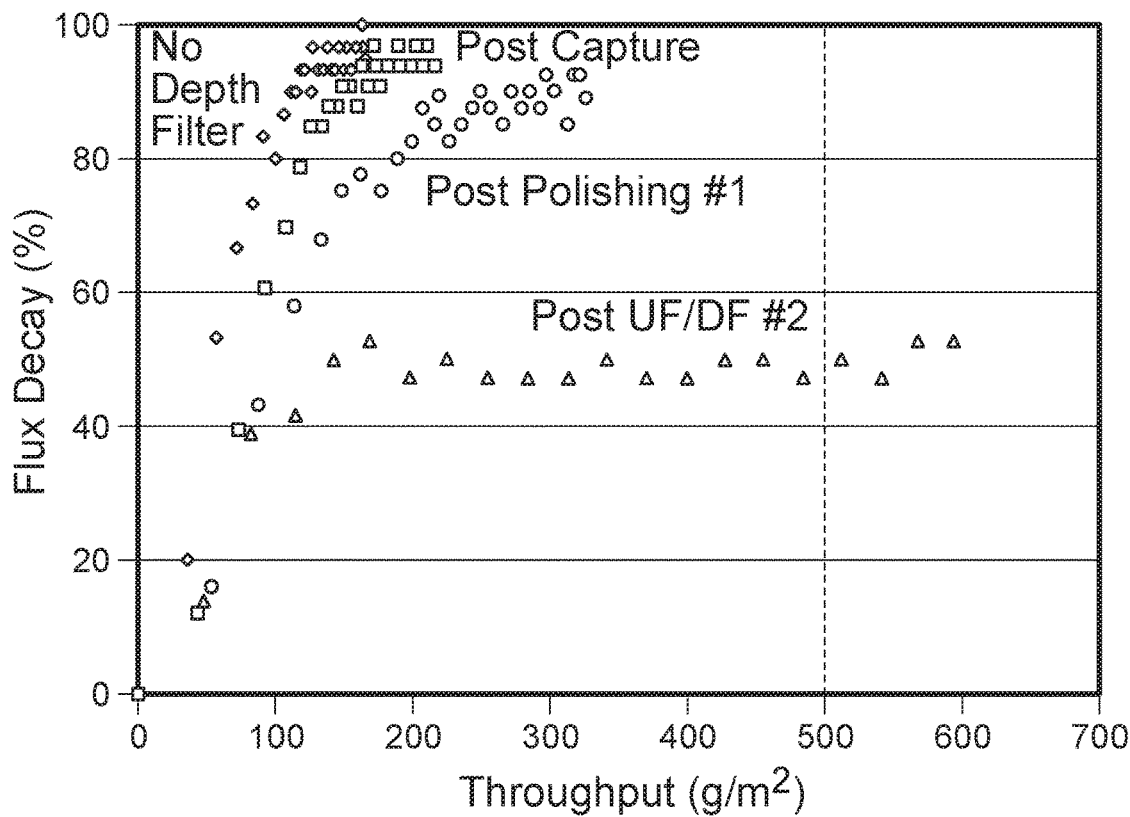

FIG. 42 is a graph of the percentage of flux decay as a function of throughput of a Virosart® CPV virus filter in each of the different recombinant fusion protein purification processes tested in Example 10.

Figure 43:
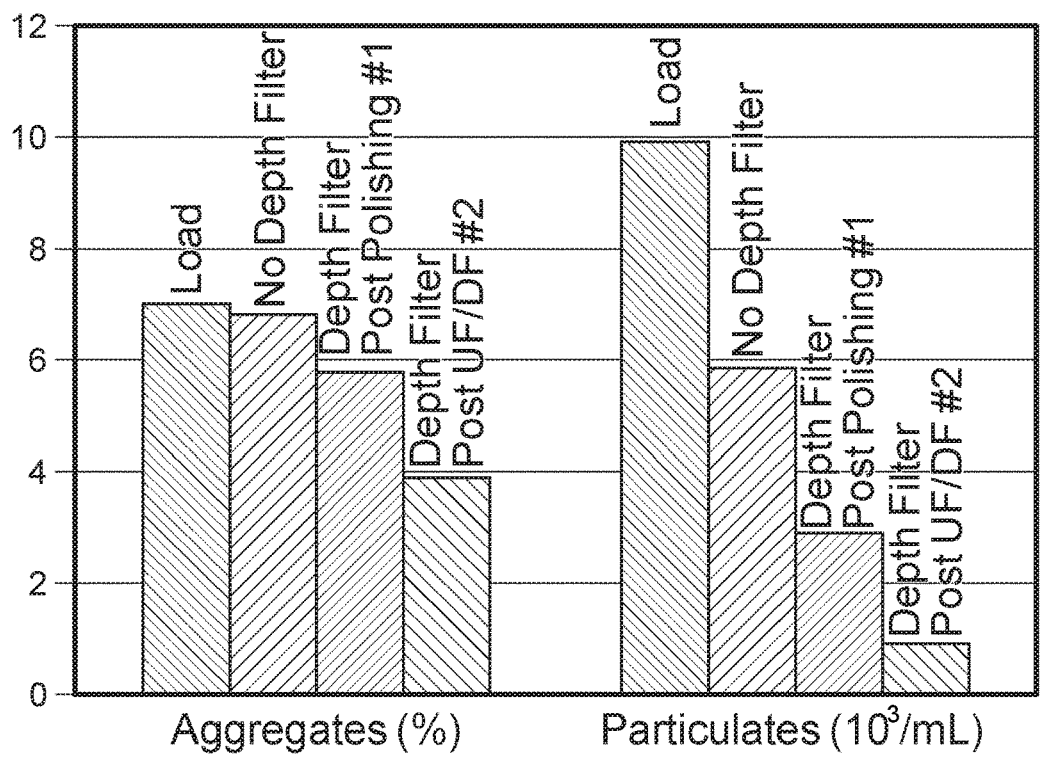

FIG. 43 is a graph showing the percentage of soluble protein aggregates and the level of insoluble protein particles in recombinant fusion protein purified at the end of each of the different purification processes tested in Example 10.

Figure 44A:
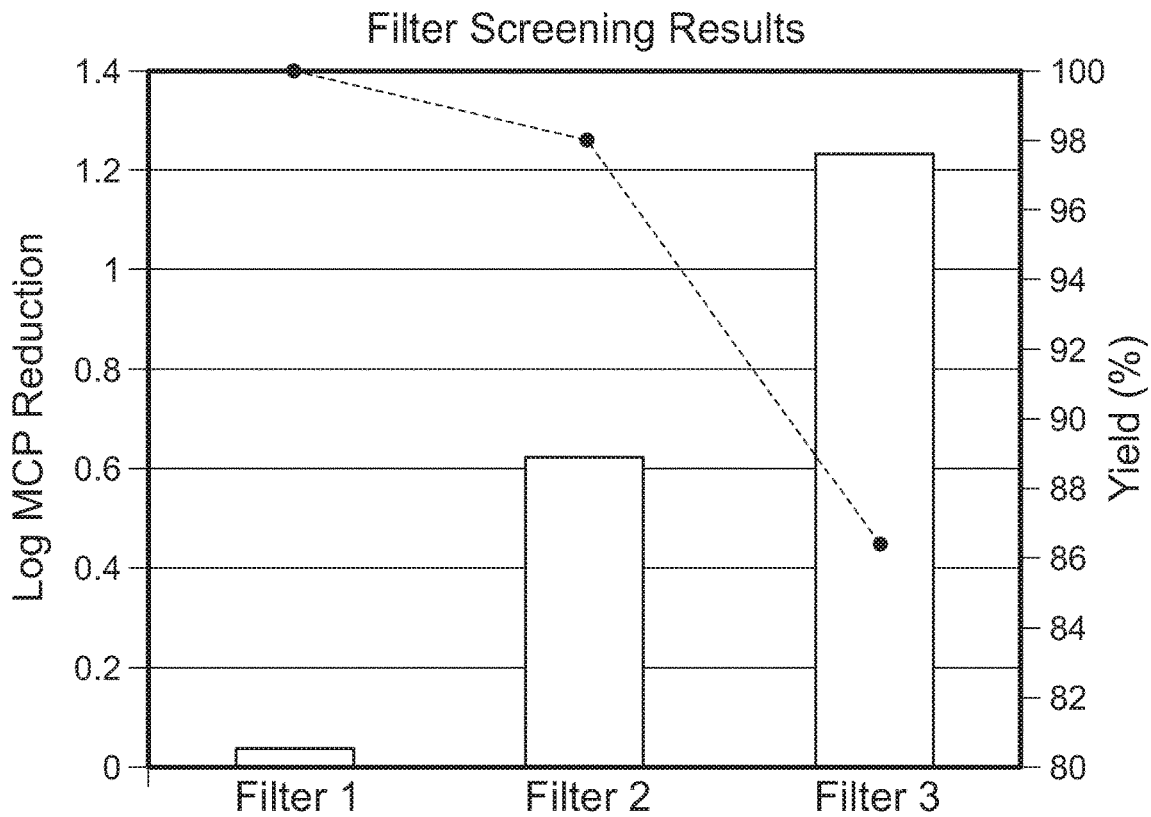

FIG. 44A is a graph showing the ability of each of three different tested depth filters to reduce the level of host cell protein in a fluid including Alexion 1210 and host cell protein.

Figure 44B:
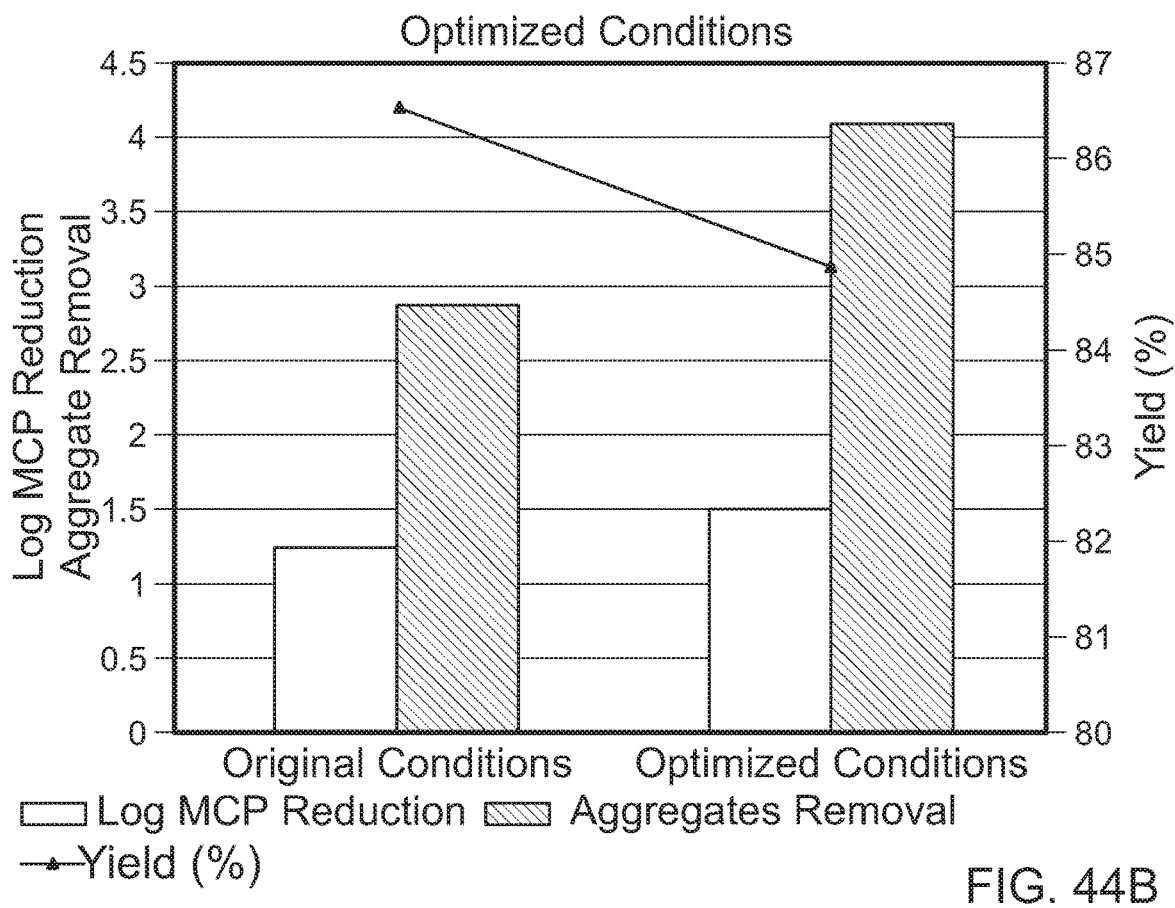

FIG. 44B is a graph showing the level of host cell proteins and soluble protein aggregates in Alexion 1210 purified using a purification process that does not include the use of a depth filter having anionic and hydrophobic properties prior to the viral filtration step (as described in Example 10) and an optimized purification process that includes the use of a wash buffer in the protein A capture step and the use of a depth filter having anionic and hydrophobic properties prior to the viral filtration step (as described in Example 10).

DETAILED DESCRIPTION

During the manufacturing of a recombinant antibody, a fluid including a recombinant antibody is typically flowed through a virus filter in order to improve the safety of the manufactured recombinant antibody. This step of viral filtration can be a rate limiting step in the manufacture of a recombinant antibody if the virus filter used to perform the viral filtration has a low throughput (e.g., a throughput of less than, e.g., 500 g/m$^2$). Provided herein are methods of viral filtration that can result in an throughput of a virus filter of greater than 550 g/m$^2$ (e.g., between about 550 g/m$^2$ and about 15,000 g/m$^2$, between about 550 g/m$^2$ and about 14,000 g/m$^2$, between about 550 g/m$^2$ and about 13,000 g/m$^2$, between about 550 g/m$^2$ and about 12,000 g/m$^2$, between about 550 g/m$^2$ and about 11,000 g/m$^2$, between about 550 g/m$^2$ and about 10,000 g/m$^2$, between about 550 g/m$^2$ and about 9,000 g/m$^2$, between about 550 g/m$^2$ and about 8,000 g/m$^2$, between about 550 g/m$^2$ and about 7,000 g/m$^2$, between about 550 g/m$^2$ and about 6,000 g/m$^2$, between about 550 g/m$^2$ and about 5,000 g/m$^2$, between about 550 g/m$^2$ and about 4,000 g/m$^2$, between about 550 g/m$^2$ and about 3,000 g/m$^2$, between about 550 g/m$^2$ and about 2,500 g/m$^2$, between about 550 g/m$^2$ and about 2,000 g/m$^2$, between about 550 g/m$^2$ and about 1,500 g/m$^2$, between about 550 g/m$^2$ and about 1,000 g/m$^2$, between about 600 g/m$^2$ and about 15,000 g/m$^2$, between about 600 g/m$^2$ and about 14,000 g/m$^2$, between about 600 g/m$^2$ and about 13,000 g/m$^2$, between about 600 g/m$^2$ and about 12,000 g/m$^2$, between about 600 g/m$^2$ and about 11,000 g/m$^2$, between about 600 g/m$^2$ and about 10,000 g/m$^2$, between about 600 g/m$^2$ and about 9,000 g/m$^2$, between about 600 g/m$^2$ and about 8,000 g/m$^2$, between about 600 g/m$^2$ and about 7,000 g/m$^2$, between about 600 g/m$^2$ and about 6,000 g/m$^2$, between about 600 g/m$^2$ and about 5,000 g/m$^2$, between about 600 g/m$^2$ and about 4,000 g/m$^2$, between about 600 g/m$^2$ and about 3,000 g/m$^2$, between about 600 g/m$^2$ and about 2,500 g/m$^2$, between about 600 g/m$^2$ and about 2,000 g/m$^2$, between about 600 g/m$^2$ and about 1,500 g/m$^2$, between about 600 g/m$^2$ and about 1,000 g/m$^2$, between about 700 g/m$^2$ and about 15,000 g/m$^2$, between about 700 g/m$^2$ and about 14,000 g/m$^2$, between about 700 g/m$^2$ and about 13,000 g/m$^2$, between about 700 g/m$^2$ and about 12,000 g/m$^2$, between about 700 g/m$^2$ and about 11,000 g/m$^2$, between about 700 g/m$^2$ and about 10,000 g/m$^2$, between about 700 g/m$^2$ and about 9,000 g/m$^2$, between about 700 g/m$^2$ and about 8,000 g/m$^2$, between about 700 g/m$^2$ and about 7,000 g/m$^2$, between about 700 g/m$^2$ and about 6,000 g/m$^2$, between about 700 g/m$^2$ and about 5,000 g/m$^2$, between about 700 g/m$^2$ and about 4,000 g/m$^2$, between about 700 g/m$^2$ and about 3,000 g/m$^2$, between about 700 g/m$^2$ and about 2,500 g/m$^2$, between about 700 g/m$^2$ and about 2,000 g/m$^2$, between about 700 g/m$^2$ and about 1,500 g/m$^2$, between about 700 g/m$^2$ and about 1,000 g/m$^2$, between about 800 g/m$^2$ and about 15,000 g/m$^2$, between about 800 g/m$^2$ and about 14,000 g/m$^2$, between about 800 g/m$^2$ and about 13,000 g/m$^2$, between about 800 g/m$^2$ and about 12,000 g/m$^2$, between about 800 g/m$^2$ and about 11,000 g/m$^2$, between about 800 g/m$^2$ and about 10,000 g/m$^2$, between about 800 g/m$^2$ and about 9,000 g/m$^2$, between about 800 g/m$^2$ and about 8,000 g/m$^2$, between about 800 g/m$^2$ and about 7,000 g/m$^2$, between about 800 g/m$^2$ and about 6,000 g/m$^2$, between about 800 g/m$^2$ and about 5,000 g/m$^2$, between about 800 g/m$^2$ and about 4,000 g/m$^2$, between about 800 g/m$^2$ and about 3,000 g/m$^2$, between about 800 g/m$^2$ and about 2,500 g/m$^2$, between about 800 g/m$^2$ and about 2,000 g/m$^2$, between about 800 g/m$^2$ and about 1,500 g/m$^2$, between about 800 g/m$^2$ and about 1,000 g/m$^2$, between about 900 g/m$^2$ and about 15,000 g/m$^2$, between about 900 g/m$^2$ and about 14,000 g/m$^2$, between about 900 g/m$^2$ and about 13,000 g/m$^2$, between about 900 g/m$^2$ and about 12,000 g/m$^2$, between about 900 g/m$^2$ and about 11,000 g/m$^2$, between about 900 g/m$^2$ and about 10,000 g/m$^2$, between about 900 g/m$^2$ and about 9,000 g/m$^2$, between about 900 g/m$^2$ and about 8,000 g/m$^2$, between about 900 g/m$^2$ and about 7,000 g/m$^2$, between about 900 g/m$^2$ and about 6,000 g/m$^2$, between about 900 g/m$^2$ and about 5,000 g/m$^2$, between about 900 g/m$^2$ and about 4,000 g/m$^2$, between about 900 g/m$^2$ and about 3,000 g/m$^2$, between about 900 g/m$^2$ and about 2,500 g/m$^2$, between about 900 g/m$^2$ and about 2,000 g/m$^2$, between about 900 g/m$^2$ and about 1,500 g/m$^2$, between about 900 g/m$^2$ and about 1,000 g/m$^2$, between about 1,000 g/m$^2$ and about 15,000 g/m$^2$, between about 1,000 g/m$^2$ and about 14,000 g/m$^2$, between about 1,000 g/m$^2$ and about 13,000 g/m$^2$, between about 1,000 g/m$^2$ and about 12,000 g/m$^2$, between about 1,000 g/m$^2$ and about 11,000 g/m$^2$, between about 1,000 g/m$^2$ and about 10,000 g/m$^2$, between about 1,000 g/m$^2$ and about 9,000 g/m$^2$, between about 1,000 g/m$^2$ and about 8,000 g/m$^2$, between about 1,000 g/m$^2$ and about 7,000 g/m$^2$, between about 1,000 g/m$^2$ and about 6,000 g/m$^2$, between about 1,000 g/m$^2$ and about 5,000 g/m$^2$, between about 1,000 g/m$^2$ and about 4,000 g/m$^2$, between about 1,000 g/m$^2$ and about 3,000 g/m$^2$, between about 1,000 g/m$^2$ and about 2,500 g/m$^2$, between about 1,000 g/m$^2$ and about 2,000 g/m$^2$, between about 1,000 g/m$^2$ and about 1,500 g/m$^2$, between about 1,100 g/m$^2$ and about 15,000 g/m$^2$, between about 1,100 g/m$^2$ and about 14,000 g/m$^2$, between about 1,100 g/m$^2$ and about 13,000 g/m$^2$, between about 1,100 g/m$^2$ and about 12,000 g/m$^2$, between about 1,100 g/m$^2$ and about 11,000 g/m$^2$, between about 1,100 g/m$^2$ and about 10,000 g/m$^2$, between about 1,100 g/m$^2$ and about 9,000 g/m$^2$, between about 1,100 g/m$^2$ and about 8,000 g/m$^2$, between about 1,100 g/m$^2$ and about 7,000 g/m$^2$, between about 1,100 g/m$^2$ and about 6,000 g/m$^2$, between about 1,100 g/m$^2$ and about 5,000 g/m$^2$, between about 1,100 g/m$^2$ and about 4,000 g/m$^2$, between about 1,100 g/m$^2$ and about 3,000 g/m$^2$, between about 1,100 g/m$^2$ and about 2,500 g/m$^2$, between about 1,100 g/m$^2$ and about 2,000 g/m$^2$, between about 1,100 g/m$^2$ and about 1,500 g/m$^2$, between about 1,200 g/m$^2$ and about 15,000 g/m², between about 1,200 g/m² and about 14,000 g/m², between about 1,200 g/m² and about 13,000 g/m², between about 1,200 g/m² and about 12,000 g/m², between about 1,200 g/m² and about 11,000 g/m², between about 1,200 g/m² and about 10,000 g/m², between about 1,200 g/m² and about 9,000 g/m², between about 1,200 g/m² and about 8,000 g/m², between about 1,200 g/m² and about 7,000 g/m², between about 1,200 g/m² and about 6,000 g/m², between about 1,200 g/m² and about 5,000 g/m², between about 1,200 g/m² and about 4,000 g/m², between about 1,200 g/m² and about 3,000 g/m², between about 1,200 g/m² and about 2,500 g/m², between about 1,200 g/m² and about 2,000 g/m², between about 1,200 g/m² and about 1,500 g/m², between about 1,300 g/m² and about 15,000 g/m², between about 1,300 g/m² and about 14,000 g/m², between about 1,300 g/m² and about 13,000 g/m², between about 1,300 g/m² and about 12,000 g/m², between about 1,300 g/m² and about 11,000 g/m², between about 1,300 g/m² and about 10,000 g/m², between about 1,300 g/m² and about 9,000 g/m², between about 1,300 g/m² and about 8,000 g/m², between about 1,300 g/m² and about 7,000 g/m², between about 1,300 g/m² and about 6,000 g/m², between about 1,300 g/m² and about 5,000 g/m², between about 1,300 g/m² and about 4,000 g/m², between about 1,300 g/m² and about 3,000 g/m², between about 1,300 g/m² and about 2,500 g/m², between about 1,300 g/m² and about 2,000 g/m², between about 1,400 g/m² and about 15,000 g/m², between about 1,400 g/m² and about 14,000 g/m², between about 1,400 g/m² and about 13,000 g/m², between about 1,400 g/m² and about 12,000 g/m², between about 1,400 g/m² and about 11,000 g/m², between about 1,400 g/m² and about 10,000 g/m², between about 1,400 g/m² and about 9,000 g/m², between about 1,400 g/m² and about 8,000 g/m², between about 1,400 g/m² and about 7,000 g/m², between about 1,400 g/m² and about 6,000 g/m², between about 1,400 g/m² and about 5,000 g/m², between about 1,400 g/m² and about 4,000 g/m², between about 1,400 g/m² and about 3,000 g/m², between about 1,400 g/m² and about 2,500 g/m², between about 1,400 g/m² and about 2,000 g/m², between about 1,500 g/m² and about 15,000 g/m², between about 1,500 g/m² and about 14,000 g/m², between about 1,500 g/m² and about 13,000 g/m², between about 1,500 g/m² and about 12,000 g/m², between about 1,500 g/m² and about 11,000 g/m², between about 1,500 g/m² and about 10,000 g/m², between about 1,500 g/m² and about 9,000 g/m², between about 1,500 g/m² and about 8,000 g/m², between about 1,500 g/m² and about 7,000 g/m², between about 1,500 g/m² and about 6,000 g/m², between about 1,500 g/m² and about 5,000 g/m², between about 1,500 g/m² and about 4,000 g/m², between about 1,500 g/m² and about 3,000 g/m², between about 1,500 g/m² and about 2,500 g/m², between about 1,500 g/m² and about 2,000 g/m², between about 1,600 g/m² and about 15,000 g/m², between about 1,600 g/m² and about 14,000 g/m², between about 1,600 g/m² and about 13,000 g/m², between about 1,600 g/m² and about 12,000 g/m², between about 1,600 g/m² and about 11,000 g/m², between about 1,600 g/m² and about 10,000 g/m², between about 1,600 g/m² and about 9,000 g/m², between about 1,600 g/m² and about 8,000 g/m², between about 1,600 g/m² and about 7,000 g/m², between about 1,600 g/m² and about 6,000 g/m², between about 1,600 g/m² and about 5,000 g/m², between about 1,600 g/m² and about 4,000 g/m², between about 1,600 g/m² and about 3,000 g/m², between about 1,600 g/m² and about 2,500 g/m², between about 1,600 g/m² and about 2,000 g/m², between about 1,700 g/m² and about 15,000 g/m², between about 1,700 g/m² and about 14,000 g/m², between about 1,700 g/m² and about 13,000 g/m², between about 1,700 g/m² and about 12,000 g/m², between about 1,700 g/m² and about 11,000 g/m², between about 1,700 g/m² and about 10,000 g/m², between about 1,700 g/m² and about 9,000 g/m², between about 1,700 g/m² and about 8,000 g/m², between about 1,700 g/m² and about 7,000 g/m², between about 1,700 g/m² and about 6,000 g/m², between about 1,700 g/m² and about 5,000 g/m², between about 1,700 g/m² and about 4,000 g/m², between about 1,700 g/m² and about 3,000 g/m², between about 1,700 g/m² and about 2,500 g/m², between about 1,800 g/m² and about 15,000 g/m², between about 1,800 g/m² and about 14,000 g/m², between about 1,800 g/m² and about 13,000 g/m², between about 1,800 g/m² and about 12,000 g/m², between about 1,800 g/m² and about 11,000 g/m², between about 1,800 g/m² and about 10,000 g/m², between about 1,800 g/m² and about 9,000 g/m², between about 1,800 g/m² and about 8,000 g/m², between about 1,800 g/m² and about 7,000 g/m², between about 1,800 g/m² and about 6,000 g/m², between about 1,800 g/m² and about 5,000 g/m², between about 1,800 g/m² and about 4,000 g/m², between about 1,800 g/m² and about 3,000 g/m², between about 1,800 g/m² and about 2,500 g/m², between about 1,800 g/m² and about 2,000 g/m², between about 2,000 g/m² and about 15,000 g/m², between about 2,000 g/m² and about 14,000 g/m², between about 2,000 g/m² and about 13,000 g/m², between about 2,000 g/m² and about 12,000 g/m², between about 2,000 g/m² and about 11,000 g/m², between about 2,000 g/m² and about 10,000 g/m², between about 2,000 g/m² and about 9,000 g/m², between about 2,000 g/m² and about 8,000 g/m², between about 2,000 g/m² and about 7,000 g/m², between about 2,000 g/m² and about 6,000 g/m², between about 2,000 g/m² and about 5,000 g/m², between about 2,000 g/m² and about 4,000 g/m², between about 2,000 g/m² and about 3,000 g/m², between about 2,500 g/m² and about 15,000 g/m², between about 2,500 g/m² and about 14,000 g/m², between about 2,500 g/m² and about 13,000 g/m², between about 2,500 g/m² and about 12,000 g/m², between about 2,500 g/m² and about 11,000 g/m², between about 2,500 g/m² and about 10,000 g/m², between about 2,500 g/m² and about 9,000 g/m², between about 2,500 g/m² and about 8,000 g/m², between about 2,500 g/m² and about 7,000 g/m², between about 2,500 g/m² and about 6,000 g/m², between about 2,500 g/m² and about 5,000 g/m², between about 2,500 g/m² and about 4,000 g/m², between about 2,500 g/m² and about 3,000 g/m², between about 3,000 g/m² and about 15,000 g/m², between about 3,000 g/m² and about 14,000 g/m², between about 3,000 g/m² and about 13,000 g/m², between about 3,000 g/m² and about 12,000 g/m², between about 3,000 g/m² and about 11,000 g/m², between about 3,000 g/m² and about 10,000 g/m², between about 3,000 g/m² and about 9,000 g/m², between about 3,000 g/m² and about 8,000 g/m², between about 3,000 g/m² and about 7,000 g/m², between about 3,000 g/m² and about 6,000 g/m², between about 3,000 g/m² and about 5,000 g/m², between about 3,000 g/m² and about 4,000 g/m², between about 4,000 g/m² and about 15,000 g/m², between about 4,000 g/m² and about 14,000 g/m², between about 4,000 g/m² and about 13,000 g/m², between about 4,000 g/m² and about 12,000 g/m², between about 4,000 g/m² and about 11,000 g/m², between about 4,000 g/m² and about 10,000 g/m², between about 4,000 g/m² and about 9,000 g/m², between about 4,000 g/m² and about 8,000 g/m², between about 4,000 g/m² and about 7,000 g/m², between about 4,000 g/m² and about 6,000 g/m², between about 4,000 g/m² and about 5,000 g/m², between about 5,000 g/m² and about 15,000 g/m², between about 5,000 g/m² and about 14,000 g/m², between about 5,000 g/m² and about 13,000 g/m², between about 5,000 g/m² and about 12,000 g/m², between about 5,000 g/m² and about 11,000 g/m², between about 5,000 g/m² and about 10,000 g/m², between about 5,000 g/m² and about 9,000 g/m², between about 5,000 g/m² and about 8,000 g/m², between about 5,000 g/m² and about 7,000 g/m², between about 5,000 g/m² and about 6,000 g/m², between about 6,000 g/m² and about 15,000 g/m², between about 6,000 g/m² and about 14,000 g/m², between about 6,000 g/m² and about 13,000 g/m², between about 6,000 g/m² and about 12,000 g/m², between about 6,000 g/m² and about 11,000 g/m², between about 6,000 g/m² and about 10,000 g/m², between about 6,000 g/m² and about 9,000 g/m², between about 6,000 g/m² and about 8,000 g/m², between about 6,000 g/m² and about 7,000 g/m², between about 7,000 g/m² and about 15,000 g/m², between about 7,000 g/m² and about 14,000 g/m², between about 7,000 g/m² and about 13,000 g/m², between about 7,000 g/m² and about 12,000 g/m², between about 7,000 g/m² and about 11,000 g/m², between about 7,000 g/m² and about 10,000 g/m², between about 7,000 g/m² and about 9,000 g/m², between about 7,000 g/m² and about 8,000 g/m², between about 8,000 g/m² and about 15,000 g/m², between about 8,000 g/m² and about 14,000 g/m², between about 8,000 g/m² and about 13,000 g/m², between about 8,000 g/m² and about 12,000 g/m², between about 8,000 g/m² and about 11,000 g/m², between about 8,000 g/m² and about 10,000 g/m², between about 8,000 g/m² and about 9,000 g/m², between about 9,000 g/m² and about 15,000 g/m², between about 9,000 g/m² and about 14,000 g/m², between about 9,000 g/m² and about 13,000 g/m², between about 9,000 g/m² and about 12,000 g/m², between about 9,000 g/m² and about 11,000 g/m², between about 9,000 g/m² and about 10,000 g/m², between about 10,000 g/m² and about 15,000 g/m², between about 10,000 g/m² and about 14,000 g/m², between about 10,000 g/m² and about 13,000 g/m², between about 10,000 g/m² and about 12,000 g/m², or between about 10,000 g/m² and about 11,000 g/m²) when a fluid including a recombinant antibody is flowed through the virus filter.

Also provided herein are methods of manufacturing a recombinant antibody or methods of purifying a recombinant antibody that include performing a unit operation of viral filtration (e.g., using any of the methods of performing viral filtration described herein). Non-limiting aspects of the methods of performing viral filtration and methods of manufacturing or purifying a recombinant antibody are described herein.

Recombinant Antibodies

Exemplary recombinant antibodies include an IgG, IgE, IgD, IgA, or IgM. A recombinant antibody can be any subclass of IgG, such as, e.g., IgG1, IgG2, IgG3, or IgG4, or a chimeric antibody (e.g., a IgG2/4 chimeric antibody, such as eculizumab). A recombinant antibody can be an antigen-binding antibody fragment, such as a Fab fragment, a F(ab')₂ fragment, or an scFv fragment. The recombinant antibody may be a bi-specific antibody or a tri-specific antibody, or a dimer, trimer, or multimer antibody, or a diabody, an AFFIBODY®, or a NANOBODY®. The recombinant antibody can be an engineered protein having four antibody binding domains such as DVD-Ig and CODV-Ig. See, e.g., US2007/0071675 and WO2012/135345. Non-limiting examples of recombinant antibodies are human or humanized antibodies.

Examples of recombinant antibodies can include one or both of: a heavy chain variable domain that includes a total of between one and six (e.g., one, two, three, four, five, or six) histidines in the set of CDR1, CDR2, and CDR3; and a light chain variable domain that includes a total of between one and six (e.g., one, two, three, four, five, or six) histidines in the set of CDR1, CDR2, and CDR3. In some examples, the recombinant antibody includes a heavy chain variable domain that includes a total of between one and six (e.g., one, two, three, four, five, or six) histidines in the set of CDR1, CDR2, and CDR3. In some examples, the heavy chain variable domain includes a CDR1 including one histidine residue and a CDR2 including one histidine residue. In some examples, the recombinant antibody includes one or more (e.g., one, two, or three) of a CDR1 including a sequence of SEQ ID NO: 1, a CDR2 including a sequence of SEQ ID NO: 2, and a CDR3 including a sequence of SEQ ID NO: 3. In some examples of any of the recombinant antibodies described herein, the heavy chain variable region includes a sequence of SEQ ID NO: 4. In some examples of any of the recombinant antibodies described herein, the heavy chain includes a sequence of SEQ ID NO: 5 (e.g., BNJ441 heavy chain). In some examples of any of the recombinant antibodies described herein, the light chain variable region includes one or more (e.g., one, two, or three) of a CDR1 including a sequence of SEQ ID NO: 6, a CDR2 including a sequence of SEQ ID NO: 7, and a CDR3 including a sequence of SEQ ID NO: 8. In some examples of any of the recombinant antibodies described herein, the light chain variable domain includes a sequence of SEQ ID NO: 9. In some examples of any of the recombinant antibodies described herein, the light chain includes a sequence of SEQ ID NO: 10 (e.g., BNJ441 light chain).

Examples of recombinant antibodies can include a heavy chain variable domain that includes one or more (e.g., one, two, or three) of a CDR1 including a sequence of SEQ ID NO: 11, a CDR2 including a sequence of SEQ ID NO: 12, and a CDR3 including a sequence of SEQ ID NO: 13. In some examples of any of the recombinant antibodies described herein, the recombinant antibody can include a heavy chain variable region including a sequence of SEQ ID NO: 14. In some examples of any of the recombinant antibodies described herein, the recombinant antibody can include a heavy chain including a sequence of SEQ ID NO: 15 (e.g., eculizumab heavy chain). In some examples of any of the recombinant antibodies described herein, the light chain variable region includes one or more (e.g., one, two, or three) of a CDR1 including a sequence of SEQ ID NO: 16, a CDR2 including a sequence of SEQ ID NO: 17, and a CDR3 including a sequence of SEQ ID NO: 18. In some examples of any of the recombinant antibodies described herein, the recombinant antibody can include a light chain variable region including a sequence of SEQ ID NO: 19. In some examples of any of the recombinant antibodies described herein, the recombinant antibody can include a light chain including a sequence of SEQ ID NO: 20 (e.g., eculizumab light chain).

Examples of recombinant antibodies can include a heavy chain variable domain that includes one or more (e.g., one, two, or three) of a CDR1 including a sequence of SEQ ID NO: 21, a CDR2 including a sequence of SEQ ID NO: 22, and a CDR3 including a sequence of SEQ ID NO: 23. In some examples of any of the recombinant antibodies described herein, the recombinant antibody can include a heavy chain variable region including a sequence of SEQ ID NO: 24. In some examples of any of the recombinant antibodies described herein, the recombinant antibody can include a heavy chain including a sequence of SEQ ID NO: 25 (e.g., BNJ383 heavy chain). In some examples of any of the recombinant antibodies described herein, the light chain variable region includes one or more (e.g., one, two, or three) of a CDR1 including a sequence of SEQ ID NO: 26, a CDR2 including a sequence of SEQ ID NO: 27, and a CDR3 including a sequence of SEQ ID NO: 28. In some examples of any of the recombinant antibodies described herein, the recombinant antibody can include a light chain variable region including a sequence of SEQ ID NO: 29. In some examples of any of the recombinant antibodies described herein, the recombinant antibody can include a light chain including a sequence of SEQ ID NO: 30 (e.g., BNJ383 light chain).

Examples of recombinant antibodies can include a heavy chain variable domain that includes one or more (e.g., one, two, or three) of a CDR1 including a sequence of SEQ ID NO: 31, a CDR2 including a sequence of SEQ ID NO: 32, and a CDR3 including a sequence of SEQ ID NO: 33. In some examples of any of the recombinant antibodies described herein, the recombinant antibody can include a heavy chain variable region including a sequence of SEQ ID NO: 34. In some examples of any of the recombinant antibodies described herein, the recombinant antibody can include a heavy chain including a sequence of SEQ ID NO: 35 (e.g., samalizumab heavy chain). In some examples of any of the recombinant antibodies described herein, the light chain variable region includes one or more (e.g., one, two, or three) of a CDR1 including a sequence of SEQ ID NO: 36, a CDR2 including a sequence of SEQ ID NO: 37, and a CDR3 including a sequence of SEQ ID NO: 38. In some examples of any of the recombinant antibodies described herein, the recombinant antibody can include a light chain variable region including a sequence of SEQ ID NO: 39. In some examples of any of the recombinant antibodies described herein, the recombinant antibody can include a light chain including a sequence of SEQ ID NO: 40 (e.g., samalizumab light chain).

Additional examples of recombinant antibodies include panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, amatuximab, anatumomab, anrukinzumab, apolizumab, arcitumomab, atinumab, tocilizumab, basilizimab, bectumomab, belimumab, bevacizumab, besilesomab, bezlotoxumab, biciromab, canakinumab, certolizumab, cetuximab, cixutumumab, daclizumab, denosumab, densumab, edrecolomab, efalizumab, efungumab, epratuzumab, ertumaxomab, etaracizumab, figitumumab, golimumab, ibritumomab tiuxetan, igovomab, imgatuzumab, infliximab, inolimomab, inotuzumab, labetuzumab, lebrikizumab, moxetumomab, natalizumab, obinutuzumab, oregovomab, palivizumab, panitumumab, pertuzumab, ranibizumab, rituximab, tocilizumab, tositumomab, tralokinumab, tucotuzumab, trastuzumab, veltuzumab, zalutumumab, and zatuximab. Additional examples of recombinant antibodies are known in the art.

Virus Filters

Virus filters can be a normal flow filter (NFF) or a tangential flow filtration (TFF) filter such as is described in, e.g., U.S. Pat. No. 6,365,395. In either TFF mode or NFF mode, filtration is conducted under conditions to retain the virus, e.g., a virus having a 20 to 100 nanometer (nm) diameter, on the membrane surface while permitting passage of the recombinant antibody through the membrane.

Exemplary virus filters include those formed from regenerated cellulose (e.g., cuprammonium-regenerated cellulose), polyethersulfone, polyarylsulphones, polysulfone, polyimide, polyamide, polyvinylidenedifluoride (PVDF) or the like. Non-limiting examples of virus filters include VIRESOLVE® membranes and RETROPORE™ membranes available from EMD Millipore, Billerica, MA These can be supplied in either a cartridge (NFF) form, such as VIRESOLVE® NFP viral filters, or as cassettes (for TFF), such as PELLICON® cassettes, available from EMD Millipore, Billerica, MA.

Additional exemplary virus filters that can be used in any of the methods described herein include Sartorius Virosart® CPV, which includes a polyethersulfone membrane. Other examples of a virus filter than can be used in any of the methods described herein is Asahi BioEx and Millipore Viresolve® Pro filter, which include a polyvinylidene fluoride (PVDF) membrane. In some examples, a virus filter can include a hollow fiber PVDF membrane. In some examples, the virus filter is an Asahi 20N filter, which includes a cuprammonium-regenerated cellulose membrane (e.g., a hollow fiber cuprammonium-regenerated cellulose membrane). Additional virus filters are known in the art.

Pre-Filters

Some embodiments of any of the methods described herein include flowing a fluid including a recombinant antibody through a pre-filter, e.g., before the fluid is flowed through a virus filter. Non-limiting examples of pre-filters include a Sartorius Virosart® Max pre-filter, a Millipore pre-filter, a Sartopore® 2 pre-filter, a Sartobind STIC® pre-filter, a Sartobind® Q pre-filter, a Sartobind® HIC Phenyl pre-filter, a Sartobind® S pre-filter, Millipore Viresolve® Pro Shield pre-filter, CUNO delipid pre-filter, and Millipore XOHC pre-filter. In some embodiments, a virus filter includes a polyamide membrane (e.g., a Sartorius Virosart® Max pre-filter), a cation exchange-based membrane, an anion exchange-based membrane, or a hydrophobic interaction chromatography (HIC)-based membrane. Additional examples of pre-filters are known in the art.

Stabilizing Agents

A stabilizing agent is an agent that reduces (e.g., a significant or detectable reduction) the hydrodynamic radius of a recombinant antibody in a fluid and/or minimizes the level of soluble and/or insoluble protein aggregates (e.g., soluble and/or insoluble recombinant antibody aggregates and/or soluble and/or insoluble host cell protein aggregates) in a fluid including a recombinant antibody. The hydrodynamic radius of a recombinant antibody in a fluid can be determined using methods well known in the art, e.g., dynamic light scattering. Methods for detecting the level or amount of soluble and insoluble protein aggregates are known in the art. For example, size exclusion chromatography, native (non-denaturing) gel chromatography, analytical ultracentrifugation (AUC), field-flow fractionation (FFF), and dynamic light scattering can be used to detect the amount of soluble or insoluble protein aggregates present in a fluid.

Non-limiting examples of stabilizing agents include arginine (e.g., L-arginine or L-arginine HCl), alanine (e.g., L-alanine), aspartic acid (e.g., L-aspartic acid), glutamic acid (e.g., L-glutamic acid), leucine (e.g., L-leucine), lysine (e.g., L-lysine), histidine (e.g., L-histidine), glycine (e.g., L-glycine), sucrose, trehalose, mannitol, sorbitol, and Polysorbate 80. When Polysorbate 80 is used as a stabilizing agent, it may be present in a fluid at a concentration of between about 0.005% v/v and about 0.05% v/v (e.g., between about 0.005% v/v and about 0.04%, between about 0.005% v/v and about 0.03% v/v, between about 0.005% v/v and about 0.02% v/v, between about 0.005% v/v and about 0.01% v/v, between about 0.01% v/v and about 0.05% v/v, between about 0.01% v/v and about 0.04% v/v, between about 0.01% v/v and about 0.03% v/v, between about 0.01% v/v and about 0.02% v/v, between about 0.02% v/v and about 0.05% v/v. between about 0.02% v/v and about 0.04% v/v, between about 0.02% v/v and about 0.03% v/v, between about 0.03% v/v and about 0.05% v/v, between about 0.03% v/v and about 0.04% v/v, or between about 0.04% v/v and about 0.05% v/v). Additional examples of stabilizing agents are known in the art.

Methods of Performing Viral Filtration (Part A)

Provided herein are methods of performing viral filtration that include: (a) adjusting (e.g., increasing or decreasing) the pH of a fluid including a recombinant antibody (e.g., any of the recombinant antibodies described herein) to between about 5.0 and about 6.7 (e.g., between about 5.0 and about 6.6, between about 5.0 and about 6.5, between about 5.0 and about 6.4, between about 5.0 and about 6.3, between about 5.0 and about 6.2, between about 5.0 and about 6.1, between about 5.0 and about 6.0, between about 5.0 and about 5.9, between about 5.0 and about 5.8, between about 5.0 and about 5.7, between about 5.0 and about 5.6, between about 5.0 and about 5.5, between about 5.0 and about 5.4, between about 5.0 and about 5.3, between about 5.0 and about 5.2, between about 5.1 and about 6.7, between about 5.1 and about 6.6, between about 5.1 and about 6.5, between about 5.1 and about 6.4, between about 5.1 and about 6.3, between about 5.1 and about 6.2, between about 5.1 and about 6.1, between about 5.1 and about 6.0, between about 5.1 and about 5.9, between about 5.1 and about 5.8, between about 5.1 and about 5.7, between about 5.1 and about 5.6, between about 5.1 and about 5.5, between about 5.1 and about 5.4, between about 5.1 and about 5.3, between about 5.2 and about 6.7, between about 5.2 and about 6.6, between about 5.2 and about 6.5, between about 5.2 and about 6.4, between about 5.2 and about 6.3, between about 5.2 and about 6.2, between about 5.2 and about 6.1, between about 5.2 and about 6.0, between about 5.2 and about 5.9, between about 5.2 and about 5.8, between about 5.2 and about 5.7, between about 5.2 and about 5.6, between about 5.2 and about 5.5, between about 5.2 and about 5.4, between about 5.3 and about 6.7, between about 5.3 and about 6.6, between about 5.3 and about 6.5, between about 5.3 and about 6.4, between about 5.3 and about 6.3, between about 5.3 and about 6.2, between about 5.3 and about 6.1, between about 5.3 and about 6.0, between about 5.3 and about 5.9, between about 5.3 and about 5.8, between about 5.3 and about 5.7, between about 5.3 and about 5.6, between about 5.3 and about 5.5, between about 5.4 and about 6.7, between about 5.4 and about 6.6, between about 5.4 and about 6.5, between about 5.4 and about 6.4, between about 5.4 and about 6.3, between about 5.4 and about 6.2, between about 5.4 and about 6.1, between about 5.4 and about 6.0, between about 5.4 and about 5.9, between about 5.4 and about 5.8, between about 5.4 and about 5.7, between about 5.4 and about 5.6, between about 5.5 and about 6.7, between about 5.5 and about 6.6, between about 5.5 and about 6.5, between about 5.5 and about 6.4, between about 5.5 and about 6.3, between about 5.5 and about 6.2, between about 5.5 and about 6.1, between about 5.5 and about 6.0, between about 5.5 and about 5.9, between about 5.5 and about 5.8, between about 5.5 and about 5.7, between about 5.6 and about 6.7, between about 5.6 and about 6.6, between about 5.6 and about 6.5, between about 5.6 and about 6.4, between about 5.6 and about 6.3, between about 5.6 and about 6.2, between about 5.6 and about 6.1, between about 5.6 and about 6.0, between about 5.6 and about 5.9, between about 5.6 and about 5.8, between about 5.7 and about 6.7, between about 5.7 and about 6.6, between about 5.7 and about 6.5, between about 5.7 and about 6.4, between about 5.7 and about 6.3, between about 5.7 and about 6.2, between about 5.7 and about 6.1, between about 5.7 and about 6.0, between about 5.7 and about 5.9, between about 5.8 and about 6.7, between about 5.8 and about 6.6, between about 5.8 and about 6.5, between about 5.8 and about 6.4, between about 5.8 and about 6.3, between about 5.8 and about 6.2, between about 5.8 and about 6.1, between about 5.8 and about 6.0, between about 5.9 and about 6.7, between about 5.9 and about 6.6, between about 5.9 and about 6.5, between about 5.9 and about 6.4, between about 5.9 and about 6.3, between about 5.9 and about 6.2, between about 5.9 and about 6.1, between about 6.0 and about 6.7, between about 6.0 and about 6.6, between about 6.0 and about 6.5, between about 6.0 and about 6.4, between about 6.0 and about 6.3, between about 6.0 and about 6.2, between about 6.1 and about 6.7, between about 6.1 and about 6.6, between about 6.1 and about 6.5, between about 6.1 and about 6.4, between about 6.1 and about 6.3, between about 6.2 and about 6.7, between about 6.2 and about 6.6, between about 6.2 and about 6.5, between about 6.2 and about 6.4, between about 6.3 and about 6.7, between about 6.3 and about 6.6, between about 6.3 and about 6.5, between about 6.4 and about 6.7, between about 6.4 and about 6.6, or between about 6.5 and about 6.7); and (b) flowing the fluid through a virus filter to produce a filtrate including the recombinant antibody. Some embodiments of these methods further include, prior to (b): adding a stabilizing agent (e.g., any of the stabilizing agents described herein) to the fluid in an amount sufficient to yield a final concentration of between about 0.1 mM and about 25 mM (e.g., between about 0.1 mM and about 24 mM, between about 0.1 mM and about 23 mM, between about 0.1 mM and about 22 mM, between about 0.1 mM and about 21 mM, between about 0.1 mM and about 20 mM, between about 0.1 mM and about 19 mM, between about 0.1 mM and about 18 mM, between about 0.1 mM and about 17 mM, between about 0.1 mM and about 16 mM, between about 0.1 mM and about 15 mM, between about 0.1 mM and about 14 mM, between about 0.1 mM and about 13 mM, between about 0.1 mM and about 12 mM, between about 0.1 mM and about 11 mM, between about 0.1 mM and about 10 mM, between about 0.1 mM and about 9 mM, between about 0.1 mM and about 8 mM, between about 0.1 mM and about 7 mM, between about 0.1 mM and about 6 mM, between about 0.1 mM and about 5 mM, between about 0.1 mM and about 4 mM, between about 0.1 mM and about 3 mM, between about 0.1 mM and about 2 mM, between about 0.5 mM and about 25 mM, between about 0.5 mM and about 24 mM, between about 0.5 mM and about 23 mM, between about 0.5 mM and about 22 mM, between about 0.5 mM and about 21 mM, between about 0.5 mM and about 20 mM, between about 0.5 mM and about 19 mM, between about 0.5 mM and about 18 mM, between about 0.5 mM and about 17 mM, between about 0.5 mM and about 16 mM, between about 0.5 mM and about 15 mM, between about 0.5 mM and about 14 mM, between about 0.5 mM and about 13 mM, between about 0.5 mM and about 12 mM, between about 0.5 mM and about 11 mM, between about 0.5 mM and about 10 mM, between about 0.5 mM and about 9 mM, between about 0.5 mM and about 8 mM, between about 0.5 mM and about 7 mM, between about 0.5 mM and about 6 mM, between about 0.5 mM and about 5 mM, between about 0.5 mM and about 4 mM, between about 0.5 mM and about 3 mM, between about 0.5 mM and about 2 mM, between about 1 mM and about 25 mM, between about 1 mM and about 24 mM, between about 1 mM and about 23 mM, between about 1 mM and about 22 mM, between about 1 mM and about 21 mM, between about 1 mM and about 20 mM, between about 1 mM and about 19 mM, between about 1 mM and about 18 mM, between about 1 mM and about 17 mM, between about 1 mM and about 16 mM, between about 1 mM and about 15 mM, between about 1 mM and about 14 mM, between about 1 mM and about 13 mM, between about 1 mM and about 12 mM, between about 1 mM and about 11 mM, between about 1 mM and about 10 mM, between about 1 mM and about 9 mM, between about 1 mM and about 8 mM, between about 1 mM and about 7 mM, between about 1 mM and about 6 mM, between about 1 mM and about 5 mM, between about 1 mM and about 4 mM, between about 1 mM and about 3 mM, between about 2.5 mM and about 25 mM, between about 2.5 mM and about 24 mM, between about 2.5 mM and about 23 mM, between about 2.5 mM and about 22 mM, between about 2.5 mM and about 21 mM, between about 2.5 mM and about 20 mM, between about 2.5 mM and about 19 mM, between about 2.5 mM and about 18 mM, between about 2.5 mM and about 17 mM, between about 2.5 mM and about 16 mM, between about 2.5 mM and about 15 mM, between about 2.5 mM and about 14 mM, between about 2.5 mM and about 13 mM, between about 2.5 mM and about 12 mM, between about 2.5 mM and about 11 mM, between about 2.5 mM and about 10 mM, between about 2.5 mM and about 9 mM, between about 2.5 mM and about 8 mM, between about 2.5 mM and about 7 mM, between about 2.5 mM and about 6 mM, between about 2.5 mM and about 5 mM, between about 5 mM and about 25 mM, between about 5 mM and about 24 mM, between about 5 mM and about 23 mM, between about 5 mM and about 22 mM, between about 5 mM and about 21 mM, between about 5 mM and about 20 mM, between about 5 mM and about 19 mM, between about 5 mM and about 18 mM, between about 5 mM and about 17 mM, between about 5 mM and about 16 mM, between about 5 mM and about 15 mM, between about 5 mM and about 14 mM, between about 5 mM and about 13 mM, between about 5 mM and about 12 mM, between about 5 mM and about 11 mM, between about 5 mM and about 10 mM, between about 5 mM and about 9 mM, between about 5 mM and about 8 mM, between about 5 mM and about 7 mM, between about 10 mM and about 25 mM, between about 10 mM and about 24 mM, between about 10 mM and about 23 mM, between about 10 mM and about 22 mM, between about 10 mM and about 21 mM, between about 10 mM and about 20 mM, between about 10 mM and about 19 mM, between about 10 mM and about 18 mM, between about 10 mM and about 17 mM, between about 10 mM and about 16 mM, between about 10 mM and about 15 mM, between about 10 mM and about 14 mM, between about 10 mM and about 13 mM, between about 10 mM and about 12 mM, between about 12.5 mM and about 25 mM, between about 12.5 mM and about 24 mM, between about 12.5 mM and about 23 mM, between about 12.5 mM and about 22 mM, between about 12.5 mM and about 21 mM, between about 12.5 mM and about 20 mM, between about 12.5 mM and about 19 mM, between about 12.5 mM and about 18 mM, between about 12.5 mM and about 17 mM, between about 12.5 mM and about 16 mM, between about 12.5 mM and about 15 mM, between about 15 mM and about 25 mM, between about 15 mM and about 24 mM, between about 15 mM and about 23 mM, between about 15 mM and about 22 mM, between about 15 mM and about 21 mM, between about 15 mM and about 20 mM, between about 15 mM and about 19 mM, between about 15 mM and about 18 mM, between about 15 mM and about 17 mM, between about 16 mM and about 25 mM, between about 16 mM and about 24 mM, between about 16 mM and about 23 mM, between about 16 mM and about 22 mM, between about 16 mM and about 21 mM, between about 16 mM and about 20 mM, between about 16 mM and about 19 mM, between about 16 mM and about 18 mM, between about 17 mM and about 25 mM, between about 17 mM and about 24 mM, between about 17 mM and about 23 mM, between about 17 mM and about 22 mM, between about 17 mM and about 21 mM, between about 17 mM and about 20 mM, between about 17 mM and about 19 mM, between about 18 mM and about 25 mM, between about 18 mM and about 24 mM, between about 18 mM and about 23 mM, between about 18 mM and about 22 mM, between about 18 mM and about 21 mM, between about 18 mM and about 20 mM, between about 19 mM and about 25 mM, between about 19 mM and about 24 mM, between about 19 mM and about 23 mM, between about 19 mM and about 22 mM, between about 19 mM and about 21 mM, between about 20 mM and about 25 mM, between about 20 mM and about 24 mM, between about 20 mM and about 23 mM, between about 20 mM and about 22 mM, between about 21 mM and about 25 mM, between about 21 mM and about 24 mM, between about 21 mM and about 23 mM, between about 22 mM and about 25 mM, between about 22 mM and about 24 mM, or between about 23 mM and about 25 mM) stabilizing agent in the fluid.

Some embodiments of these examples, further include, immediately prior to (b): flowing the fluid through a pre-filter (e.g., a pre-filter including a polyamide membrane, such as a Sartorius Virosart® Max pre-filter). In some embodiments of these examples, the fluid further includes between about 5 mM and about 300 mM sodium chloride (e.g., between about 5 mM and about 280 mM, between about 5 mM and about 260 mM, between about 5 mM and about 240 mM, between about 5 mM and about 220 mM, between about 5 mM and about 200 mM, between about 5 mM and about 180 mM, between about 5 mM and about 160 mM, between about 5 mM and about 140 mM, between about 5 mM and about 120 mM, between about 5 mM and about 100 mM, between about 5 mM and about 90 mM, between about 5 mM and about 80 mM, between about 5 mM and about 70 mM, between about 5 mM and about 60 mM, between about 5 mM and about 50 mM, between about 5 mM and about 40 mM, between about 5 mM and about 30 mM, between about 10 mM and about 300 mM, between about 10 mM and about 280 mM, between about 10 mM and about 260 mM, between about 10 mM and about 240 mM, between about 10 mM and about 220 mM, between about 10 mM and about 200 mM, between about 10 mM and about 180 mM, between about 10 mM and about 160 mM, between about 10 mM and about 140 mM, between about 10 mM and about 120 mM, between about 10 mM and about 100 mM, between about 10 mM and about 90 mM, between about 10 mM and about 80 mM, between about 10 mM and about 70 mM, between about 10 mM and about 60 mM, between about 10 mM and about 50 mM, between about 10 mM and about 40 mM, between about 20 mM and about 300 mM, between about 20 mM and about 280 mM, between about 20 mM and about 260 mM, between about 20 mM and about 240 mM, between about 20 mM and about 220 mM, between about 20 mM and about 200 mM, between about 20 mM and about 180 mM, between about 20 mM and about 160 mM, between about 20 mM and about 140 mM, between about 20 mM and about 120 mM, between about 20 mM and about 100 mM, between about 20 mM and about 90 mM, between about 20 mM and about 80 mM, between about 20 mM and about 70 mM, between about 20 mM and about 60 mM, between about 20 mM and about 50 mM, between about 30 mM and about 300 mM, between about 30 mM and about 280 mM, between about 30 mM and about 260 mM, between about 30 mM and about 240 mM, between about 30 mM and about 220 mM, between about 30 mM and about 200 mM, between about 30 mM and about 180 mM, between about 30 mM and about 160 mM, between about 30 mM and about 140 mM, between about 30 mM and about 120 mM, between about 30 mM and about 100 mM, between about 30 mM and about 90 mM, between about 30 mM and about 80 mM, between about 30 mM and about 70 mM, between about 30 mM and about 60 mM, between about 40 mM and about 300 mM, between about 40 mM and about 280 mM, between about 40 mM and about 260 mM, between about 40 mM and about 240 mM, between about 40 mM and about 220 mM, between about 40 mM and about 200 mM, between about 40 mM and about 180 mM, between about 40 mM and about 160 mM, between about 40 mM and about 140 mM, between about 40 mM and about 120 mM, between about 40 mM and about 100 mM, between about 40 mM and about 90 mM, between about 40 mM and about 80 mM, between about 40 mM and about 70 mM, between about 50 mM and about 300 mM, between about 50 mM and about 280 mM, between about 50 mM and about 260 mM, between about 50 mM and about 240 mM, between about 50 mM and about 220 mM, between about 50 mM and about 200 mM, between about 50 mM and about 180 mM, between about 50 mM and about 160 mM, between about 50 mM and about 140 mM, between about 50 mM and about 120 mM, between about 50 mM and about 100 mM, between about 50 mM and about 90 mM, between about 50 mM and about 80 mM, between about 75 mM and about 300 mM, between about 75 mM and about 280 mM, between about 75 mM and about 260 mM, between about 75 mM and about 240 mM, between about 75 mM and about 220 mM, between about 75 mM and about 200 mM, between about 75 mM and about 180 mM, between about 75 mM and about 160 mM, between about 75 mM and about 140 mM, between about 75 mM and about 120 mM, between about 75 mM and about 100 mM, between about 100 mM and about 300 mM, between about 100 mM and about 280 mM, between about 100 mM and about 260 mM, between about 100 mM and about 240 mM, between about 100 mM and about 220 mM, between about 100 mM and about 200 mM, between about 100 mM and about 180 mM, between about 100 mM and about 160 mM, between about 100 mM and about 140 mM, between about 100 mM and about 120 mM, between about 125 mM and about 300 mM, between about 125 mM and about 280 mM, between about 125 mM and about 260 mM, between about 125 mM and about 240 mM, between about 125 mM and about 220 mM, between about 125 mM and about 200 mM, between about 125 mM and about 180 mM, between about 125 mM and about 160 mM, between about 150 mM and about 300 mM, between about 150 mM and about 280 mM, between about 150 mM and about 260 mM, between about 150 mM and about 240 mM, between about 150 mM and about 220 mM, between about 150 mM and about 200 mM, between about 150 mM and about 180 mM, between about 175 mM and about 300 mM, between about 175 mM and about 280 mM, between about 175 mM and about 260 mM, between about 175 mM and about 240 mM, between about 175 mM and about 220 mM, between about 175 mM and about 200 mM, between about 200 mM and about 300 mM, between about 200 mM and about 280 mM, between about 200 mM and about 260 mM, between about 200 mM and about 240 mM, between about 200 mM and about 220 mM, between about 225 mM and about 300 mM, between about 225 mM and about 280 mM, between about 225 mM and about 260 mM, between about 250 mM and about 300 mM, between about 250 mM and about 280 mM, or between about 275 mM and about 300 mM sodium chloride). In some embodiments of any of these methods, the fluid includes between about 10 mM and about 50 mM (e.g., between about 10 mM and about 45 mM, between about 10 mM and about 40 mM, between about 10 mM and about 35 mM, between about 10 mM and about 30 mM, between about 10 mM and about 25 mM, between about 10 mM and about 20 mM, between about 15 mM and about 50 mM, between about 15 mM and about 45 mM, between about 15 mM and about 40 mM, between about 15 mM and about 35 mM, between about 15 mM and about 30 mM, between about 15 mM and about 25 mM, between about 20 mM and about 50 mM, between about 20 mM and about 45 mM, between about 20 mM and about 40 mM, between about 20 mM and about 35 mM, between about 20 mM and about 30 mM, between about 25 mM and about 50 mM, between about 25 mM and about 45 mM, between about 25 mM and about 40 mM, between about 25 mM and about 35 mM, between about 30 mM and about 50 mM, between about 30 mM and about 45 mM, between about 30 mM and about 40 mM, between about 35 mM and about 50 mM, between about 35 mM and about 45 mM, or between about 40 mM and about 50 mM) sodium phosphate.

In some embodiments of these methods, prior to step (a), the pH of the fluid is between about 7.4 and about 7.8 (e.g., between about 7.4 and about 7.7, between about 7.4 and about 7.6, between about 7.5 and about 7.8, between about 7.5 and about 7.7, between about 7.6 and about 7.8, or about 7.6).

Also provided are methods of performing viral filtration that include: (a) adding a stabilizing agent (e.g., any of the stabilizing agent described herein) to a fluid including a recombinant antibody in an amount sufficient to yield a final concentration of between about 10 mM and about 100 mM (e.g., between about 10 mM and about 95 mM, between about 10 mM and about 90 mM, between about 10 mM and about 85 mM, between about 10 mM and about 80 mM, between about 10 mM and about 75 mM, between about 10 mM and about 70 mM, between about 10 mM and about 65 mM, between about 10 mM and about 60 mM, between about 10 mM and about 55 mM, between about 10 mM and about 50 mM, between about 10 mM and about 45 mM, between about 10 mM and about 40 mM, between about 10 mM and about 35 mM, between about 10 mM and about 30 mM, between about 15 mM and about 100 mM, between about 15 mM and about 95 mM, between about 15 mM and about 90 mM, between about 15 mM and about 85 mM, between about 15 mM and about 80 mM, between about 15 mM and about 75 mM, between about 15 mM and about 70 mM, between about 15 mM and about 65 mM, between about 15 mM and about 60 mM, between about 15 mM and about 55 mM, between about 15 mM and about 50 mM, between about 15 mM and about 45 mM, between about 15 mM and about 40 mM, between about 15 mM and about 35 mM, between about 20 mM and about 100 mM, between about 20 mM and about 95 mM, between about 20 mM and about 90 mM, between about 20 mM and about 85 mM, between about 20 mM and about 80 mM, between about 20 mM and about 75 mM, between about 20 mM and about 70 mM, between about 20 mM and about 65 mM, between about 20 mM and about 60 mM, between about 25 mM and about 55 mM, between about 25 mM and about 50 mM, between about 25 mM and about 45 mM, between about 25 mM and about 30 mM and about 100 mM, between about 30 mM and about 95 mM, between about 30 mM and about 90 mM, between about 30 mM and about 85 mM, between about 30 mM and about 80 mM, between about 30 mM and about 75 mM, between about 30 mM and about 70 mM, between about 30 mM and about 65 mM, between about 30 mM and about 60 mM, between about 30 mM and about 55 mM, between about 30 mM and about 50 mM, between about 35 mM and about 100 mM, between about 35 mM and about 95 mM, between about 35 mM and about 90 mM, between about 35 mM and about 85 mM, between about 35 mM and about 80 mM, between about 35 mM and about 75 mM, between about 35 mM and about 70 mM, between about 35 mM and about 65 mM, between about 35 mM and about 60 mM, between about 35 mM and about 55 mM, between about 40 mM and about 100 mM, between about 40 mM and about 95 mM, between about 40 mM and about 90 mM, between about 40 mM and about 85 mM, between about 40 mM and about 80 mM, between about 40 mM and about 75 mM, between about 40 mM and about 70 mM, between about 40 mM and about 65 mM, between about 40 mM and about 60 mM, between about 45 mM and about 100 mM, between about 45 mM and about 95 mM, between about 45 mM and about 90 mM, between about 45 mM and about 85 mM, between about 45 mM and about 80 mM, between about 45 mM and about 75 mM, between about 45 mM and about 70 mM, between about 45 mM and about 65 mM, between about 50 mM and about 100 mM, between about 50 mM and about 95 mM, between about 50 mM and about 90 mM, between about 50 mM and about 85 mM, between about 50 mM and about 80 mM, between about 50 mM and about 75 mM, between about 50 mM and about 70 mM, between about 55 mM and about 100 mM, between about 55 mM and about 95 mM, between about 55 mM and about 90 mM, between about 55 mM and about 85 mM, between about 55 mM and about 80 mM, between about 55 mM and about 75 mM, between about 60 mM and about 100 mM, between about 60 mM and about 95 mM, between about 60 mM and about 90 mM, between about 60 mM and about 85 mM, between about 60 mM and about 80 mM, between about 65 mM and about 100 mM, between about 65 mM and about 95 mM, between about 65 mM and about 90 mM, between about 65 mM and about 85 mM, between about 70 mM and about 100 mM, between about 70 mM and about 95 mM, between about 70 mM and about 90 mM, between about 75 mM and about 100 mM, between about 75 mM and about 95 mM, or between about 80 mM and about 100 mM) stabilizing agent in the fluid, wherein prior to adding, the fluid has a pH of between about 6.7 and about 8.5 (between about 6.7 and about 8.4, between about 6.7 and about 8.3, between about 6.7 and about 8.2, between about 6.7 and about 8.1, between about 6.7 and about 8.0, between about 6.7 and about 7.9, between about 6.7 and about 7.8, between about 6.7 and about 7.7, between about 6.7 and about 7.6, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.8 and about 8.5, between about 6.8 and about 8.4, between about 6.8 and about 8.3, between about 6.8 and about 8.2, between about 6.8 and about 8.1, between about 6.8 and about 8.0, between about 6.8 and about 7.9, between about 6.8 and about 7.8, between about 6.8 and about 7.7, between about 6.8 and about 7.6, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.9 and about 8.5, between about 6.9 and about 8.4, between about 6.9 and about 8.3, between about 6.9 and about 8.2, between about 6.9 and about 8.1, between about 6.9 and about 8.0, between about 6.9 and about 7.9, between about 6.9 and about 7.8, between about 6.9 and about 7.7, between about 6.9 and about 7.6, between about 6.9 and about 7.5, between about 6.9 and about 7.4, between about 6.9 and about 7.3, between about 6.9 and about 7.2, between about 6.9 and about 7.1, between about 7.0 and about 8.5, between about 7.0 and about 8.4, between about 7.0 and about 8.3, between about 7.0 and about 8.2, between about 7.0 and about 8.1, between about 7.0 and about 8.0, between about 7.0 and about 7.9, between about 7.0 and about 7.8, between about 7.0 and about 7.7, between about 7.0 and about 7.6, between about 7.0 and about 7.5, between about 7.0 and about 7.4, between about 7.0 and about 7.3, between about 7.0 and about 7.2, between about 7.1 and about 8.5, between about 7.1 and about 8.4, between about 7.1 and about 8.3, between about 7.1 and about 8.2, between about 7.1 and about 8.1, between about 7.1 and about 8.0, between about 7.1 and about 7.9, between about 7.1 and about 7.8, between about 7.1 and about 7.7, between about 7.1 and about 7.6, between about 7.1 and about 7.5, between about 7.1 and about 7.4, between about 7.1 and about 7.3, between about 7.2 and about 8.5, between about 7.2 and about 8.4, between about 7.2 and about 8.3, between about 7.2 and about 8.2, between about 7.2 and about 8.1, between about 7.2 and about 8.0, between about 7.2 and about 7.9, between about 7.2 and about 7.8, between about 7.2 and about 7.7, between about 7.2 and about 7.6, between about 7.2 and about 7.5, between about 7.2 and about 7.4, between about 7.3 and about 8.5, between about 7.3 and about 8.4, between about 7.3 and about 8.3, between about 7.3 and about 8.2, between about 7.3 and about 8.1, between about 7.3 and about 8.0, between about 7.3 and about 7.9, between about 7.3 and about 7.8, between about 7.3 and about 7.7, between about 7.3 and about 7.6, between about 7.3 and about 7.5, between about 7.4 and about 8.5, between about 7.4 and about 8.4, between about 7.4 and about 8.3, between about 7.4 and about 8.2, between about 7.4 and about 8.1, between about 7.4 and about 8.0, between about 7.4 and about 7.9, between about 7.4 and about 7.8, between about 7.4 and about 7.7, between about 7.4 and about 7.6, between about 7.5 and about 8.5, between about 7.5 and about 8.4, between about 7.5 and about 8.3, between about 7.5 and about 8.2, between about 7.5 and about 8.1, between about 7.5 and about 8.0, between about 7.5 and about 7.9, between about 7.5 and about 7.8, between about 7.5 and about 7.7, between about 7.6 and about 8.5, between about 7.6 and about 8.4, between about 7.6 and about 8.3, between about 7.6 and about 8.2, between about 7.6 and about 8.1, between about 7.6 and about 8.0, between about 7.6 and about 7.9, between about 7.6 and about 7.8, between about 7.7 and about 8.5, between about 7.7 and about 8.4, between about 7.7 and about 8.3, between about 7.7 and about 8.2, between about 7.7 and about 8.1, between about 7.7 and about 8.0, between about 7.7 and about 7.9, between about 7.8 and about 8.5, between about 7.8 and about 8.4, between about 7.8 and about 8.3, between about 7.8 and about 8.2, between about 7.8 and about 8.1, between about 7.8 and about 8.0, between about 7.9 and about 8.5, between about 7.9 and about 8.4, between about 7.9 and about 8.3, between about 7.9 and about 8.2, between about 7.9 and about 8.1, between about 8.0 and about 8.5, between about 8.0 and about 8.4, between about 8.0 and about 8.3, between about 8.0 and about 8.2, between about 8.1 and about 8.5, between about 8.1 and about 8.4, between about 8.1 and about 8.3, between about 8.2 and about 8.5, between about 8.2 and about 8.4, or between about 8.3 and about 8.5); and (b) flowing the fluid through a virus filter to produce a filtrate including the recombinant antibody. Some embodiments of these methods further include, immediately prior to step (b), flowing the fluid through a pre-filter (e.g., any of the pre-filters described herein, such as a pre-filter including a polyamide membrane, such as a Sartorius Virosart® Max pre-filter). In some embodiments of these methods, the fluid includes between about 1 mM and about 100 mM sodium chloride (e.g., between about 1 mM and about 90 mM, between about 1 mM and about 80 mM, between about 1 mM and about 70 mM, between about 1 mM and about 60 mM, between about 1 mM and about 50 mM, between about 1 mM and about 40 mM, between about 1 mM and about 30 mM, between about 1 mM and about 20 mM, between about 10 mM and about 100 mM, between about 10 mM and about 90 mM, between about 10 mM and about 80 mM, between about 10 mM and about 70 mM, between about 10 mM and about 60 mM, between about 10 mM and about 50 mM, between about 10 mM and about 40 mM, between about 10 mM and about 30 mM, between about 20 mM and about 100 mM, between about 20 mM and about 90 mM, between about 20 mM and about 80 mM, between about 20 mM and about 70 mM, between about 20 mM and about 60 mM, between about 20 mM and about 50 mM, between about 20 mM and about 40 mM, between about 30 mM and about 100 mM, between about 30 mM and about 90 mM, between about 30 mM and about 80 mM, between about 30 mM and about 70 mM, between about 30 mM and about 60 mM, between about 30 mM and about 50 mM, between about 40 mM and about 100 mM, between about 40 mM and about 90 mM, between about 40 mM and about 80 mM, between about 40 mM and about 70 mM, between about 40 mM and about 60 mM, between about 50 mM and about 100 mM, between about 50 mM and about 90 mM, between about 50 mM and about 80 mM, between about 50 mM and about 70 mM, between about 60 mM and about 100 mM, between about 60 mM and about 90 mM, between about 60 mM and about 80 mM, between about 70 mM and about 100 mM, between about 70 mM and about 90 mM, or between about 80 mM and about 100 mM sodium chloride).

In any of the methods of performing viral filtration described herein, wherein prior to (a), the fluid includes between about 0.1 mg/mL and about 25 mg/mL (e.g., between about 0.1 mg/mL and about 20 mg/mL, between about 0.1 mg/mL and about 24 mg/mL, between about 0.1 mg/mL and about 22 mg/mL, between about 0.1 mg/mL and about 20 mg/mL, between about 0.1 mg/mL and about 18 mg/mL, between about 0.1 mg/mL and about 16 mg/mL, between about 0.1 mg/mL and about 14 mg/mL, between about 0.1 mg/mL and about 12 mg/mL, between about 0.1 mg/mL and about 10 mg/mL, between about 0.1 mg/mL and about 8 mg/mL, between about 0.1 mg/mL and about 6 mg/mL, between about 0.1 mg/mL and about 4 mg/mL, between about 0.1 mg/mL and about 2 mg/mL, between about 0.5 mg/mL and about 25 mg/mL, between about 0.5 mg/mL and about 24 mg/mL, between about 0.5 mg/mL and about 22 mg/mL, between about 0.5 mg/mL and about 20 mg/mL, between about 0.5 mg/mL and about 18 mg/mL, between about 0.5 mg/mL and about 16 mg/mL, between about 0.5 mg/mL and about 14 mg/mL, between about 0.5 mg/mL and about 12 mg/mL, between about 0.5 mg/mL and about 10 mg/mL, between about 0.5 mg/mL and about 8 mg/mL, between about 0.5 mg/mL and about 6 mg/mL, between about 0.5 mg/mL and about 4 mg/mL, between about 0.5 mg/mL and about 2 mg/mL, between about 1 mg/mL and about 25 mg/mL, between about 1 mg/mL and about 24 mg/mL, between about 1 mg/mL and about 22 mg/mL, between about 1 mg/mL and about 20 mg/mL, between about 1 mg/mL and about 18 mg/mL, between about 1 mg/mL and about 16 mg/mL, between about 1 mg/mL and about 14 mg/mL, between about 1 mg/mL and about 12 mg/mL, between about 1 mg/mL and about 10 mg/mL, between about 1 mg/mL and about 8 mg/mL, between about 1 mg/mL and about 6 mg/mL, between about 1 mg/mL and about 4 mg/mL, between about 2 mg/mL and about 25 mg/mL, between about 2 mg/mL and about 24 mg/mL, between about 2 mg/mL and about 22 mg/mL, between about 2 mg/mL and about 20 mg/mL, between about 2 mg/mL and about 18 mg/mL, between about 2 mg/mL and about 16 mg/mL, between about 2 mg/mL and about 14 mg/mL, between about 2 mg/mL and about 12 mg/mL, between about 2 mg/mL and about 10 mg/mL, between about 2 mg/mL and about 8 mg/mL, between about 2 mg/mL and about 6 mg/mL, between about 2 mg/mL and about 4 mg/mL, between about 4 mg/mL and about 25 mg/mL, between about 4 mg/mL and about 24 mg/mL, between about 4 mg/mL and about 22 mg/mL, between about 4 mg/mL and about 20 mg/mL, between about 4 mg/mL and about 18 mg/mL, between about 4 mg/mL and about 16 mg/mL, between about 4 mg/mL and about 14 mg/mL, between about 4 mg/mL and about 12 mg/mL, between about 4 mg/mL and about 10 mg/mL, between about 4 mg/mL and about 8 mg/mL, between about 4 mg/mL and about 6 mg/mL, between about 6 mg/mL and about 25 mg/mL, between about 6 mg/mL and about 24 mg/mL, between about 6 mg/mL and about 22 mg/mL, between about 6 mg/mL and about 20 mg/mL, between about 6 mg/mL and about 18 mg/mL, between about 6 mg/mL and about 16 mg/mL, between about 6 mg/mL and about 14 mg/mL, between about 6 mg/mL and about 12 mg/mL, between about 6 mg/mL and about 10 mg/mL, between about 6 mg/mL and about 8 mg/mL, between about 8 mg/mL and about 25 mg/mL, between about 8 mg/mL and about 24 mg/mL, between about 8 mg/mL and about 22 mg/mL, between about 8 mg/mL and about 20 mg/mL, between about 8 mg/mL and about 18 mg/mL, between about 8 mg/mL and about 16 mg/mL, between about 8 mg/mL and about 14 mg/mL, between about 8 mg/mL and about 12 mg/mL, between about 8 mg/mL and about 10 mg/mL, between about 10 mg/mL and about 25 mg/mL, between about 10 mg/mL and about 24 mg/mL, between about 10 mg/mL and about 22 mg/mL, between about 10 mg/mL and about 20 mg/mL, between about 10 mg/mL and about 18 mg/mL, between about 10 mg/mL and about 16 mg/mL, between about 10 mg/mL and about 14 mg/mL, between about 10 mg/mL and about 12 mg/mL, between about 12 mg/mL and about 25 mg/mL, between about 12 mg/mL and about 24 mg/mL, between about 12 mg/mL and about 22 mg/mL, between about 12 mg/mL and about 20 mg/mL, between about 12 mg/mL and about 18 mg/mL, between about 12 mg/mL and about 16 mg/mL, between about 12 mg/mL and about 14 mg/mL, between about 14 mg/mL and about 25 mg/mL, between about 14 mg/mL and about 24 mg/mL, between about 14 mg/mL and about 22 mg/mL, between about 14 mg/mL and about 20 mg/mL, between about 14 mg/mL and about 18 mg/mL, between about 14 mg/mL and about 16 mg/mL, between about 16 mg/mL and about 25 mg/mL, between about 16 mg/mL and about 24 mg/mL, between about 16 mg/mL and about 22 mg/mL, between about 16 mg/mL and about 20 mg/mL, between about 16 mg/mL and about 18 mg/mL, between about 18 mg/mL and about 25 mg/mL, between about 18 mg/mL and about 24 mg/mL, between about 18 mg/mL and about 22 mg/mL, between about 18 mg/mL and about 20 mg/mL, between about 20 mg/mL and about 25 mg/mL, between about 20 mg/mL and about 24 mg/mL, between about 20 mg/mL and about 22 mg/mL, between about 22 mg/mL and about 25 mg/mL, between about 22 mg/mL and about 24 mg/mL, or between about 23 mg/mL and about 25 mg/mL) recombinant antibody. In some embodiments of these methods, the fluid has a pH of between about 7.4 and about 7.8 (e.g., between about 7.4 and about 7.7, between about 7.4 and about 7.6, between about 7.5 and about 7.8, between about 7.5 and about 7.7, between about 7.6 and about 7.8, or about 7.6).

In some embodiments of any of these methods, the fluid includes between about 50 mM and about 90 mM sodium chloride (e.g., between about 50 mM and about 80 mM, between 50 mM and about 75 mM, between about 50 mM and about 70 mM, between about 50 mM and about 65 mM, between about 50 mM and about 60 mM, between about 50 mM and about 55 mM, between about 55 mM and about 90 mM, between about 55 mM and about 85 mM, between about 55 mM and about 80 mM, between about 55 mM and about 75 mM, between about 55 mM and about 70 mM, between about 55 mM and about 65 mM, between about 55 mM and about 60 mM, between about 60 mM and about 90 mM, between about 60 mM and about 85 mM, between about 60 mM and about 80 mM, between about 60 mM and about 75 mM, between about 60 mM and about 70 mM, between about 60 mM and about 65 mM, between about 65 mM and about 90 mM, between about 65 mM and about 85 mM, between about 65 mM and about 80 mM, between about 65 mM and about 75 mM, between about 65 mM and about 70 mM, between about 70 mM and about 90 mM, between about 70 mM and about 85 mM, between about 70 mM and about 80 mM, between about 70 mM and about 75 mM, between about 75 mM and about 90 mM, between about 75 mM and about 85 mM, between about 75 mM and about 80 mM, between about 80 mM and about 90 mM, between about 80 mM and about 85 mM, or between about 85 mM and about 90 mM sodium chloride).

In some embodiments of the methods described in this section, the recombinant antibodies can include one or both of: a heavy chain variable domain that includes a total of between one and six (e.g., one, two, three, four, five, or six) histidines in the set of CDR1, CDR2, and CDR3; and a light chain variable domain that includes a total of between one and six (e.g., one, two, three, four, five, or six) histidines in the set of CDR1, CDR2, and CDR3. In some examples of the methods described in this section, the recombinant antibody includes a heavy chain variable domain that includes a total of between one and six (e.g., one, two, three, four, five, or six) histidines in the set of CDR1, CDR2, and CDR3. In some examples of the methods described in this section, the heavy chain variable domain includes a CDR1 including one histidine residue and a CDR2 including one histidine residue. In some examples of the methods described in this section, the recombinant antibody includes one or more (e.g., one, two, or three) of a CDR1 including a sequence of SEQ ID NO: 1, a CDR2 including a sequence of SEQ ID NO: 2, and a CDR3 including a sequence of SEQ ID NO: 3. In some examples of any the methods described in this section, the heavy chain variable region includes a sequence of SEQ ID NO: 4. In some examples of the methods described in this section, the heavy chain includes a sequence of SEQ ID NO: 5 (BNJ441 heavy chain). In some examples of any of the methods described in this section, the light chain variable region includes one or more (e.g., one, two, or three) of a CDR1 including a sequence of SEQ ID NO: 6, a CDR2 including a sequence of SEQ ID NO: 7, and a CDR3 including a sequence of SEQ ID NO: 8. In some examples of the methods described in this section, the light chain variable domain includes a sequence of SEQ ID NO: 9. In some examples of the methods described in this section, the light chain includes a sequence of SEQ ID NO: 10 (BNJ441 light chain).

In some examples of the methods described in this section, the recombinant antibody can include a heavy chain variable domain that includes one or more (e.g., one, two, or three) of a CDR1 including a sequence of SEQ ID NO: 11, a CDR2 including a sequence of SEQ ID NO: 12, and a CDR3 including a sequence of SEQ ID NO: 13. In some examples of the methods described in this section, the recombinant antibody can include a heavy chain variable region including a sequence of SEQ ID NO: 14. In some examples of any of the methods described in this section, the recombinant antibody can include a heavy chain including a sequence of SEQ ID NO: 15 (eculizumab heavy chain). In some examples of any of the methods described in this section, the light chain variable region includes one or more (e.g., one, two, or three) of a CDR1 including a sequence of SEQ ID NO: 16, a CDR2 including a sequence of SEQ ID NO: 17, and a CDR3 including a sequence of SEQ ID NO: 18. In some examples of any of the methods described herein, the recombinant antibody can include a light chain variable region including a sequence of SEQ ID NO: 19. In some examples of any of the methods described herein, the recombinant antibody can include a light chain including a sequence of SEQ ID NO: 20 (eculizumab light chain).

Methods of Performing Viral Filtration (Part B)

Also provided are methods of performing viral filtration that include: (a) flowing a fluid including a recombinant antibody (e.g., any of the recombinant antibodies described herein) through a pre-filter (e.g., any of the pre-filters described herein) to provide a first filtrate including the recombinant antibody; and (b) flowing the first filtrate through a virus filter (e.g., any of the virus filters described herein) to produce a second filtrate including the recombinant antibody. Some embodiments further include, prior to step (a): adding a stabilizing agent (e.g., any of the stabilizing agent described herein) to a fluid including the recombinant antibody in an amount sufficient to yield a final concentration of between about 1 mM and about 100 mM (e.g., between about 1 mM and about 95 mM, between about 1 mM and about 90 mM, between about 1 mM and about 85 mM, between about 1 mM and about 80 mM, between about 1 mM and about 75 mM, between about 1 mM and about 70 mM, between about 1 mM and about 65 mM, between about 1 mM and about 60 mM, between about 1 mM and about 55 mM, between about 1 mM and about 50 mM, between about 1 mM and about 45 mM, between about 1 mM and about 40 mM, between about 1 mM and about 35 mM, between about 1 mM and about 30 mM, between about 1 mM and about 25 mM, between about 1 mM and about 20 mM, between about 1 mM and about 15 mM, between about 1 mM and about 10 mM, between about 10 mM and about 100 mM, between about 10 mM and about 95 mM, between about 10 mM and about 90 mM, between about 10 mM and about 85 mM, between about 10 mM and about 80 mM, between about 10 mM and about 75 mM, between about 10 mM and about 70 mM, between about 10 mM and about 65 mM, between about 10 mM and about 60 mM, between about 10 mM and about 55 mM, between about 10 mM and about 50 mM, between about 10 mM and about 45 mM, between about 10 mM and about 40 mM, between about 10 mM and about 35 mM, between about 10 mM and about 30 mM, between about 15 mM and about 100 mM, between about 15 mM and about 95 mM, between about 15 mM and about 90 mM, between about 15 mM and about 85 mM, between about 15 mM and about 80 mM, between about 15 mM and about 75 mM, between about 15 mM and about 70 mM, between about 15 mM and about 65 mM, between about 15 mM and about 60 mM, between about 15 mM and about 55 mM, between about 15 mM and about 50 mM, between about 15 mM and about 45 mM, between about 15 mM and about 40 mM, between about 15 mM and about 35 mM, between about 20 mM and about 100 mM, between about 20 mM and about 95 mM, between about 20 mM and about 90 mM, between about 20 mM and about 85 mM, between about 20 mM and about 80 mM, between about 20 mM and about 75 mM, between about 20 mM and about 70 mM, between about 20 mM and about 65 mM, between about 20 mM and about 60 mM, between about 25 mM and about 55 mM, between about 25 mM and about 50 mM, between about 25 mM and about 45 mM, between about 30 mM and about 100 mM, between about 30 mM and about 95 mM, between about 30 mM and about 90 mM, between about 30 mM and about 85 mM, between about 30 mM and about 80 mM, between about 30 mM and about 75 mM, between about 30 mM and about 70 mM, between about 30 mM and about 65 mM, between about 30 mM and about 60 mM, between about 30 mM and about 55 mM, between about 30 mM and about 50 mM, between about 35 mM and about 100 mM, between about 35 mM and about 95 mM, between about 35 mM and about 90 mM, between about 35 mM and about 85 mM, between about 35 mM and about 80 mM, between about 35 mM and about 75 mM, between about 35 mM and about 70 mM, between about 35 mM and about 65 mM, between about 35 mM and about 60 mM, between about 35 mM and about 55 mM, between about 40 mM and about 100 mM, between about 40 mM and about 95 mM, between about 40 mM and about 90 mM, between about 40 mM and about 85 mM, between about 40 mM and about 80 mM, between about 40 mM and about 75 mM, between about 40 mM and about 70 mM, between about 40 mM and about 65 mM, between about 40 mM and about 60 mM, between about 45 mM and about 100 mM, between about 45 mM and about 95 mM, between about 45 mM and about 90 mM, between about 45 mM and about 85 mM, between about 45 mM and about 80 mM, between about 45 mM and about 75 mM, between about 45 mM and about 70 mM, between about 45 mM and about 65 mM, between about 50 mM and about 100 mM, between about 50 mM and about 95 mM, between about 50 mM and about 90 mM, between about 50 mM and about 85 mM, between about 50 mM and about 80 mM, between about 50 mM and about 75 mM, between about 50 mM and about 70 mM, between about 55 mM and about 100 mM, between about 55 mM and about 95 mM, between about 55 mM and about 90 mM, between about 55 mM and about 85 mM, between about 55 mM and about 80 mM, between about 55 mM and about 75 mM, between about 60 mM and about 100 mM, between about 60 mM and about 95 mM, between about 60 mM and about 90 mM, between about 60 mM and about 85 mM, between about 60 mM and about 80 mM, between about 65 mM and about 100 mM, between about 65 mM and about 95 mM, between about 65 mM and about 90 mM, between about 65 mM and about 85 mM, between about 70 mM and about 100 mM, between about 70 mM and about 95 mM, between about 70 mM and about 90 mM, between about 75 mM and about 100 mM, between about 75 mM and about 95 mM, or between about 80 mM and about 100 mM) stabilizing agent in the fluid.

In some embodiments of these methods, prior to step (a), the pH of the fluid is between about 7.4 and about 7.8 (e.g., between about 7.4 and about 7.7, between about 7.4 and about 7.6, between about 7.5 and about 7.8, between about 7.5 and about 7.7, between about 7.6 and about 7.8, or about 7.6). In some embodiments of any of these methods, the fluid includes between about 10 mM and about 50 mM (e.g., between about 10 mM and about 45 mM, between about 10 mM and about 40 mM, between about 10 mM and about 35 mM, between about 10 mM and about 30 mM, between about 10 mM and about 25 mM, between about 10 mM and about 20 mM, between about 15 mM and about 50 mM, between about 15 mM and about 45 mM, between about 15 mM and about 40 mM, between about 15 mM and about 35 mM, between about 15 mM and about 30 mM, between about 15 mM and about 25 mM, between about 20 mM and about 50 mM, between about 20 mM and about 45 mM, between about 20 mM and about 40 mM, between about 20 mM and about 35 mM, between about 20 mM and about 30 mM, between about 25 mM and about 50 mM, between about 25 mM and about 45 mM, between about 25 mM and about 40 mM, between about 25 mM and about 35 mM, between about 30 mM and about 50 mM, between about 30 mM and about 45 mM, between about 30 mM and about 40 mM, between about 35 mM and about 50 mM, between about 35 mM and about 45 mM, or between about 40 mM and about 50 mM) sodium phosphate.

In some embodiments of these methods, the fluid includes between about 50 mM and about 90 mM sodium chloride (e.g., between about 50 mM and about 80 mM, between 50 mM and about 75 mM, between about 50 mM and about 70 mM, between about 50 mM and about 65 mM, between about 50 mM and about 60 mM, between about 50 mM and about 55 mM, between about 55 mM and about 90 mM, between about 55 mM and about 85 mM, between about 55 mM and about 80 mM, between about 55 mM and about 75 mM, between about 55 mM and about 70 mM, between about 55 mM and about 65 mM, between about 55 mM and about 60 mM, between about 60 mM and about 90 mM, between about 60 mM and about 85 mM, between about 60 mM and about 80 mM, between about 60 mM and about 75 mM, between about 60 mM and about 70 mM, between about 60 mM and about 65 mM, between about 65 mM and about 90 mM, between about 65 mM and about 85 mM, between about 65 mM and about 80 mM, between about 65 mM and about 75 mM, between about 65 mM and about 70 mM, between about 70 mM and about 90 mM, between about 70 mM and about 85 mM, between about 70 mM and about 80 mM, between about 70 mM and about 75 mM, between about 75 mM and about 90 mM, between about 75 mM and about 85 mM, between about 75 mM and about 80 mM, between about 80 mM and about 90 mM, between about 80 mM and about 85 mM, or between about 85 mM and about 90 mM sodium chloride).

The recombinant antibody in any of the methods described in this section can be any of the recombinant antibodies described herein. For example, the recombinant antibodies can include one or both of: a heavy chain variable domain that includes a total of between one and six (e.g., one, two, three, four, five, or six) histidines in the set of CDR1, CDR2, and CDR3; and a light chain variable domain that includes a total of between one and six (e.g., one, two, three, four, five, or six) histidines in the set of CDR1, CDR2, and CDR3. The heavy chain variable domain e.g., can include a total of between one and six (e.g., one, two, three, four, five, or six) histidines in the set of CDR1, CDR2, and CDR3. In some examples of the methods described in this section, the heavy chain variable domain can include a CDR1 including one histidine residue and a CDR2 including one histidine residue. In some examples of the methods described in this section, the recombinant antibody includes one or more (e.g., one, two, or three) of a CDR1 including a sequence of SEQ ID NO: 1, a CDR2 including a sequence of SEQ ID NO: 2, and a CDR3 including a sequence of SEQ ID NO: 3. In some examples of any the methods described in this section, the heavy chain variable region includes a sequence of SEQ ID NO: 4. In some examples of the methods described in this section, the heavy chain includes a sequence of SEQ ID NO: 5 (BNJ441 heavy chain). In some examples of any of the methods described in this section, the light chain variable region includes one or more (e.g., one, two, or three) of a CDR1 including a sequence of SEQ ID NO: 6, a CDR2 including a sequence of SEQ ID NO: 7, and a CDR3 including a sequence of SEQ ID NO: 8. In some examples of the methods described in this section, the light chain variable domain includes a sequence of SEQ ID NO: 9. In some examples of the methods described in this section, the light chain includes a sequence of SEQ ID NO: 10 (BNJ441 light chain).

In some examples of the methods described in this section, the recombinant antibody can include a heavy chain variable domain that includes one or more (e.g., one, two, or three) of a CDR1 including a sequence of SEQ ID NO: 11, a CDR2 including a sequence of SEQ ID NO: 12, and a CDR3 including a sequence of SEQ ID NO: 13. In some examples of the methods described in this section, the recombinant antibody can include a heavy chain variable region including a sequence of SEQ ID NO: 14. In some examples of any of the methods described in this section, the recombinant antibody can include a heavy chain including a sequence of SEQ ID NO: 15 (eculizumab heavy chain). In some examples of any of the methods described in this section, the light chain variable region includes one or more (e.g., one, two, or three) of a CDR1 including a sequence of SEQ ID NO: 16, a CDR2 including a sequence of SEQ ID NO: 17, and a CDR3 including a sequence of SEQ ID NO: 18. In some examples of any of the methods described herein, the recombinant antibody can include a light chain variable region including a sequence of SEQ ID NO: 19. In some examples of any of the methods described herein, the recombinant antibody can include a light chain including a sequence of SEQ ID NO: 20 (eculizumab light chain).

Methods of Performing Viral Filtration (Part C)

Also provided are methods of performing viral filtration that include: (a) adjusting (e.g., increasing or decreasing) the pH of a fluid including a recombinant antibody (e.g., any of the recombinant antibodies described herein) to between about 7.0 and about 7.85 (e.g., between about 7.0 and about 7.8, between about 7.0 and about 7.75, between about 7.0 and about 7.7, between about 7.0 and about 7.65, between about 7.0 and about 7.6, between about 7.0 and about 7.55, between about 7.0 and about 7.5, between about 7.0 and about 7.45, between about 7.0 and about 7.4, between about 7.0 and about 7.35, between about 7.0 and about 7.3, between about 7.0 and about 7.25, between about 7.0 and about 7.2, between about 7.0 and about 7.15, between about 7.0 and about 7.1, between about 7.05 and about 7.85, between about 7.05 and about 7.80, between about 7.05 and about 7.75, between about 7.05 and about 7.7, between about 7.05 and about 7.65, between about 7.05 and about 7.6, between about 7.05 and about 7.55, between about 7.05 and about 7.5, between about 7.05 and about 7.45, between about 7.05 and about 7.4, between about 7.05 and about 7.35, between about 7.05 and about 7.3, between about 7.05 and about 7.25, between about 7.05 and about 7.2, between about 7.05 and about 7.15, between about 7.1 and about 7.85, between about 7.1 and about 7.8, between about 7.1 and about 7.75, between about 7.1 and about 7.7, between about 7.1 and about 7.65, between about 7.1 and about 7.6, between about 7.1 and about 7.55, between about 7.1 and about 7.5, between about 7.1 and about 7.45, between about 7.1 and about 7.4, between about 7.1 and about 7.35, between about 7.1 and about 7.3, between about 7.1 and about 7.25, between about 7.1 and about 7.2, between about 7.15 and about 7.85, between about 7.15 and about 7.8, between about 7.15 and about 7.75, between about 7.15 and about 7.7, between about 7.15 and about 7.65, between about 7.15 and about 7.6, between about 7.15 and about 7.55, between about 7.15 and about 7.5, between about 7.15 and about 7.45, between about 7.15 and about 7.4, between about 7.15 and about 7.35, between about 7.15 and about 7.3, between about 7.15 and about 7.25, between about 7.2 and about 7.85, between about 7.2 and about 7.8, between about 7.2 and about 7.75, between about 7.2 and about 7.7, between about 7.2 and about 7.65, between about 7.2 and about 7.6, between about 7.2 and about 7.55, between about 7.2 and about 7.5, between about 7.2 and about 7.45, between about 7.2 and about 7.4, between about 7.2 and about 7.35, between about 7.2 and about 7.3, between about 7.25 and about 7.85, between about 7.25 and about 7.8, between about 7.25 and about 7.75, between about 7.25 and about 7.7, between about 7.25 and about 7.65, between about 7.25 and about 7.6, between about 7.25 and about 7.55, between about 7.25 and about 7.5, between about 7.25 and about 7.45, between about 7.25 and about 7.4, between about 7.25 and about 7.35, between about 7.3 and about 7.85, between about 7.3 and about 7.8, between about 7.3 and about 7.75, between about 7.3 and about 7.7, between about 7.3 and about 7.65, between about 7.3 and about 7.6, between about 7.3 and about 7.55, between about 7.3 and about 7.5, between about 7.3 and about 7.45, between about 7.3 and about 7.4, between about 7.35 and about 7.85, between about 7.35 and about 7.8, between about 7.35 and about 7.75, between about 7.35 and about 7.7, between about 7.35 and about 7.65, between about 7.35 and about 7.6, between about 7.35 and about 7.55, between about 7.35 and about 7.5, between about 7.35 and about 7.45, between about 7.4 and about 7.85, between about 7.4 and about 7.8, between about 7.4 and about 7.75, between about 7.4 and about 7.7, between about 7.4 and about 7.65, between about 7.4 and about 7.6, between about 7.45 and about 7.85, between about 7.45 and about 7.8, between about 7.45 and about 7.75, between about 7.45 and about 7.7, between about 7.45 and about 7.65, between about 7.45 and about 7.6, between about 7.45 and about 7.55, between about 7.5 and about 7.85, between about 7.5 and about 7.8, between about 7.5 and about 7.75, between about 7.5 and about 7.7, between about 7.5 and about 7.65, between about 7.5 and about 7.6, between about 7.55 and about 7.85, between about 7.55 and about 7.8, between about 7.55 and about 7.75, between about 7.55 and about 7.7, between about 7.55 and about 7.65, between about 7.6 and about 7.85, between about 7.6 and about 7.8, between about 7.6 and about 7.75, between about 7.6 and about 7.7, between about 7.65 and about 7.85, between about 7.65 and about 7.8, between about 7.65 and about 7.75, between about 7.7 and about 7.85, between about 7.7 and about 7.8, or between about 7.75 and about 7.85) and adjusting (e.g., increasing or decreasing) the sodium chloride concentration of the fluid to between about 30 mM and about 200 mM (e.g., 30 mM and about 190 mM, between about 30 mM and about 180 mM, between about 30 mM and about 170 mM, between about 30 mM and about 160 mM, between about 30 mM and about 150 mM, between about 30 mM and about 140 mM, between about 30 mM and about 130 mM, between about 30 mM and about 120 mM, between about 30 mM and about 110 mM, between about 30 mM and about 100 mM, between about 30 mM and about 90 mM, between about 30 mM and about 80 mM, between about 30 mM and about 70 mM, between about 30 mM and about 60 mM, between about 30 mM and about 50 mM, between about 40 mM and about 200 mM, between about 40 mM and about 190 mM, between about 40 mM and about 180 mM, between about 40 mM and about 170 mM, between about 40 mM and about 160 mM, between about 40 mM and about 150 mM, between about 40 mM and about 140 mM, between about 40 mM and about 130 mM, between about 40 mM and about 120 mM, between about 40 mM and about 110 mM, between about 40 mM and about 100 mM, between about 40 mM and about 90 mM, between about 40 mM and about 80 mM, between about 40 mM and about 70 mM, between about 40 mM and about 60 mM, between about 50 mM and about 200 mM, between about 50 mM and about 190 mM, between about 50 mM and about 180 mM, between about 50 mM and about 170 mM, between about 50 mM and about 160 mM, between about 50 mM and about 150 mM, between about 50 mM and about 140 mM, between about 50 mM and about 130 mM, between about 50 mM and about 120 mM, between about 50 mM and about 110 mM, between about 50 mM and about 100 mM, between about 50 mM and about 90 mM, between about 50 mM and about 80 mM, between about 50 mM and about 70 mM, between about 60 mM and about 200 mM, between about 60 mM and about 190 mM, between about 60 mM and about 180 mM, between about 60 mM and about 170 mM, between about 60 mM and about 160 mM, between about 60 mM and about 150 mM, between about 60 mM and about 140 mM, between about 60 mM and about 130 mM, between about 60 mM and about 120 mM, between about 60 mM and about 110 mM, between about 60 mM and about 100 mM, between about 60 mM and about 90 mM, between about 60 mM and about 80 mM, between about 70 mM and about 200 mM, between about 70 mM and about 190 mM, between about 70 mM and about 180 mM, between about 70 mM and about 170 mM, between about 70 mM and about 160 mM, between about 70 mM and about 150 mM, between about 70 mM and about 140 mM, between about 70 mM and about 130 mM, between about 70 mM and about 120 mM, between about 70 mM and about 110 mM, between about 70 mM and about 100 mM, between about 70 mM and about 90 mM, between about 80 mM and about 200 mM, between about 80 mM and about 190 mM, between about 80 mM and about 180 mM, between about 80 mM and about 170 mM, between about 80 mM and about 160 mM, between about 80 mM and about 150 mM, between about 80 mM and about 140 mM, between about 80 mM and about 130 mM, between about 80 mM and about 120 mM, between about 80 mM and about 110 mM, between about 80 mM and about 100 mM, between about 90 mM and about 200 mM, between about 90 mM and about 190 mM, between about 90 mM and about 180 mM, between about 90 mM and about 170 mM, between about 90 mM and about 160 mM, between about 90 mM and about 150 mM, between about 90 mM and about 140 mM, between about 90 mM and about 130 mM, between about 90 mM and about 120 mM, between about 90 mM and about 110 mM, between about 100 mM and about 200 mM, between about 100 mM and about 190 mM, between about 100 mM and about 180 mM, between about 100 mM and about 170 mM, between about 100 mM and about 160 mM, between about 100 mM and about 150 mM, between about 100 mM and about 140 mM, between about 100 mM and about 130 mM, between about 100 mM and about 120 mM, between about 110 mM and about 190 mM, between about 110 mM and about 180 mM, between about 110 mM and about 170 mM, between about 110 mM and about 160 mM, between about 110 mM and about 150 mM, between about 110 mM and about 140 mM, between about 110 mM and about 130 mM, between about 120 mM and about 200 mM, between about 120 mM and about 190 mM, between about 120 mM and about 180 mM, between about 120 mM and about 170 mM, between about 120 mM and about 160 mM, between about 120 mM and about 150 mM, between about 120 mM and about 140 mM, between about 130 mM and about 200 mM, between about 130 mM and about 190 mM, between about 130 mM and about 180 mM, between about 130 mM and about 170 mM, between about 130 mM and about 160 mM, between about 130 mM and about 150 mM, between about 140 mM and about 200 mM, between about 140 mM and about 190 mM, between about 140 mM and about 180 mM, between about 140 mM and about 170 mM, between about 140 mM and about 160 mM, between about 150 mM and about 200 mM, between about 150 mM and about 190 mM, between about 150 mM and about 180 mM, between about 150 mM and about 170 mM, between about 160 mM and about 200 mM, between about 160 mM and about 190 mM, between about 160 mM and about 180 mM, between about 170 mM and about 200 mM, between about 170 mM and about 190 mM, or between about 180 mM and about 200 mM); and (b) flowing the fluid through a virus filter (e.g., any of the virus filters described herein) to produce a filtrate including the recombinant antibody. Some embodiments of these methods further include, immediately prior to step (b), flowing the fluid through a pre-filter (e.g., any of the pre-filters described herein, such as a pre-filter including a polyamide membrane, such as a Sartorius Virosart® Max pre-filter).

In some embodiments of any of these methods, the fluid includes between about 10 mM and about 50 mM (e.g., between about 10 mM and about 45 mM, between about 10 mM and about 40 mM, between about 10 mM and about 35 mM, between about 10 mM and about 30 mM, between about 10 mM and about 25 mM, between about 10 mM and about 20 mM, between about 15 mM and about 50 mM, between about 15 mM and about 45 mM, between about 15 mM and about 40 mM, between about 15 mM and about 35 mM, between about 15 mM and about 30 mM, between about 15 mM and about 25 mM, between about 20 mM and about 50 mM, between about 20 mM and about 45 mM, between about 20 mM and about 40 mM, between about 20 mM and about 35 mM, between about 20 mM and about 30 mM, between about 25 mM and about 50 mM, between about 25 mM and about 45 mM, between about 25 mM and about 40 mM, between about 25 mM and about 35 mM, between about 30 mM and about 50 mM, between about 30 mM and about 45 mM, between about 30 mM and about 40 mM, between about 35 mM and about 50 mM, between about 35 mM and about 45 mM, or between about 40 mM and about 50 mM) sodium phosphate.

In some examples of any of the methods in this section, the recombinant antibody can include a heavy chain variable domain that includes one or more (e.g., one, two, or three) of a CDR1 including a sequence of SEQ ID NO: 21, a CDR2 including a sequence of SEQ ID NO: 22, and a CDR3 including a sequence of SEQ ID NO: 23. In some examples of any of the methods described in this section, the recombinant antibody can include a heavy chain variable region including a sequence of SEQ ID NO: 24. In some examples of any of the methods described in this section, the recombinant antibody can include a heavy chain including a sequence of SEQ ID NO: 25 (BNJ383 heavy chain). In some examples of any of the methods described in this section, the light chain variable region includes one or more (e.g., one, two, or three) of a CDR1 including a sequence of SEQ ID NO: 26, a CDR2 including a sequence of SEQ ID NO: 27, and a CDR3 including a sequence of SEQ ID NO: 28. In some examples of any of the methods described in this section, the recombinant antibody can include a light chain variable region including a sequence of SEQ ID NO: 29. In some examples of any of the methods described in this section, the recombinant antibody can include a light chain including a sequence of SEQ ID NO: 30 (BNJ383 light chain).

Methods of Performing Viral Filtration (Part D)

Also provided are methods of performing viral filtration that include: (a) adjusting (e.g., increasing or decreasing) the pH of a fluid including a recombinant antibody (e.g., any of the recombinant antibodies described herein) to between about 5.0 and about 7.0 (e.g., between about 5.0 and about 6.9, between about 5.0 and about 6.8, between about 5.0 and about 6.7, between about 5.0 and about 6.6, between about 5.0 and about 6.5, between about 5.0 and about 6.4, between about 5.0 and about 6.3, between about 5.0 and about 6.2, between about 5.0 and about 6.1, between about 5.0 and about 6.0, between about 5.0 and about 5.9, between about 5.0 and about 5.8, between about 5.0 and about 5.7, between about 5.0 and about 5.6, between about 5.0 and about 5.5, between about 5.0 and about 5.4, between about 5.0 and about 5.3, between about 5.0 and about 5.2, between about 5.1 and about 7.0, between about 5.1 and about 6.9, between about 5.1 and about 6.8, between about 5.1 and about 6.7, between about 5.1 and about 6.6, between about 5.1 and about 6.5, between about 5.1 and about 6.4, between about 5.1 and about 6.3, between about 5.1 and about 6.2, between about 5.1 and about 6.1, between about 5.1 and about 6.0, between about 5.1 and about 5.9, between about 5.1 and about 5.8, between about 5.1 and about 5.7, between about 5.1 and about 5.6, between about 5.1 and about 5.5, between about 5.1 and about 5.4, between about 5.1 and about 5.3, between about 5.2 and about 7.0, between about 5.2 and about 6.9, between about 5.2 and about 6.8, between about 5.2 and about 6.7, between about 5.2 and about 6.6, between about 5.2 and about 6.5, between about 5.2 and about 6.4, between about 5.2 and about 6.3, between about 5.2 and about 6.2, between about 5.2 and about 6.1, between about 5.2 and about 6.0, between about 5.2 and about 5.9, between about 5.2 and about 5.8, between about 5.2 and about 5.7, between about 5.2 and about 5.6, between about 5.2 and about 5.5, between about 5.2 and about 5.4, between about 5.3 and about 7.0, between about 5.3 and about 6.9, between about 5.3 and about 6.8, between about 5.3 and about 6.7, between about 5.3 and about 6.6, between about 5.3 and about 6.5, between about 5.3 and about 6.4, between about 5.3 and about 6.3, between about 5.3 and about 6.2, between about 5.3 and about 6.1, between about 5.3 and about 6.0, between about 5.3 and about 5.9, between about 5.3 and about 5.8, between about 5.3 and about 5.7, between about 5.3 and about 5.6, between about 5.3 and about 5.5, between about 5.4 and about 7.0, between about 5.4 and about 6.9, between about 5.4 and about 6.8, between about 5.4 and about 6.7, between about 5.4 and about 6.6, between about 5.4 and about 6.5, between about 5.4 and about 6.4, between about 5.4 and about 6.3, between about 5.4 and about 6.2, between about 5.4 and about 6.1, between about 5.4 and about 6.0, between about 5.4 and about 5.9, between about 5.4 and about 5.8, between about 5.4 and about 5.7, between about 5.4 and about 5.6, between about 5.5 and about 7.0, between about 5.5 and about 6.9, between about 5.5 and about 6.8, between about 5.5 and about 6.7, between about 5.5 and about 6.6, between about 5.5 and about 6.5, between about 5.5 and about 6.4, between about 5.5 and about 6.3, between about 5.5 and about 6.2, between about 5.5 and about 6.1, between about 5.5 and about 6.0, between about 5.5 and about 5.9, between about 5.5 and about 5.8, between about 5.5 and about 5.7, between about 5.6 and about 7.0, between about 5.6 and about 6.9, between about 5.6 and about 6.8, between about 5.6 and about 6.7, between about 5.6 and about 6.6, between about 5.6 and about 6.5, between about 5.6 and about 6.4, between about 5.6 and about 6.3, between about 5.6 and about 6.2, between about 5.6 and about 6.1, between about 5.6 and about 6.0, between about 5.6 and about 5.9, between about 5.6 and about 5.8, between about 5.7 and about 7.0, between about 5.7 and about 6.9, between about 5.7 and about 6.8, between about 5.7 and about 6.7, between about 5.7 and about 6.6, between about 5.7 and about 6.5, between about 5.7 and about 6.4, between about 5.7 and about 6.3, between about 5.7 and about 6.2, between about 5.7 and about 6.1, between about 5.7 and about 6.0, between about 5.7 and about 5.9, between about 5.8 and about 7.0, between about 5.8 and about 6.9, between about 5.8 and about 6.8, between about 5.8 and about 6.7, between about 5.8 and about 6.6, between about 5.8 and about 6.5, between about 5.8 and about 6.4, between about 5.8 and about 6.3, between about 5.8 and about 6.2, between about 5.8 and about 6.1, between about 5.8 and about 6.0, between about 5.9 and about 7.0, between about 5.9 and about 6.9, between about 5.9 and about 6.8, between about 5.9 and about 6.7, between about 5.9 and about 6.6, between about 5.9 and about 6.5, between about 5.9 and about 6.4, between about 5.9 and about 6.3, between about 5.9 and about 6.2, between about 5.9 and about 6.1, between about 6.0 and about 7.0, between about 6.0 and about 6.9, between about 6.0 and about 6.8, between about 6.0 and about 6.7, between about 6.0 and about 6.6, between about 6.0 and about 6.5, between about 6.0 and about 6.4, between about 6.0 and about 6.3, between about 6.0 and about 6.2, between about 6.1 and about 7.0, between about 6.1 and about 6.9, between about 6.1 and about 6.8, between about 6.1 and about 6.7, between about 6.1 and about 6.6, between about 6.1 and about 6.5, between about 6.1 and about 6.4, between about 6.1 and about 6.3, between about 6.2 and about 7.0, between about 6.2 and about 6.9, between about 6.2 and about 6.8, between about 6.2 and about 6.7, between about 6.2 and about 6.6, between about 6.2 and about 6.5, between about 6.2 and about 6.4, between about 6.3 and about 7.0, between about 6.3 and about 6.9, between about 6.3 and about 6.8, between about 6.3 and about 6.7, between about 6.3 and about 6.6, between about 6.3 and about 6.5, between about 6.4 and about 7.0, between about 6.4 and about 6.9, between about 6.4 and about 6.8, between about 6.4 and about 6.7, between about 6.4 and about 6.6, between about 6.5 and about 7.0, between about 6.5 and about 6.9, between about 6.5 and about 6.8, between about 6.5 and about 6.7, between about 6.6 and about 7.0, between about 6.6 and about 6.9, between about 6.6 and about 6.8, between about 6.7 and about 7.0, between about 6.7 and about 6.9, or between about 6.8 and about 7.0); and (b) flowing the fluid through a virus filter (e.g., any of the virus filters described herein) to produce a filtrate including the recombinant antibody.

Some embodiments of these methods further include, prior to step (b) adjusting (e.g., increasing or decreasing) the sodium chloride concentration of the fluid to between about 60 mM and about 300 mM (e.g., between about 60 mM and about 280 mM, between about 60 mM and about 260 mM, between about 60 mM and about 240 mM, between about 60 mM and about 220 mM, between about 60 mM and about 200 mM, between about 60 mM and about 180 mM, between about 60 mM and about 160 mM, between about 60 mM and about 140 mM, between about 60 mM and about 120 mM, between about 60 mM and about 100 mM, between about 60 mM and about 80 mM, between about 80 mM and about 300 mM, between about 80 mM and about 280 mM, 80 mM and about 260 mM, between about 80 mM and about 240 mM, between about 80 mM and about 220 mM, between about 80 mM and about 200 mM, between about 80 mM and about 180 mM, between about 80 mM and about 160 mM, between about 80 mM and about 140 mM, between about 80 mM and about 120 mM, between about 80 mM and about 100 mM, between about 100 mM and about 300 mM, between about 100 mM and about 280 mM, between about 100 mM and about 260 mM, between about 100 mM and about 240 mM, between about 100 mM and about 220 mM, between about 100 mM and about 200 mM, between about 100 mM and about 180 mM, between about 100 mM and about 160 mM, between about 100 mM and about 140 mM, between about 100 mM and about 120 mM, between about 120 mM and about 300 mM, between about 120 mM and about 280 mM, between about 120 mM and about 260 mM, between about 120 mM and about 240 mM, between about 120 mM and about 220 mM, between about 120 mM and about 200 mM, between about 120 mM and about 180 mM, between about 120 mM and about 160 mM, between about 120 mM and about 140 mM, between about 140 mM and about 300 mM, between about 140 mM and about 280 mM, between about 140 mM and about 260 mM, between about 140 mM and about 240 mM, between about 140 mM and about 220 mM, between about 140 mM and about 200 mM, between about 140 mM and about 180 mM, between about 140 mM and about 160 mM, between about 160 mM and about 300 mM, between about 160 mM and about 280 mM, between about 160 mM and about 260 mM, between about 160 mM and about 240 mM, between about 160 mM and about 220 mM, between about 160 mM and about 200 mM, between about 160 mM and about 180 mM, between about 180 mM and about 300 mM, between about 180 mM and about 280 mM, between about 180 mM and about 260 mM, between about 180 mM and about 240 mM, between about 180 mM and about 220 mM, between about 180 mM and about 200 mM, between about 200 mM and about 300 mM, between about 200 mM and about 280 mM, between about 200 mM and about 260 mM, between about 200 mM and about 240 mM, between about 200 mM and about 220 mM, between about 220 mM and about 300 mM, between about 220 mM and about 280 mM, between about 220 mM and about 260 mM, between about 220 mM and about 240 mM, between about 240 mM and about 300 mM, between about 240 mM and about 280 mM, between about 240 mM and about 260 mM, between about 260 mM and about 300 mM, between about 260 mM and about 280 mM, or between about 280 mM and about 300 mM).

In some embodiments of any of these methods, the fluid includes between about 10 mM and about 50 mM (e.g., between about 10 mM and about 45 mM, between about 10 mM and about 40 mM, between about 10 mM and about 35 mM, between about 10 mM and about 30 mM, between about 10 mM and about 25 mM, between about 10 mM and about 20 mM, between about 15 mM and about 50 mM, between about 15 mM and about 45 mM, between about 15 mM and about 40 mM, between about 15 mM and about 35 mM, between about 15 mM and about 30 mM, between about 15 mM and about 25 mM, between about 20 mM and about 50 mM, between about 20 mM and about 45 mM, between about 20 mM and about 40 mM, between about 20 mM and about 35 mM, between about 20 mM and about 30 mM, between about 25 mM and about 50 mM, between about 25 mM and about 45 mM, between about 25 mM and about 40 mM, between about 25 mM and about 35 mM, between about 30 mM and about 50 mM, between about 30 mM and about 45 mM, between about 30 mM and about 40 mM, between about 35 mM and about 50 mM, between about 35 mM and about 45 mM, or between about 40 mM and about 50 mM) sodium phosphate.

Some embodiments of these methods further include, immediately prior to step (b), flowing the fluid through a pre-filter (e.g., any of the pre-filters described herein, such as a pre-filter including a polyamide membrane, such as a Sartorius Virosart® Max pre-filter).

Examples of recombinant antibodies can include a heavy chain variable domain that includes one or more (e.g., one, two, or three) of a CDR1 including a sequence of SEQ ID NO: 31, a CDR2 including a sequence of SEQ ID NO: 32, and a CDR3 including a sequence of SEQ ID NO: 33. In some examples of any of the recombinant antibodies described herein, the recombinant antibody can include a heavy chain variable region including a sequence of SEQ ID NO: 34. In some examples of any of the recombinant antibodies described herein, the recombinant antibody can include a heavy chain including a sequence of SEQ ID NO: 35 (e.g., samalizumab heavy chain). In some examples of any of the recombinant antibodies described herein, the light chain variable region includes one or more (e.g., one, two, or three) of a CDR1 including a sequence of SEQ ID NO: 36, a CDR2 including a sequence of SEQ ID NO: 37, and a CDR3 including a sequence of SEQ ID NO: 38. In some examples of any of the recombinant antibodies described herein, the recombinant antibody can include a light chain variable region including a sequence of SEQ ID NO: 39. In some examples of any of the recombinant antibodies described herein, the recombinant antibody can include a light chain including a sequence of SEQ ID NO: 40 (e.g., samalizumab light chain).

Methods of Purifying or Manufacturing a Recombinant Antibody

Provided herein are methods of purifying a recombinant antibody and methods of manufacturing a recombinant antibody. The methods can include, for example, (a) capturing a recombinant antibody from a fluid including the recombinant antibody, e.g., a clarified liquid culture medium or a buffered fluid including the recombinant antibody; (b) following capturing, performing one or more unit operations on the recombinant antibody; and following steps (a) and (b), performing viral filtration on the recombinant antibody to provide a filtrate that includes purified recombinant antibody and, e.g., optionally is substantially free of soluble protein aggregates (e.g., using any of the methods of performing viral filtration described herein); and optionally, further (d) performing one or more unit operations on the purified recombinant antibody. Some embodiments further include, for example, performing at least one (such as two, three, or four) unit operation before the capturing step (e.g., selected from the group of clarifying a culture medium, ultrafiltration/diafiltration to concentrate the recombinant antibody in a fluid, viral inactivation, and adjusting (e.g., increasing or decreasing) one or both of the pH and ionic concentration of a fluid including the recombinant antibody). In some embodiments, step (b) includes performing one or more (such as two, three, or four) unit operations on the recombinant antibody, e.g., selected from the group of ultrafiltration/diafiltration to concentrate the recombinant antibody in a fluid, purifying the recombinant antibody, polishing the recombinant antibody, inactivating viruses, and adjusting (e.g., increasing or decreasing) one or both of the pH and ionic concentration of a fluid including the recombinant antibody. In some embodiments, step (b) includes, immediately prior to performing viral filtration, a step of performing the unit operation of pre-filtration by passing a fluid including the recombinant antibody through a pre-filter. In some embodiments, step (b) includes performing the following unit operations of: purifying the recombinant antibody, inactivating viruses, ultrafiltration/diafiltration to concentrate the recombinant antibody in a fluid, depth filtration (e.g., using any of the exemplary depth filters described herein), adjusting (e.g., increasing or decreasing) the pH and ionic concentration of a fluid including the recombinant antibody, and pre-filtration (e.g., using any of the exemplary pre-filters described herein).

Some embodiments further include performing one or more (two, three, or four) unit operations after the step of performing viral filtration (e.g., one or more unit operations selected from the group of purifying the recombinant antibody, polishing the recombinant antibody, adjusting (e.g., increasing or decreasing) one or both of the pH and ionic concentration of a fluid including the purified recombinant antibody, or passing the fluid through an additional virus filter). Some embodiments further include performing a step of formulating the purified recombinant antibody after performing viral filtration.

The methods provided herein can result in a purified recombinant antibody that is, e.g., at least or about 95%, 96%, 97%, 98%, 98.2%, 98.4%, 98.6%, 98.8%, 99.0%, 99.1%, 99.2%, 99.3%, 99.4%, 99.5%, 99.6%, 99.7%, 99.8%, or 99.9% free of soluble protein aggregates or includes no detectable soluble protein aggregates. The methods provided herein can also provide, e.g., for a reduction, such as up to a 5% reduction, up to a 10% reduction, up to a 15% reduction, up to a 20% reduction, up to a 25% reduction, up to a 30% reduction, up to a 35% reduction, up to a 40% reduction, up to a 45% reduction, up to a 50% reduction, up to a 55% reduction, up to a 60% reduction, up to a 65% reduction, up to a 70% reduction, up to a 75% reduction, up to a 80% reduction, up to an 85% reduction, up to a 90% reduction, up to a 95% reduction, or up to a 99% reduction in host cell protein present in a purified recombinant antibody (e.g., as compared to a purified recombinant antibody produced by a method that does not include a viral filtration step performed using any of the methods described herein (and optionally also does not include a pre-filtration step prior to the viral filtration step), after a step of capturing the recombinant protein (and optionally further after one or more additional unit operations)). Methods for determining the level of host cell protein are well known in the art. For example, kits for detecting the level of host cell protein are commercially available from Cygnus Technologies (Southport, NC), ArrayBridge (St. Louis, MO), Cisbio (Bedford, MA), and Lonza (Basel, Switzerland).

In some embodiments of any of the methods described herein, the filtrate produced by the viral filtration in step (c) can include a reduced level (e.g., up to 5% reduction, up to 10% reduction, up to 15% reduction, up to 20% reduction, up to 30% reduction, up to a 35% reduction, up to a 40% reduction, up to a 45% reduction, up to a 50% reduction, up to a 55% reduction, up to a 60% reduction, up to a 60% reduction, up to a 70% reduction, up to a 75% reduction, up to a 80% reduction, up to a 85% reduction, up to a 90% reduction, up to a 95% reduction, or up to a 99% reduction) in the level of soluble protein aggregates (e.g., as compared to a level of soluble protein aggregates in a purified recombinant antibody produced by a method that does not include a viral filtration step performed using any of the methods described herein (and optionally also does not include a pre-filtration step prior to the viral filtration step), after a step of capturing the recombinant protein (and optionally further after one or more additional unit operations)).

The methods provided herein can also result in a purified recombinant antibody that has a decreased level of immunogenicity when administered to a subject (such as a human subject) (e.g., as compared to the immunogenicity of a purified recombinant antibody produced by a method that does not include a viral filtration step performed using any of the methods described herein (and optionally also does not include a pre-filtration step prior to the viral filtration step), after a step of capturing the recombinant protein (and optionally further after one or more additional unit operations)).

The methods provided herein can further provide for a reduced risk of virus filter fouling or contamination in a method of purifying a recombinant protein and a method of manufacturing a recombinant protein product or in a system used to perform the same (e.g., as compared to a method that does not include a viral filtration step performed using any of the methods described herein (and optionally also does not include a pre-filtration step prior to the viral filtration step), after a step of capturing the recombinant protein (and optionally further after one or more additional unit operations) or a system used to perform the same).

Cells and Cell Culture

Cells including a nucleic acid encoding a recombinant antibody can be used to produce the recombinant antibody (such as a secreted recombinant antibody). In some examples, the nucleic acid encoding the recombinant antibody is stably integrated into the genome of the cell.

The cells used to produce the recombinant antibody can be bacteria (e.g., gram negative bacteria), yeast (e.g., *Saccharomyces cerevisiae, Pichia pastoris, Hansenula polymorpha, Kluyveromyces lactis, Schizosaccharomyces pombe, Yarrowia lipolytica,* or *Arxula adeninivorans*), or mammalian cells.

The mammalian cell used to produce the recombinant antibody can be a cell that grows in suspension or an adherent cell. Non-limiting examples of mammalian cells that can be cultured to produce a recombinant antibody (e.g., any of the recombinant antibodies described herein, such as eculizumab, samalizumab, BNJ441, and BNJ383) include: Chinese hamster ovary (CHO) cells (such as CHO DG44 cells or CHO-K1s cells), Sp2.0, myeloma cells (such as NS/0 cells), B-cells, hybridoma cells, T-cells, human embryonic kidney (HEK) cells (such as HEK 293E and HEK 293F), African green monkey kidney epithelial cells (Vero) cells, and Madin-Darby Canine (Cocker Spaniel) kidney epithelial cells (MDCK) cells. In some examples where an adherent cell is used to produce a recombinant antibody, the cell is cultured in the presence of a plurality of microcarriers (such as microcarriers that include one or more pores). Additional mammalian cells that can be cultured to produce a recombinant antibody (such as a secreted recombinant antibody) are known in the art. In some instances, the mammalian cell is cultured in a bioreactor. In some embodiments, the mammalian cell used to inoculate a bioreactor was derived from a frozen cell stock or a seed train culture.

A nucleic acid encoding a recombinant antibody can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid is not stably integrated into a chromosome of the mammalian cell (transient transfection), while in others it is stably integrated into a chromosome of the mammalian cell. Alternatively or in addition, the nucleic acid can be present in a plasmid and/or in a mammalian artificial chromosome (such as a human artificial chromosome). Alternatively or in addition, the nucleic acid can be introduced into the cell using a viral vector (such as a lentivirus, retrovirus, or adenovirus vector). The nucleic acid can be operably linked to a promoter sequence (such as a strong promoter, such as a β-actin promoter and CMV promoter, or an inducible promoter). The nucleic acid can be operably linked to a heterologous promoter. A vector including the nucleic acid can, if desired, also include a selectable marker (such as a gene that confers hygromycin, puromycin, or neomycin resistance to the mammalian cell).

As noted herein, the recombinant antibody can be a secreted antibody that is released by the mammalian cell into the extracellular medium. For example, a nucleic acid sequence encoding a soluble recombinant antibody can include a sequence that encodes a secretion signal peptide at the N-terminus of the recombinant antibody, which is cleaved by an enzyme present in the mammalian cell, and subsequently released into the extracellular medium (such as the first and/or second liquid culture medium in a perfusion cell culture or the first liquid culture medium and/or liquid feed culture medium in a feed batch culture).

Any of the methods described herein can further include culturing a mammalian cell including a nucleic acid encoding a recombinant antibody under conditions sufficient to produce the recombinant antibody (such as a secreted recombinant antibody).

Fed Batch Culturing

The culturing step in the methods described herein can include fed batch culturing. As is known in the art, fed batch culturing includes incremental (periodic) or continuous addition of a feed culture medium to an initial cell culture, which includes a first liquid culture medium, without substantial or significant removal of the first liquid culture medium from the cell culture. The cell culture in fed batch culturing can be disposed in a bioreactor (e.g., a production bioreactor, such as a 10,000-L production bioreactor). In some instances, the feed culture medium is the same as the first liquid culture medium. The feed culture medium may be either in a liquid form or a dry powder. In other instances, the feed culture medium is a concentrated form of the first liquid culture medium and/or is added as a dry powder. In some embodiments, both a first liquid feed culture medium and a different second liquid feed culture medium are added (e.g., continuously added) to the first liquid culture medium. In some examples, the addition of the first liquid feed culture medium and addition of the second liquid feed culture medium to the culture is initiated at about the same time. In some examples, the total volume of the first liquid feed culture medium and the second liquid feed culture medium added to the culture over the entire culturing period are about the same.

When the feed culture medium is added continuously, the rate of addition of the feed culture medium can be held constant or can be increased (e.g., steadily increased) over the culturing period. A continuous addition of feed culture medium can start at a specific time point during the culturing period (e.g., when the mammalian cells reach a target viable cell density, e.g., a viable cell density of about $1 \times 10^6$ cells/mL, about $1.1 \times 10^6$ cells/mL, about $1.2 \times 10^6$ cells/mL, about $1.3 \times 10^6$ cells/mL, about $1.4 \times 10^6$ cells/mL, about $1.5 \times 10^6$ cells/mL, about $1.6 \times 10^6$ cells/mL, about $1.7 \times 10^6$ cells/mL, about $1.8 \times 10^6$ cells/mL, about $1.9 \times 10^6$ cells/mL, or about $2.0 \times 10^6$ cells/mL). In some embodiments, the continuous addition of feed culture medium can be initiated at day 2, day 3, day 4, or day 5 of the culturing period.

In some embodiments, an incremental (periodic) addition of feed culture medium can begin when the mammalian cells reach a target cell density (e.g., about $1 \times 10^6$ cells/mL, about $1.1 \times 10^6$ cells/mL, about $1.2 \times 10^6$ cells/mL, about $1.3 \times 10^6$ cells/mL, about $1.4 \times 10^6$ cells/mL, about $1.5 \times 10^6$ cells/mL, about $1.6 \times 10^6$ cells/mL, about $1.7 \times 10^6$ cells/mL, about $1.8 \times 10^6$ cells/mL, about $1.9 \times 10^6$, or about $2.0 \times 10^6$ cells/mL). Incremental feed culture media addition can occur at regular intervals (e.g., every day, every other day, or every third day) or can occur when the cells reach specific target cell densities (e.g., target cell densities that increase over the culturing period). In some embodiments, the amount of feed culture medium added can progressively increase between the first incremental addition of feed culture medium and subsequent additions of feed culture medium. The volume of a liquid culture feed culture medium added to the initial cell culture over any 24 hour period in the culturing period can be some fraction of the initial volume of the bioreactor containing the culture or some fraction of the volume of the initial culture.

For example, the addition of the liquid feed culture medium (continuously or periodically) can occur at a time point that is between 6 hours and 7 days, between about 6 hours and about 6 days, between about 6 hours and about 5 days, between about 6 hours and about 4 days, between about 6 hours and about 3 days, between about 6 hours and about 2 days, between about 6 hours and about 1 day, between about 12 hours and about 7 days, between about 12 hours and about 6 days, between about 12 hours and about 5 days, between about 12 hours and about 4 days, between about 12 hours and about 3 days, between about 12 hours and about 2 days, between about 1 day and about 7 days, between about 1 day and about 6 days, between about 1 day and about 5 days, between about 1 day and about 4 days, between about 1 day and about 3 days, between about 1 day and about 2 days, between about 2 days and about 7 days, between about 2 days and about 6 days, between about 2 days and about 5 days, between about 2 days and about 4 days, between about 2 days and about 3 days, between about 3 days and about 7 days, between about 3 days and about 6 days, between about 3 days and about 5 days, between about 3 days and about 4 days, between about 4 days and about 7 days, between about 4 days and about 6 days, between about 4 days and about 5 days, between about 5 days and about 7 days, or between about 5 days and about 6 days, after the start of the culturing period.

The volume of a liquid feed culture medium added (continuously or periodically) to the initial cell culture over any 24 hour period can be between 0.01× and about 0.3× of the capacity of the bioreactor. In other embodiments, the volume of a liquid feed culture medium added (continuously or periodically) to the initial cell culture over any 24 hour period during the culturing period can be between 0.02× and about 1.0× of the volume of the initial cell culture. The total amount of feed culture medium added (continuously or periodically) over the entire culturing period can be between about 1% and about 40% of the volume of the initial culture.

In some examples, two different feed culture media are added (continuously or incrementally) during feed batch culturing. The amount or volume of the first feed culture medium and the second feed culture medium added can be substantially the same or can differ. The first feed culture medium can be in the form of a liquid and the second feed culture medium can be in the form of a solid, or vice-versa. The first feed culture medium and the second feed culture medium can be liquid feed culture media.

Perfusion Culturing

The culturing step in the methods described herein can be perfusion culturing. As is known in the art, perfusion culturing includes removing from a bioreactor (e.g., a production bioreactor) a first volume of a first liquid culture medium, and adding to the production bioreactor a second volume of a second liquid culture medium, wherein the first volume and the second volume are typically (but need not be) about equal. The mammalian cells are retained in the bioreactor by some cell retention device or through techniques known in the art, such as cell settling. Removal and addition of culture media in perfusion culturing can be performed simultaneously or sequentially, or in some combination of the two. Further, removal and addition can be performed continuously, such as at a rate that removes and replaces a volume of between 0.1% to 800%, between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30% of the capacity of the bioreactor over an increment of time (such as over a 24-hour increment of time).

The first volume of the first liquid culture medium removed and the second volume of the second liquid culture medium added can in some instances be held approximately the same over each 24-hour period. As is known in the art, the rate at which the first volume of the first liquid culture medium is removed (volume/unit of time) and the rate at which the second volume of the second liquid culture medium is added (volume/unit of time) can be varied and depends on the conditions of the particular cell culture system. The rate at which the first volume of the first liquid culture medium is removed (volume/unit of time) and the rate at which the second volume of the second liquid culture medium is added (volume/unit of time) can be about the same or can be different.

Alternatively, the volume removed and added can change by gradually increasing over each 24-hour period. For example, the volume of the first liquid culture medium removed and the volume of the second liquid culture medium added within each 24-hour period can be increased over the culturing period. The volume can be increased a volume that is between 0.5% and about 20% of the capacity of the bioreactor over a 24-hour period. The volume can be increased over the culturing period to a volume that is about 25% and about 150% of the capacity of the bioreactor or the first liquid culture medium volume over a 24-hour period.

In some examples of the methods described herein, after the first 48 to 96 hours of the culturing period, in each 24-hour period, the first volume of the first liquid culture medium removed and the second volume of the second liquid culture medium added is about 10% and about 95%, about 10% and about 20%, about 20% and about 30%, about 30% and about 40%, about 40% and about 50%, about 50% and about 60%, about 60% and about 70%, about 70% and about 80%, about 80% and about 90%, about 85% and about 95%, about 60% and about 80%, or about 70% of the volume of the first liquid culture medium.

Skilled practitioners will appreciate that the first liquid culture medium and the second liquid culture medium can be the same type of media. In other instances, the first liquid culture medium and the second liquid culture medium can be different. The second liquid culture medium may be more concentrated with respect to one or more media components. In some embodiments, the first liquid culture medium includes processed BSA, the second liquid culture medium includes processed BSA, or both the first and the second liquid culture medium include processed BSA.

The first volume of the first liquid culture medium can be removed using any method, e.g., using an automated system. For example, alternating tangential flow filtration may be used. Alternatively, the first volume of the first liquid culture medium can be removed by seeping or gravity flow of the first volume of the first liquid culture medium through a sterile membrane with a molecular weight cut-off that excludes the mammalian cell. Alternatively, the first volume of the first liquid culture medium can be removed by stopping or significantly decreasing the rate of agitation for a period of at least 1 minute, at least 2 minutes, 3 minutes, 4 minutes, 5 minutes, 10 minutes, 15 minutes, 20 minutes, 25 minutes, 30 minutes, 40 minutes, 50 minutes, or 1 hour, and removing or aspirating the first volume of the first liquid culture medium from the top of the production bioreactor.

The second volume of the second liquid culture medium can be added to the first liquid culture medium by a pump. The second liquid culture medium can be added to the first liquid medium manually, such as by pipetting or injecting the second volume of the second liquid culture medium directly onto the first liquid culture medium or in an automated fashion.

Liquid Culture Medium and Clarification

A fluid including a recombinant antibody, e.g., a liquid culture medium including a recombinant antibody and that is substantially free of cells, can be derived from any source. For example, a liquid culture medium can be obtained from a recombinant cell culture (such as a recombinant bacterial, yeast, or mammalian cell culture). The liquid culture medium can be obtained from a fed-batch mammalian cell culture (such as a fed-batch bioreactor containing a culture of mammalian cells that secrete the recombinant antibody) or a perfusion cell mammalian cell culture (such as a perfusion bioreactor containing a culture of mammalian cells that secrete the recombinant antibody). The liquid culture medium can be a clarified liquid culture medium from a culture of bacterial, yeast, or mammalian cells that secrete the recombinant antibody.

Liquid culture medium obtained from a recombinant cell culture can be clarified to obtain a liquid culture medium that is substantially free of cells and that includes a recombinant antibody (also called a clarified culture medium or clarified liquid culture medium). Methods for clarifying a liquid culture medium in order to remove cells are known in the art (such as through the use of 0.2-μm filtration and filtration using an Alternating Tangential Flow (ATF™) system or tangential flow filtration (TFF)). Recombinant cells can be removed from liquid culture medium using centrifugation and removing the supernatant or by allowing the cells to settle to the gravitational bottom of a container (such as a bioreactor) and removing the liquid culture medium that is substantially free of cells. The liquid culture medium can be obtained from a culture of recombinant cells (such as recombinant bacteria, yeast, or mammalian cells) producing any of the recombinant antibodies described herein.

The liquid culture medium including a recombinant antibody or the liquid culture media used to culture a mammalian cell including a nucleic acid encoding a recombinant antibody (such as the first and second liquid culture medium in perfusion culturing or the first liquid culture medium and the liquid feed culture medium in fed batch culturing) can be any of the types of liquid culture medium described herein or known in the art. For example, any of the liquid culture media described herein can be selected from the group of: animal-derived component free liquid culture medium, serum-free liquid culture medium, serum-containing liquid culture medium, chemically-defined liquid culture medium, and protein-free liquid culture medium. In any of the processes described herein, a liquid culture medium obtained from a culture can be diluted by addition of a second fluid (such as a buffered solution) before or after it is clarified and/or before the recombinant antibody is captured.

The liquid culture medium that includes a recombinant antibody and is substantially free of cells can be stored (such as at a temperature below about 15° C., below about 10° C., below about 4° C., below about 0° C., below about −20° C., below about −50° C., below about −70° C., or below about −80° C.) for at least or about 1 day, at least or about 2 days, at least or about 5 days, at least or about 10 days, at least or about 15 days, at least or about 20 days, or at least or about 30 days) prior to capturing the recombinant antibody from the liquid culture medium. Alternatively, in some examples, the recombinant antibody is captured from the liquid culture medium directly from a bioreactor after a clarification step.

Capturing the Recombinant Antibody

The methods provided herein include a step of capturing a recombinant antibody from a fluid including the recombinant antibody (such as a clarified liquid culture medium including the secreted recombinant antibody or a clarified liquid culture medium including the recombinant antibody that has been diluted with a buffered solution).

As can be appreciated in the art, through performance of the capturing step, the recombinant antibody can be partially purified or isolated (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrated, and stabilized from one or more other components present in a clarified liquid culture medium including the recombinant antibody (such as culture medium proteins or one or more other components (such as DNA, RNA, or other proteins) present in or secreted from a mammalian cell). Typically, capturing is performed using a resin that binds a recombinant antibody (such as through the use of affinity chromatography). Non-limiting examples of methods for capturing a recombinant antibody from a fluid including the recombinant antibody (such as a clarified liquid culture medium) are described herein and others are known in the art. In the methods described herein, a recombinant antibody can be captured from a fluid using at least one chromatography column (such as any of the chromatography columns and/or capture mechanisms described herein, such as affinity chromatography resin, an anionic exchange chromatography resin, a cationic exchange chromatography resin, a mixed-mode chromatography resin, a molecular sieve chromatography resin, or a hydrophobic interaction chromatography resin). The capturing step can be performed using a chromatography resin that utilizes a protein A-binding capture mechanism, an antibody- or antibody fragment-binding capture mechanism, a substrate binding capture mechanism, and an antigen binding capture mechanism. In some embodiments, the capturing system can be a protein A-binding capturing mechanism or an antigen-binding capturing mechanism (where the capturing antigen is specifically recognized by the recombinant antibody). If the recombinant enzyme includes a tag, the capturing system can be a protein, metal chelate, or antibody (or antibody fragment) that specifically binds to the tag present in the recombinant antibody. Non-limiting examples of resins that can be used to capture a recombinant antibody are described herein and additional resins are known in the art. Non-limiting examples of resin that utilize a protein A-binding capture mechanism is MABSELECT™ SURE™ resin and Protein A Sepharose™ CL-4B (GE Healthcare).

Exemplary non-limiting sizes and shapes of the chromatography column(s) that can be used to capture the recombinant antibody are well known in the art. The liquid culture medium fed (loaded) can include, for example, between about 0.05 mg/mL and about 100 mg/mL recombinant antibody, between about 0.1 mg/mL and about 90 mg/mL, between about 0.1 mg/mL and about 80 mg/mL, between about 0.1 mg/mL and about 70 mg/mL, between about 0.1 mg/mL and about 60 mg/mL, between about 0.1 mg/mL and about 50 mg/mL, between about 0.1 mg/mL and about 40 mg/mL, between about 0.1 mg/mL and about 30 mg/mL, between about 0.1 mg/mL and about 20 mg/mL, between 0.5 mg/mL and about 20 mg/mL, between about 0.1 mg/mL and about 15 mg/mL, between about 0.5 mg/mL and about 15 mg/mL, between about 0.1 mg/mL and about 10 mg/mL, or between about 0.5 mg/mL and about 10 mg/mL recombinant antibody.

As can be appreciated in the art, to capture the recombinant antibody using the chromatography column(s), one must perform the sequential chromatographic steps of loading, washing, eluting, and regenerating the chromatography column(s) or chromatography membrane(s).

Following the loading of the recombinant antibody onto the at least one chromatographic column that includes a resin that is capable of capturing the recombinant antibody, the at least one chromatographic column or chromatographic membrane is washed with at least one washing buffer. As can be appreciated in the art, the at least one (such as two, three, or four) washing buffer is meant to elute all proteins that are not the recombinant antibody from the at least one chromatography column, while not disturbing the interaction of the recombinant antibody with the resin.

Following washing, the recombinant antibody is eluted from the at least one chromatographic column or chromatographic membrane by passing an elution buffer through the at least one chromatographic column or chromatographic membrane. Non-limiting examples of elution buffers that can be used in these methods will depend on the capture mechanism and/or the recombinant antibody. For example, an elution buffer can include a different concentration of salt (e.g., increased salt concentration), a different pH (e.g., an increased or decreased salt concentration), or a molecule that will compete with the recombinant antibody for binding to the resin that is capable of performing the unit operation of capturing. Examples of such elution buffers for each exemplary capture mechanism described herein are well known in the art.

Following elution of the recombinant antibody from the at least one chromatographic column that includes a resin that is capable of capturing the recombinant antibody, and before the next volume of fluid including the recombinant antibody can be loaded onto the at least one chromatographic column, the at least one chromatography column or chromatographic membrane must be equilibrated using an regeneration buffer.

Depth Filtration

The methods can include a unit operation of depth filtration. Depth filtration includes flowing the recombinant antibody through a depth filter to provide a filtrate that includes the purified recombinant antibody and, e.g., is substantially free of soluble protein aggregates. Any of the exemplary depth filters or methods for depth filtration described herein can be used to flow a recombinant antibody through a depth filter.

In some embodiments of the methods described herein, the recombinant antibody is flowed through the depth filter in a fluid having a pH of between about 4.0 and about 8.5, between about 4.0 and about 8.4, between about 4.0 and about 8.2, between about 4.0 and about 8.0, between about 4.0 and about 8.0, between about 4.0 and about 7.8, between about 4.0 and about 7.6, between about 4.0 and about 7.5, between about 4.0 and about 7.4, between about 4.0 and about 7.2, between about 4.0 and about 7.0, between about 4.0 and about 6.8, between about 4.0 and about 6.6, between about 4.0 and about 6.4, between about 4.0 and about 6.2, between about 4.0 and about 6.0, between about 4.0 and about 5.8, between about 4.0 and about 5.6, between about 4.0 and about 5.4, between about 4.0 and about 5.2, between about 4.0 and about 5.0, between about 4.0 and about 4.8, between about 4.0 and about 4.6, between about 4.0 and about 4.4, between about 4.0 and about 4.2, between about 4.2 and about 8.5, between about 4.2 and about 8.4, between about 4.2 and about 8.2, between about 4.2 and about 8.0, between about 4.2 and about 7.8, between about 4.2 and about 7.6, between about 4.2 and about 7.5, between about 4.2 and about 7.4, between about 4.2 and about 7.2, between about 4.2 and about 7.0, between about 4.2 and about 6.8, between about 4.2 and about 6.6, between about 4.2 and about 6.4, between about 4.2 and about 6.2, between about 4.2 and about 6.0, between about 4.2 and about 5.8, between about 4.2 and about 5.6, between about 4.2 and about 5.4, between about 4.2 and about 5.2, between about 4.2 and about 5.0, between about 4.2 and about 4.8, between about 4.2 and about 4.6, between about 4.2 and about 4.4, between about 4.4 and about 8.5, between about 4.4 and about 8.4, between about 4.4 and about 8.2, between about 4.4 and about 8.0, between about 4.4 and about 7.8, between about 4.4 and about 7.6, between about 4.4 and about 7.5, between about 4.4 and about 7.4, between about 4.4 and about 7.2, between about 4.4 and about 7.0, between about 4.4 and about 6.8, between about 4.4 and about 6.6, between about 4.4 and about 6.4, between about 4.4 and about 6.2, between about 4.4 and about 6.0, between about 4.4 and about 5.8, between about 4.4 and about 5.6, between about 4.4 and about 5.4, between about 4.4 and about 5.2, between about 4.4 and about 5.0, between about 4.4 and about 4.8, between about 4.4 and about 4.6, between about 4.6 and about 8.5, between about 4.6 and about 8.4, between about 4.6 and about 8.2, between about 4.6 and about 8.0, between about 4.6 and about 7.8, between about 4.6 and about 7.6, between about 4.6 and about 7.5, between about 4.6 and about 7.4, between about 4.6 and about 7.2, between about 4.6 and about 7.0, between about 4.6 and about 6.8, between about 4.6 and about 6.6, between about 4.6 and about 6.4, between about 4.6 and about 6.2, between about 4.6 and about 6.0, between about 4.6 and about 5.8, between about 4.6 and about 5.6, between about 4.6 and about 5.4, between about 4.6 and about 5.2, between about 4.6 and about 5.0, between about 4.6 and about 4.8, between about 4.8 and about 8.5, between about 4.8 and about 8.4, between about 4.8 and about 8.2, between about 4.8 and about 8.0, between about 4.8 and about 7.8, between about 4.8 and about 7.6, between about 4.8 and about 7.5, between about 4.8 and about 7.4, between about 4.8 and about 7.2, between about 4.8 and about 7.0, between about 4.8 and about 6.8, between about 4.8 and about 6.6, between about 4.8 and about 6.4, between about 4.8 and about 6.2, between about 4.8 and about 6.0, between about 4.8 and about 5.8, between about 4.8 and about 5.6, between about 4.8 and about 5.4, between about 4.8 and about 5.2, between about 4.8 and about 5.0, between about 5.0 and about 8.5, between about 5.0 and about 8.4, between about 5.0 and about 8.2, between about 5.0 and about 8.0, between about 5.0 and about 7.8, between about 5.0 and about 7.6, between about 5.0 and about 7.5, between about 5.0 and about 7.2, between about 5.0 and about 7.0, between about 5.0 and about 6.8, between about 5.0 and about 6.6, between about 5.0 and about 6.4, between about 5.0 and about 6.2, between about 5.0 and about 6.0, between about 5.0 and about 5.8, between about 5.0 and about 5.6, between about 5.0 and about 5.4, between about 5.0 and about 5.2, between about 5.2 and about 8.5, between about 5.2 and about 8.4, between about 5.2 and about 8.2, between about 5.2 and about 8.0, between about 5.2 and about 7.8, between about 5.2 and about 7.6, between about 5.2 and about 7.5, between about 5.2 and about 7.4, between about 5.2 and about 7.2, between about 5.2 and about 7.0, between about 5.2 and about 6.8, between about 5.2 and about 6.6, between about 5.2 and about 6.4, between about 5.2 and about 6.2, between about 5.2 and about 6.0, between about 5.2 and about 5.8, between about 5.2 and about 5.6, between about 5.2 and about 5.4, between about 5.4 and about 8.5, between about 5.4 and about 8.4, between about 5.4 and about 8.2, between about 5.4 and about 8.0, between about 5.4 and about 7.8, between about 5.4 and about 7.6, between about 5.4 and about 7.5, between about 5.4 and about 7.4, between about 5.4 and about 7.2, between about 5.4 and about 7.0, between about 5.4 and about 6.8, between about 5.4 and about 6.6, between about 5.4 and about 6.4, between about 5.4 and about 6.2, between about 5.4 and about 6.0, between about 5.4 and about 5.8, between about 5.4 and about 5.6, between about 5.6 and about 8.5, between about 5.6 and about 8.4, between about 5.6 and about 8.2, between about 5.6 and about 8.0, between about 5.6 and about 7.8, between about 5.6 and about 7.6, between about 5.6 and about 7.5, between about 5.6 and about 7.4, between about 5.6 and about 7.2, between about 5.6 and about 7.0, between about 5.6 and about 6.8, between about 5.6 and about 6.6, between about 5.6 and about 6.4, between about 5.6 and about 6.2, between about 5.6 and about 6.0, between about 5.6 and about 5.8, between about 5.8 and about 8.5, between about 5.8 and about 8.4, between about 5.8 and about 8.2, between about 5.8 and about 8.0, between about 5.8 and about 7.8, between about 5.8 and about 7.6, between about 5.8 and about 7.5, between about 5.8 and about 7.4, between about 5.8 and about 7.2, between about 5.8 and about 7.0, between about 5.8 and about 6.8, between about 5.8 and about 6.6, between about 5.8 and about 6.4, between about 5.8 and about 6.2, between about 5.8 and about 6.0, between about 6.0 and about 8.5, between about 6.0 and about 8.4, between about 6.0 and about 8.2, between about 6.0 and about 8.0, between about 6.0 and about 7.8, between about 6.0 and about 7.6, between about 6.0 and about 7.5, between about 6.0 and about 7.4, between about 6.0 and about 7.2, between about 6.0 and about 7.0, between about 6.0 and about 6.8, between about 6.0 and about 6.6, between about 6.0 and about 6.4, between about 6.0 and about 6.2, between about 6.2 and about 8.5, between 6.2 and about 8.4, between 6.2 and about 8.2, between 6.2 and about 8.0, between 6.2 and about 7.8, between 6.2 and about 7.6, between about 6.2 and about 7.5, between about 6.2 and about 7.4, between about 6.2 and about 7.2, between about 6.2 and about 7.0, between about 6.2 and about 6.8, between about 6.2 and about 6.6, between about 6.2 and about 6.4, between 6.4 and about 8.5, between 6.4 and about 8.4, between 6.4 and about 8.2, between 6.4 and about 8.0, between 6.4 and about 7.8, between 6.4 and about 7.6, between about 6.4 and about 7.5, between about 6.4 and about 7.4, between about 6.4 and about 7.2, between about 6.4 and about 7.0, between about 6.4 and about 6.8, between about 6.4 and about 6.6, between about 6.6 and about 8.5, between about 6.6 and about 8.4, between 6.6 and about 8.2, between about 6.6 and about 8.0, between about 6.6 and about 7.8, between about 6.6 and about 7.6, between about 6.6 and about 7.5, between about 6.6 and about 7.4, between about 6.6 and about 7.2, between about 6.6 and about 7.0, between about 6.6 and about 6.8, between 6.8 and about 8.5, between 6.8 and about 8.4, between 6.8 and about 8.2, between 6.8 and about 8.0, between 6.8 and about 7.8, between 6.8 and about 7.6, between about 6.8 and about 7.5, between about 6.8 and about 7.4, between about 6.8 and about 7.2, between about 6.8 and about 7.0, between about 7.0 and about 8.5, between about 7.0 and about 8.4, between about 7.0 and about 8.2, between about 7.0 and about 8.0, between about 7.0 and about 7.8, between about 7.0 and about 7.6, between about 7.0 and about 7.5, between about 7.0 and about 7.4, between about 7.0 and about 7.2, between about 7.2 and about 8.5, between about 7.2 and about 8.4, between about 7.2 and about 8.2, between about 7.2 and about 8.0, between about 7.2 and about 7.8, between about 7.2 and about 7.6, between about 7.2 and about 7.5, between about 7.2 and about 7.4, between 7.4 and about 8.5, between about 7.4 and about 8.4, between about 7.4 and about 8.2, between about 7.4 and about 8.0, between about 7.4 and about 7.8, between about 7.4 and about 7.6, between about 7.6 and about 8.5, between about 7.6 and about 8.4, between about 7.6 and about 8.2, between about 7.6 and about 8.0, between about 7.6 and about 7.8, between about 7.8 and about 8.5, between about 7.8 and about 8.4, between about 7.8 and about 8.2, between about 7.8 and about 8.0, between about 8.0 and about 8.5, between about 8.0 and about 8.3, between about 8.0 and about 8.2, between about 8.2 and about 8.5, between about 8.2 and about 8.4, or between about 8.3 and about 8.5.

The fluid including the recombinant antibody that is flowed through a depth filter can include a concentration of recombinant antibody between about 0.01 mg/mL and about 25 mg/mL (e.g., between about 0.01 mg/mL and about 22.5 mg/mL, between about 0.01 mg/mL and about 20.0 mg/mL, between about 0.01 mg/mL and about 17.5 mg/mL, between about 0.01 mg/mL and about 15.0 mg/mL, between about 0.01 mg/mL and about 12.5 mg/mL, between about 0.01 mg/mL and about 10 mg/mL, between about 0.01 mg/mL and about 8 mg/mL, between about 0.01 mg/mL and about 6 mg/mL, between about 0.01 mg/mL and about 5 mg/mL, between about 0.01 mg/mL and about 4 mg/mL, between about 0.01 mg/mL and about 3.5 mg/mL, between about 0.01 mg/mL and about 3.0 mg/mL, between about 0.01 mg/mL and about 2.5 mg/mL, between about 0.01 mg/mL and about 2.0 mg/mL, between about 0.01 mg/mL and about 1.5 mg/mL, between about 0.01 mg/mL and about 1.0 mg/mL, between about 0.01 mg/mL and about 0.5 mg/mL, between about 0.01 mg/mL and about 0.25 mg/mL, between about 0.01 mg/mL and about 0.1 mg/mL, between about 0.1 mg/mL and about 12.5 mg/mL, between about 0.1 mg/mL and about 10.0 mg/mL, between about 0.1 mg/mL and about 8.0 mg/mL, between about 0.1 mg/mL and about 6.0 mg/mL, between about 0.1 mg/mL and about 5.0 mg/mL, between about 0.1 mg/mL and about 4.0 mg/mL, between about 0.1 mg/mL and about 3.5 mg/mL, between about 0.1 mg/mL and about 3.0 mg/mL, between about 0.1 mg/mL and about 2.5 mg/mL, between about 0.1 mg/mL and about 2.0 mg/mL, between about 0.1 mg/mL and about 1.5 mg/mL, between about 0.1 mg/mL and about 1.0 mg/mL, between about 0.1 mg/mL and about 0.5 mg/mL, or between about 0.1 mg/mL and about 0.25 mg/mL).

In some embodiments, a fluid including the recombinant antibody is flowed through the depth filter at a flow rate of between about 25 $L/m^2/h$ and about 400 $L/m^2/h$, between about 25 $L/m^2/h$ and about 390 $L/m^2/h$, between about 25 $L/m^2/h$ and about 380 $L/m^2/h$, between about 25 $L/m^2/h$ and about 360 $L/m^2/h$, between about 25 $L/m^2/h$ and about 340 $L/m^2/h$, between about 25 $L/m^2/h$ and about 320 $L/m^2/h$, between about 25 $L/m^2/h$ and about 300 $L/m^2/h$, between about 25 $L/m^2/h$ and about 280 $L/m^2/h$, between about 25 $L/m^2/h$ and about 260 $L/m^2/h$, between about 25 $L/m^2/h$ and about 240 $L/m^2/h$, between about 25 $L/m^2/h$ and about 220 $L/m^2/h$, between about 25 $L/m^2/h$ and about 200 $L/m^2/h$, between about 25 $L/m^2/h$ and about 180 $L/m^2/h$, between about 25 $L/m^2/h$ and about 160 $L/m^2/h$, between about 25 $L/m^2/h$ and about 140 $L/m^2/h$, between about 25 $L/m^2/h$ and about 120 $L/m^2/h$, between about 25 $L/m^2/h$ and about 100 $L/m^2/h$, between about 25 $L/m^2/h$ and about 80 $L/m^2/h$, between about 25 $L/m^2/h$ and about 60 $L/m^2/h$, between about 25 $L/m^2/h$ and about 40 $L/m^2/h$, between about 25 $L/m^2/h$ and about 35 $L/m^2/h$, between about 40 $L/m^2/h$ and about 400 $L/m^2/h$, between about 40 $L/m^2/h$ and about 380 $L/m^2/h$, between about 40 $L/m^2/h$ and about 360 $L/m^2/h$, between about 40 $L/m^2/h$ and about 340 $L/m^2/h$, between about 40 $L/m^2/h$ and about 320 $L/m^2/h$, between about 40 $L/m^2/h$ and about 300 $L/m^2/h$, between about 40 $L/m^2/h$ and about 280 $L/m^2/h$, between about 40 $L/m^2/h$ and about 260 $L/m^2/h$, between about 40 $L/m^2/h$ and about 240 $L/m^2/h$, between about 40 $L/m^2/h$ and about 220 $L/m^2/h$, between about 40 $L/m^2/h$ and about 220 $L/m^2/h$, between about 40 $L/m^2/h$ and about 200 $L/m^2/h$, between about 40 $L/m^2/h$ and about 180 $L/m^2/h$, between about 40 $L/m^2/h$ and about 160 $L/m^2/h$, between about 40 $L/m^2/h$ and about 140 $L/m^2/h$, between about 40 $L/m^2/h$ and about 120 $L/m^2/h$, between about 40 $L/m^2/h$ and about 100 $L/m^2/h$, between about 40 $L/m^2/h$ and about 80 $L/m^2/h$, between about 40 $L/m^2/h$ and about 60 $L/m^2/h$, between about 40 $L/m^2/h$ and about 50 $L/m^2/h$, between about 60 $L/m^2/h$ and about 400 $L/m^2/h$, between about 60 $L/m^2/h$ and about 380 $L/m^2/h$, between about 60 $L/m^2/h$ and about 360 $L/m^2/h$, between about 60 $L/m^2/h$ and about 340 $L/m^2/h$, between about 60 $L/m^2/h$ and about 320 $L/m^2/h$, between about 60 $L/m^2/h$ and about 300 $L/m^2/h$, between about 60 $L/m^2/h$ and about 280 $L/m^2/h$, between about 60 $L/m^2/h$ and about 260 $L/m^2/h$, between about 60 $L/m^2/h$ and about 240 $L/m^2/h$, between about 60 $L/m^2/h$ and about 220 $L/m^2/h$, between about 60 $L/m^2/h$ and about 200 $L/m^2/h$, between about 60 $L/m^2/h$ and about 180 $L/m^2/h$, between about 70 $L/m^2/h$ and about 150 $L/m^2/h$, between about 70 $L/m^2/h$ and about 180 $L/m^2/h$, between about 60 $L/m^2/h$ and about 160 $L/m^2/h$, between about 60 $L/m^2/h$ and about 140 $L/m^2/h$, between about 60 $L/m^2/h$ and about 120 $L/m^2/h$, between about 60 $L/m^2/h$ and about 100 $L/m^2/h$, between about 60 $L/m^2/h$ and about 80 $L/m^2/h$, between about 80 $L/m^2/h$ and about 400 $L/m^2/h$, between about 80 $L/m^2/h$ and about 380 $L/m^2/h$, between about 80 $L/m^2/h$ and about 360 $L/m^2/h$, between about 80 $L/m^2/h$ and about 340 $L/m^2/h$, between about 80 $L/m^2/h$ and about 320 $L/m^2/h$, between about 80 $L/m^2/h$ and about 300 $L/m^2/h$, between about 80 $L/m^2/h$ and about 280 $L/m^2/h$, between about 80 L/m²/h and about 260 L/m²/h, between about 80 L/m²/h and about 240 L/m²/h, between about 80 L/m²/h and about 220 L/m²/h. between about 80 L/m²/h and about 200 L/m²/h, between about 80 L/m²/h and about 180 L/m²/h, between about 80 L/m²/h and about 160 L/m²/h, between about 80 L/m²/h and about 140 L/m²/h, between about 80 L/m²/h and about 120 L/m²/h, between about 80 L/m²/h and about 100 L/m²/h, between about 100 L/m²/h and about 400 L/m²/h, between about 100 L/m²/h and about 380 L/m²/h, between about 100 L/m²/h and about 360 L/m²/h, between about 100 L/m²/h and about 340 L/m²/h, between about 100 L/m²/h and about 320 L/m²/h, between about 100 L/m²/h and about 300 L/m²/h, between about 100 L/m²/h and about 280 L/m²/h, between about 100 L/m²/h and about 260 L/m²/h, between about 100 L/m²/h and about 240 L/m²/h, between about 100 L/m²/h and about 220 L/m²/h, between about 100 L/m²/h and about 200 L/m²/h, 100 L/m²/h and about 180 L/m²/h, between about 100 L/m²/h and about 160 L/m²/h, between about 100 L/m²/h and about 140 L/m²/h, between about 100 L/m²/h and about 120 L/m²/h, between about 120 L/m²/h and about 400 L/m²/h, between about 120 L/m²/h and about 380 L/m²/h, between about 120 L/m²/h and about 360 L/m²/h, between about 120 L/m²/h and about 340 L/m²/h, between about 120 L/m²/h and about 320 L/m²/h, between about 120 L/m²/h and about 300 L/m²/h, between about 120 L/m²/h and about 280 L/m²/h, between about 120 L/m²/h and about 260 L/m²/h, between about 120 L/m²/h and about 240 L/m²/h, between about 120 L/m²/h and about 220 L/m²/h, between about 120 L/m²/h and about 200 L/m²/h, between about 120 L/m²/h and about 180 L/m²/h, between about 120 L/m²/h and about 160 L/m²/h, between about 120 L/m²/h and about 140 L/m²/h, between about 140 L/m²/h and about 400 L/m²/h, between about 140 L/m²/h and about 380 L/m²/h, between about 140 L/m²/h and about 360 L/m²/h, between about 140 L/m²/h and about 340 L/m²/h, between about 140 L/m²/h and about 320 L/m²/h, between about 140 L/m²/h and about 300 L/m²/h, between about 140 L/m²/h and about 280 L/m²/h, between about 140 L/m²/h and about 260 L/m²/h, between about 140 L/m²/h and about 240 L/m²/h, between about 140 L/m²/h and about 220 L/m²/h, between about 140 L/m²/h and about 200 L/m²/h, between about 140 L/m²/h and about 180 L/m²/h, between about 140 L/m²/h and about 160 L/m²/h, between about 160 L/m²/h and about 400 L/m²/h, between about 160 L/m²/h and about 380 L/m²/h, between about 160 L/m²/h and about 360 L/m²/h, between about 160 L/m²/h and about 340 L/m²/h, between about 160 L/m²/h and about 320 L/m²/h, between about 160 L/m²/h and about 300 L/m²/h, between about 160 L/m²/h and about 280 L/m²/h, between about 160 L/m²/h and about 260 L/m²/h, between about 160 L/m²/h and about 240 L/m²/h, between about 160 L/m²/h and about 220 L/m²/h, between about 160 L/m²/h and about 200 L/m²/h, between about 160 L/m²/h and about 180 L/m²/h, between about 180 L/m²/h and about 400 L/m²/h, between about 180 L/m²/h and about 380 L/m²/h, between about 180 L/m²/h and about 360 L/m²/h, between about 180 L/m²/h and about 340 L/m²/h, between about 180 L/m²/h and about 320 L/m²/h, between about 180 L/m²/h and about 300 L/m²/h, between about 180 L/m²/h and about 280 L/m²/h, between about 180 L/m²/h and about 260 L/m²/h, between about 180 L/m²/h and about 240 L/m²/h, between about 180 L/m²/h and about 220 L/m²/h, between about 180 L/m²/h and about 200 L/m²/h, between about 200 L/m²/h and about 400 L/m²/h, between about 200 L/m²/h and about 380 L/m²/h, between about 200 L/m²/h and about 360 L/m²/h, between about 200 L/m²/h and about 340 L/m²/h, between about 200 L/m²/h and about 320 L/m²/h, between about 200 L/m²/h and about 300 L/m²/h, between about 200 L/m²/h and about 280 L/m²/h, between about 200 L/m²/h and about 260 L/m²/h, between about 200 L/m²/h and about 240 L/m²/h, between about 200 L/m²/h and about 220 L/m²/h, between about 220 L/m²/h and about 400 L/m²/h, between about 220 L/m²/h and about 380 L/m²/h, between about 220 L/m²/h and about 360 L/m²/h, between about 220 L/m²/h and about 340 L/m²/h, between about 220 L/m²/h and about 320 L/m²/h, between about 220 L/m²/h and about 300 L/m²/h, between about 220 L/m²/h and about 280 L/m²/h, between about 220 L/m²/h and about 260 L/m²/h, between about 220 L/m²/h and about 240 L/m²/h, between about 240 L/m²/h and about 400 L/m²/h, between about 240 L/m²/h and about 380 L/m²/h, between about 240 L/m²/h and about 360 L/m²/h, between about 240 L/m²/h and about 340 L/m²/h, between about 240 L/m²/h and about 320 L/m²/h, between about 240 L/m²/h and about 300 L/m²/h, between about 240 L/m²/h and about 280 L/m²/h, between about 240 L/m²/h and about 260 L/m²/h, between about 260 L/m²/h and about 400 L/m²/h, between about 260 L/m²/h and about 380 L/m²/h, between about 260 L/m²/h and about 360 L/m²/h, between about 260 L/m²/h and about 340 L/m²/h, between about 260 L/m²/h and about 320 L/m²/h, between about 260 L/m²/h and about 300 L/m²/h, between about 260 L/m²/h and about 280 L/m²/h, between about 280 L/m²/h and about 400 L/m²/h, between about 280 L/m²/h and about 380 L/m²/h, between about 280 L/m²/h and about 360 L/m²/h, between about 280 L/m²/h and about 340 L/m²/h, between about 280 L/m²/h and about 320 L/m²/h, between about 280 L/m²/h and about 300 L/m²/h, between about 300 L/m²/h and about 400 L/m²/h, between about 300 L/m²/h and about 380 L/m²/h, between about 300 L/m²/h and about 360 L/m²/h. between about 300 L/m²/h and about 340 L/m²/h, between about 300 L/m²/h and about 320 L/m²/h, between about 320 L/m²/h and about 400 L/m²/h, between about 320 L/m²/h and about 380 L/m²/h, between about 320 L/m²/h and about 360 L/m²/h, between about 320 L/m²/h and about 340 L/m²/h, between about 340 L/m²/h and about 400 L/m²/h, between about 340 L/m²/h and about 380 L/m²/h, between about 340 L/m²/h and about 360 L/m²/h, between about 360 L/m²/h and about 400 L/m²/h, between about 360 L/m²/h and about 380 L/m²/h, or between about 380 L/m²/h and about 400 L/m²/h, to selectively retain soluble protein aggregates, such as protein dimers and higher protein oligomers (such as soluble recombinant antibody aggregates). This filtration step is performed using a depth filter including a filtration media of, for example, silica, one or more layers of a fibrous media, one or more layers of charged or surface modified microporous membranes, or a small bed of chromatography media. A depth filter can have, e.g., a membrane surface area of between about 10 cm² and about 32000 cm², between about 10 cm² and about 31000 cm², between about 10 cm² and about 30000 cm², between about 10 cm² and about 29000 cm², between about 10 cm² and about 28000 cm², between about 10 cm² and about 27000 cm², between about 10 cm² and about 26000 cm², between about 10 cm² and about 25000 cm², between about 10 cm² and about 24000 cm², between about 10 cm² and about 23000 cm², between about 10 cm² and about 22000 cm², between about 10 cm² and about 21000 cm², between about 10 cm² and about 20000 cm², between about 10 cm² and about 19000 cm², between about 10 cm² and about 18000 cm², between about 10 cm² and about 17000 cm², between about 10 cm² and about 16000 cm², between about 10 cm² and about 15000 cm², between about 10 cm² and about 14000 cm², between about 10 cm² and about 13000 cm², between about 10 cm² and about 12000 cm², between about 10 cm² and about 11000 cm², between about 10 cm² and about 10000 cm², between about 10 cm² and about 9000 cm², between about 10 cm² and about 8000 cm², between about 10 cm² and about 7000 cm², between about 10 cm² and about 6000 cm², between about 10 cm² and about 5000 cm², between about 10 cm² and about 4000 cm², between about 10 cm² and about 3000 cm², between about 10 cm² and about 2000 cm², between about 10 cm² and about 1500 cm², between about 10 cm² and about 1020 cm², between about 10 cm² and about 1000 cm², between about 10 cm² and about 500 cm², between about 10 cm² and about 75 cm², between about 100 cm² and about 25000 cm², between about 100 cm² and about 24000 cm², between about 100 cm² and about 23000 cm², between about 100 cm² and about 22000 cm², between about 100 cm² and about 21000 cm², between about 100 cm² and about 20000 cm², between about 100 cm² and about 19000 cm², between about 100 cm² and about 18000 cm², between about 100 cm² and about 17000 cm², between about 100 cm² and about 16000 cm², between about 100 cm² and about 15000 cm², between about 100 cm² and about 14000 cm², between about 100 cm² and about 13000 cm², between about 100 cm² and about 12000 cm², between about 100 cm² and about 11000 cm², between about 100 cm² and about 10000 cm², between about 1000 cm² and about 9000 cm², between about 100 cm² and about 8000 cm², between about 100 cm² and about 7000 cm², between about 100 cm² and about 6000 cm², between about 100 cm² and about 5000 cm², between about 100 cm² and about 4000 cm², between about 100 cm² and about 3000 cm², between about 100 cm² and about 2000 cm², between about 100 cm² and about 1000 cm², between about 100 cm² and about 500 cm², between about 500 cm² and about 25000 cm², between about 500 cm² and about 24000 cm², between about 500 cm² and about 23000 cm², between about 500 cm² and about 22000 cm², between about 500 cm² and about 21000 cm², between about 500 cm² and about 20000 cm², between about 500 cm² and about 19000 cm², between about 500 cm² and about 18000 cm², between about 500 cm² and about 17000 cm², between about 500 cm² and about 16000 cm², between about 500 cm² and about 15000 cm², between about 500 cm² and about 14000 cm², between about 500 cm² and about 13000 cm², between about 500 cm² and about 12000 cm², between about 500 cm² and about 11000 cm², between about 500 cm² and about 10000 cm², between about 500 cm² and about 9000 cm², between about 500 cm² and about 8000 cm², between about 500 cm² and about 7000 cm², between about 500 cm² and about 6000 cm², between about 500 cm² and about 5000 cm², between about 500 cm² and about 4000 cm², between about 500 cm² and about 3000 cm², between about 500 cm² and about 2000 cm², between about 500 cm² and about 1000 cm², between about 1000 cm² and about 25000 cm², between about 1000 cm² and about 24000 cm², between about 1000 cm² and about 23000 cm², between about 1000 cm² and about 22000 cm², between about 1000 cm² and about 21000 cm², between about 1000 cm² and about 20000 cm², between about 1000 cm² and about 19000 cm², between about 1000 cm² and about 18000 cm², between about 1000 cm² and about 17000 cm², between about 1000 cm² and about 16000 cm², between about 1000 cm² and about 15000 cm², between about 1000 cm² and about 14000 cm², between about 1000 cm² and about 13000 cm², between about 1000 cm² and about 12000 cm², between about 1000 cm² and about 11000 cm², between about 1000 cm² and about 10000 cm², between about 1000 cm² and about 9000 cm², between about 1000 cm² and about 8000 cm², between about 1000 cm² and about 7000 cm², between about 1000 cm² and about 6000 cm², between about 1000 cm² and about 5000 cm², between about 1000 cm² and about 4000 cm², between about 1000 cm² and about 3000 cm², between about 1000 cm² and about 2000 cm², between about 5000 cm² and about 25000 cm², between about 5000 cm² and about 24000 cm², between about 5000 cm² and about 23000 cm², between about 5000 cm² and about 22000 cm², between about 5000 cm² and about 21000 cm², between about 5000 cm² and about 20000 cm², between about 5000 cm² and about 19000 cm², between about 5000 cm² and about 18000 cm², between about 5000 cm² and about 17000 cm², between about 5000 cm² and about 16000 cm², between about 5000 cm² and about 15000 cm², between about 5000 cm² and about 14000 cm², between about 5000 cm² and about 13000 cm², between about 5000 cm² and about 12000 cm², between about 5000 cm² and about 11000 cm², between about 5000 cm² and about 10000 cm², between about 5000 cm² and about 9000 cm², between about 5000 cm² and about 8000 cm², between about 5000 cm² and about 7000 cm², between about 5000 cm² and about 6000 cm², between about 10000 cm² and about 25000 cm², between about 10000 cm² and about 24000 cm², between about 10000 cm² and about 23000 cm², between about 10000 cm² and about 2200 cm², between about 10000 cm² and about 21000 cm², between about 10000 cm² and about 20000 cm², between about 10000 cm² and about 19000 cm², between about 10000 cm² and about 18000 cm², between about 10000 cm² and about 17000 cm², between about 10000 cm² and about 16000 cm², between about 10000 cm² and about 15000 cm², between about 10000 cm² and about 14000 cm², between about 10000 cm² and about 13000 cm², between about 10000 cm² and about 12000 cm², between about 10000 cm² and about 11000 cm², between about 15000 cm² and about 25000 cm², between about 15000 cm² and about 24000 cm², between about 15000 cm² and about 23000 cm², between about 15000 cm² and about 22000 cm², between about 15000 cm² and about 21000 cm², between about 15000 cm² and about 20000 cm², between about 15000 cm² and about 19000 cm², between about 15000 cm² and about 18000 cm², between about 15000 cm² and about 17000 cm², between about 15000 cm² and about 16000 cm², between about 20000 cm² and about 25000 cm², between about 20000 cm² and about 24000 cm², between about 20000 cm² and about 23000 cm², between about 20000 cm² and about 22000 cm², between about 20000 cm² and about 21000 cm², or about 25 cm². In some examples, two or more depth filters are fluidly connected to a manifold in order to increase the amount of recombinant antibody flowed through a depth filter at one or more steps in a purification process.

The step of flowing the recombinant antibody through a depth filter can result in substantially complete removal of soluble protein aggregates. For example, the step of flowing the recombinant antibody through a depth filter can provide a filtrate that includes the purified recombinant antibody and is substantially free (such as about or at least 90% free, about or at least 90.5% free, about or at least 91.0% free, about or at least 91.5% free, about or at least 92.0% free, about or at least 92.5% free, about or at least 93.0% free, about or at least 93.5% free, about or at least 94.0%, about or at least 94.5% free, about or at least 95.0% free, about or at least 95.5% free, about or at least 96.0% free, about or at least 96.5% free, about or at least 97.0% free, about or at least 97.5% free, about or at least 98.0% free, about or at least 98.5% free, about or at least 99.0% free, about or at least 99.5% free, or about or at least 99.8% free). In some embodiments, the depth filter provides a filtrate that includes the purified recombinant antibody and no detectable soluble protein aggregates.

Methods for detecting the level or amount of protein aggregates are known in the art. For example, size exclusion chromatography, native (non-denaturing) gel chromatography, analytical ultracentrifugation (AUC), field-flow fractionation (FFF), and dynamic light scattering (DLS) can be used to detect the amount of soluble protein aggregates are present in the depth filter filtrate.

In one embodiment of the methods, a constant pressure mode of filtration or a constant flow mode of operation is used. A fluid including a recombinant antibody can be retained by a pressurized reservoir and pumped through a depth filter by the pressure in the reservoir. The fluid is subjected to a normal flow mode of filtration with the aggregates being retained by the depth filter and an aggregate-free fluid is discharged as the filtrate. The filtrate can be passed through a conduit for downstream processing, such as one or more unit operations. By operating in this manner, soluble protein aggregates are retained by the depth filter. Alternatively, a pump located between the reservoir and the depth filter could be used to create constant pressure and maintain constant flow through the depth filter. The fluid including a recombinant antibody is subjected to a normal flow mode of filtration with the aggregates being retained by the depth filter and an aggregate-free fluid discharged as the filtrate from the depth filter. The filtrate can be passed through a conduit for further downstream processing.

Non-limiting depth filters that can be used to remove aggregates are described herein and additional depth filters that can be used are known in the art. Representative suitable depth filters include those formed from fibrous media formed of silica, cellulosic fibers, synthetic fibers or blends thereof, such as CUNO® Zeta PLUS® Delipid filters (3M, St. Paul, MN), CUNO® Emphaze AEX filters (3M, St. Paul, MN), CUNO® 90ZA08A filters (3M, St. Paul, MN), CUNO® DELI08A Delipid filters (3M, St. Paul, MN), Millipore X0HC filters (EMD Millipore, Billerica, MA), MILLISTAK® pads (EMD Millipore, Billerica, MA), microporous membranes that are either charged or have a surface chemistry (such as hydrophilicity or hydrophobicity, or a positive or negative charge as are taught by U.S. Pat. Nos. 5,629,084 and 4,618,533) made from a material selected from the group consisting of regenerated cellulose, polyethersulfone, polyarylsulphone, polysulfone, polyimide, polyamide or polyvinylidenedifluoride (PVDF), such as charged DURAPORE® membrane, hydrophobic DURAPORE® membrane, hydrophobic AERVENT® membrane and INTERCEPT™ Q quaternary charged membrane, all available from EMD Millipore, Billerica, MA One or More Unit Operations Some embodiments of any of the methods described herein include, between the step of capturing and the step of performing viral filtration (e.g., using any of the methods of performing viral filtration described herein), the step of performing one or more (e.g., two, three, four, or five) unit operations on the recombinant antibody, e.g., one or more unit operations selected from the group of filtering (e.g., ultrafiltration/diafiltration to concentrate the recombinant antibody in a fluid), purifying the recombinant antibody, polishing the recombinant antibody, viral inactivation, depth filtration, adjusting (e.g., increasing or decreasing) one or both of the pH and ionic concentration of a fluid including the recombinant antibody, and pre-filtration. Some embodiments of any of the methods described herein include, between the step of capturing and the step of viral filtration, the step of performing one or more (e.g., two, three, four, or five) unit operations on the recombinant antibody, e.g., one or more unit operations from the group of ultrafiltration/diafiltration to concentrate a recombinant protein in a fluid, ion exchange chromatography, hydrophobic interaction chromatography, polishing the recombinant protein, viral inactivation, adjustment of pH, adjustment of ionic strength, adjustment of both pH and ionic strength of a fluid including the recombinant protein, depth filtration, and pre-filtration. In some embodiments of any of the methods described herein, the methods include between the capturing step and the step of viral filtration, performing the sequential unit operations of polishing (e.g., by performing hydrophobic interaction chromatography), viral inactivation, ultrafiltration/diafiltration to concentrate the recombinant antibody, depth filtration, and pre-filtration (e.g., using a Sartorius Virosart® Max pre-filter).

Some embodiments of any of the methods described herein further include performing one or more (e.g., two, three, four, or five) unit operations before the capturing step, e.g., one or more unit operations selected from the group of clarifying a culture medium, filtration (e.g., ultrafiltration/diafiltration to concentrate a recombinant antibody in a fluid), viral inactivation, purifying, and adjusting (e.g., increasing or decreasing) one or both of the pH and ionic concentration of a fluid including the recombinant antibody. Some embodiments of any of the methods described herein further include performing one or more (e.g., two, three, four, or five) unit operations before the capturing step, e.g., one or more unit operations selected from the group of ultrafiltration/diafiltration to concentrate the recombinant antibody in a fluid, ion exchange chromatography, hydrophobic interaction chromatography, polishing the recombinant antibody, viral inactivation, adjustment of pH, adjustment of ionic strength, and adjustment of both pH and ionic strength of a fluid including the recombinant antibody. In some embodiments, the methods further include, prior to the capturing step, the sequential steps of clarification of culture media, ultrafiltration/diafiltration to concentrate the recombinant antibody, and viral inactivation.

Some embodiments further include performing one or more unit operations after the step of viral inactivation, e.g., one or more unit operations selected from the group of purifying the recombinant antibody, polishing the recombinant antibody, adjusting (e.g., increasing or decreasing) one or both of the pH and ionic concentration of a fluid including the purified recombinant antibody, or passing the fluid through an additional virus filter. In some embodiments of any of the methods described herein, the unit operation of viral filtration occurs immediately following the step of flowing the recombinant antibody through the depth filter or immediately following the step of flowing the recombinant antibody through a pre-filter.

Purifying and Polishing the Recombinant Protein

The methods described herein can include a step of purifying the recombinant antibody using at least one chromatography column that can be used to perform the unit operation of purifying a recombinant protein. The methods described herein can include a step of polishing the recombinant antibody using at least one chromatography column or chromatographic membrane that can be used to perform the unit operation of polishing the recombinant protein.

The at least one chromatography column for purifying the recombinant antibody can include a resin that utilizes a capture mechanism (such as any of the capture mechanisms described herein or known in the art), or a resin that can be used to perform anion exchange, cation exchange, or molecular sieve chromatography. The at least one chromatography column or chromatographic membrane for polishing the recombinant antibody can include a resin can be used to perform anion exchange, cation exchange, or molecular sieve chromatography (such as any of the exemplary resins for performing anion exchange, cation exchange, or molecular sieve chromatography known in the art).

The size, shape, and volume of the at least one chromatography column for purifying the recombinant antibody, and/or the size and shape of the at least one chromatography column or chromatographic membrane for polishing the recombinant antibody can any of combination of the exemplary sizes, shapes, and volumes of chromatography columns or chromatographic membranes described herein or known in the art. Purifying or polishing a recombinant antibody can, e.g., include the steps of loading, washing, eluting, and equilibrating the at least one chromatography column or chromatographic membrane used to perform the unit of operation of purifying or polishing the recombinant antibody. Typically, the elution buffer coming out of a chromatography column or chromatographic membrane used for purifying includes the recombinant antibody. Typically, the loading and/or wash buffer coming out of a chromatography column or chromatographic membrane used for polishing includes the recombinant antibody.

For example, the size of the chromatography column for purifying the recombinant antibody can have a volume of, e.g., between about 1.0 mL and about 650 L (e.g., between about 5.0 mL and about 600 L, between about 5.0 mL and about 550 L, between about 5.0 mL and about 500 L, between about 5.0 mL and about 450 L, between about 5.0 mL and about 400 L, between about 5.0 mL and about 350 L, between about 5.0 mL and about 300 L, between about 5.0 mL and about 250 L, between about 5.0 mL and about 200 L, between about 5.0 mL and about 150 L, between about 5.0 mL and about 100 L, between about 5.0 mL and about 50 L, between about 5.0 mL and about 10 L, between about 5.0 mL and about 1.0 L, between about 5.0 mL and about 900 mL, between about 5.0 mL and about 800 mL, between about 5.0 mL and about 700 mL, between about 5.0 mL and about 600 mL, between about 5.0 mL and about 500 mL, between about 5.0 mL and about 400 mL, between about 5.0 mL and about 300 mL, between about 5.0 mL and about 200 mL, between about 5.0 mL and about 180 mL, between about 5.0 mL and about 160 mL, between about 5.0 mL and about 140 mL, between about 5.0 mL and about 120 mL, between about 5.0 mL and about 100 mL, between about 5.0 mL and about 80 mL, between about 5.0 mL and about 60 mL, between about 5.0 mL and about 40 mL, between about 5.0 mL and about 30 mL, or between about 5.0 mL and about 25 mL).

The linear flow rate of the fluid including the recombinant antibody as it is loaded onto the at least one chromatography column for purifying the recombinant antibody can be, e.g., between 50 cm/hour and about 600 cm/hour, between about 50 cm/hour and about 550 cm/hour, between about 50 cm/hour and about 500 cm/hour, between about 50 cm/hour and about 450 cm/hour, between about 50 cm/hour and about 400 cm/hour, between about 50 cm/hour and about 350 cm/hour, between about 50 cm/hour and about 300 cm/hour, between about 50 cm/hour and about 250 cm/hour, between about 50 cm/hour and about 200 cm/hour, between about 50 cm/hour and about 150 cm/hour, or between about 50 cm/hour and about 100 cm/hour (e.g., for a chromatography column have a diameter of between about 100 cm and about 200 cm). The concentration of the recombinant antibody loaded onto the chromatography column for purifying the recombinant antibody can be, e.g., between about 0.05 mg/mL and about 90 mg/mL recombinant antibody (e.g., between about 0.1 mg/mL and about 90 mg/mL, between about 0.1 mg/mL and about 80 mg/mL, between about 0.1 mg/mL and about 70 mg/mL, between about 0.1 mg/mL and about 60 mg/mL, between about 0.1 mg/mL and about 50 mg/mL, between about 0.1 mg/mL and about 40 mg/mL, between about 0.1 mg/mL and about 30 mg/mL, between about 0.1 mg/mL and about 20 mg/mL, between 0.5 mg/mL and about 20 mg/mL, between about 0.1 mg/mL and about 15 mg/mL, between about 0.5 mg/mL and about 15 mg/mL, between about 0.1 mg/mL and about 10 mg/mL, or between about 0.5 mg/mL and about 10 mg/mL recombinant antibody). The resin in the at least one chromatography column for purifying can be an anion exchange or cation exchange chromatography resin. The resin in the at least one chromatography column or chromatographic membrane that is used to perform the unit operation of purifying can be a cationic exchange resin.

Following the loading of the recombinant antibody, the at least one chromatographic column or chromatographic membrane is washed with at least one washing buffer. As can be appreciated in the art, the at least one (e.g., two, three, or four) washing buffer is meant to elute all proteins that are not the recombinant protein from the at least one chromatography column, while not disturbing the interaction of the recombinant antibody with the resin or otherwise eluting the recombinant antibody.

The wash buffer can be passed through the at least one chromatography column at a linear flow rate of, e.g., between 50 cm/hour and about 600 cm/hour, between about 50 cm/hour and about 550 cm/hour, between about 50 cm/hour and about 500 cm/hour, between about 50 cm/hour and about 450 cm/hour, between about 50 cm/hour and about 400 cm/hour, between about 50 cm/hour and about 350 cm/hour, between about 50 cm/hour and about 300 cm/hour, between about 50 cm/hour and about 250 cm/hour, between about 50 cm/hour and about 200 cm/hour, between about 50 cm/hour and about 150 cm/hour, or between about 50 cm/hour and about 100 cm/hour (e.g., for a chromatography column have a diameter of between about 100 cm and about 200 cm). The volume of wash buffer used (such as the combined total volume of wash buffer used when more than one wash buffer is used) can be between about 1× column volume (CV) and about 10×CV, between about 1×CV and about 9×CV, about 1×CV and about 8×CV, about 1×CV and about 7×CV, about 1×CV and about 6×CV, about 2×CV and about 10×CV, about 3×CV and about 10×CV, about 4×CV and about 10×CV, about 2.5×CV and about 5.0×CV, about 5×CV and about 10×CV, or about 5×CV and about 8×CV). The total time of the washing can be between about 2 minutes and about 5 hours (e.g., between about 5 minutes and about 4.5 hours, between about 5 minutes and about 4.0 hours, between about 5 minutes and about 3.5 hours, between about 5 minutes and about 3.0 hours, between about 5 minutes and about 2.5 hours, between about 5 minutes and about 2.0 hours, between about 5 minutes and about 1.5 hours, between about 10 minutes and about 1.5 hours, between about 10 minutes and about 1.25 hours, between about 20 minutes and about 1.25 hours, between about 30 minutes and about 1 hour, between about 2 minutes and 10 minutes, between about 2 minutes and 15 minutes, or between about 2 minutes and 30 minutes).

Following washing of the at least one chromatographic column for purifying the recombinant antibody, the recombinant antibody is eluted by passing an elution buffer through the column. The elution buffer can be passed through the column that can be used to perform the unit operation of purifying the recombinant antibody at a liner flow rate of, e.g., between about 25 cm/hour and about 600 cm/hour, between about 25 cm/hour and about 550 cm/hour, between about 25 cm/hour and about 500 cm/hour, between about 25 cm/hour and about 450 cm/hour, between about 25 cm/hour and about 400 cm/hour, between about 25 cm/hour and about 350 cm/hour, between about 25 cm/hour and about 300 cm/hour, between about 25 cm/hour and about 250 cm/hour, between about 25 cm/hour and about 200 cm/hour, between about 25 cm/hour and about 150 cm/hour, or between about 25 cm/hour and about 100 cm/hour (e.g., for a chromatography column have a diameter of between about 100 cm and about 200 cm). The volume of elution buffer used to elute the recombinant antibody from each the at least one chromatographic column for purifying the recombinant antibody can be between about 1× column volume (CV) and about 10×CV, between about 1×CV and about 9×CV, between about 1×CV and about 8×CV, between about 1×CV and about 7×CV, about 1×CV and about 6×CV, about 1×CV and about 5×CV, about 1×CV and about 4×CV, about 2×CV and about 10×CV, about 3×CV and about 10×CV, about 4×CV and about 10×CV, about 5×CV and about 10×CV, or about 5×CV and about 9×CV. The total time of the eluting can be between about 5 minutes and about 3 hours, between about 5 minutes and about 2.5 hours, between about 5 minutes and about 2.0 hours, between about 5 minutes and about 1.5 hours, between about 5 minutes and about 1.5 hours, between about 5 minutes and about 1.25 hours, between about 5 minutes and about 1.25 hours, between about 5 minutes and about 1 hour, between about 5 minutes and about 40 minutes, between about 10 minutes and about 40 minutes, between about 20 minutes and about 40 minutes, or between about 30 minutes and 1.0 hour. Non-limiting examples of elution buffers that can be used in these methods will depend on the resin and/or the therapeutic antibody. For example, an elution buffer can include a different concentration of salt (e.g., increased salt concentration), a different pH (e.g., an increased or decreased salt concentration), or a molecule that will compete with the recombinant antibody for binding to the resin. Examples of such elution buffers for each of the exemplary capture mechanisms described herein are well known in the art.

Following the elution, and before the next volume of fluid including a recombinant antibody can be loaded onto the at least one chromatographic column, the at least one chromatography column or chromatographic membrane must be equilibrated using a regeneration buffer. The regeneration buffer can be passed through the chromatography column at a linear flow rate of, e.g., between about 25 cm/hour and about 600 cm/hour, between about 25 cm/hour and about 550 cm/hour, between about 25 cm/hour and about 500 cm/hour, between about 25 cm/hour and about 450 cm/hour, between about 25 cm/hour and about 400 cm/hour, between about 25 cm/hour and about 350 cm/hour, between about 25 cm/hour and about 300 cm/hour, between about 25 cm/hour and about 250 cm/hour, between about 25 cm/hour and about 200 cm/hour, between about 25 cm/hour and about 150 cm/hour, or between about 25 cm/hour and about 100 cm/hour (e.g., for a chromatography column have a diameter of between about 100 cm and about 200 cm). The volume of regeneration buffer used for equilibration can be, e.g., between about 1× column volume (CV) and about 10×CV, between about 1×CV and about 9×CV, between about 1×CV and about 8×CV, between about 1×CV and about 7×CV, between about 1×CV and about 6×CV, between about 2×CV and about 10×CV, between about 3×CV and about 10×CV, between about 2×CV and about 5×CV, between about 2.5×CV and about 7.5×CV, between about 4×CV and about 10×CV, between about 5×CV and about 10×CV, or between about 5×CV and about 10×CV. The concentration of recombinant antibody in a fluid used to perform the unit operation of purifying the recombinant antibody can be between about 0.05 mg/mL and about 90 mg/mL, between about 0.1 mg/mL and about 90 mg/mL, between about 0.1 mg/mL and about 80 mg/mL, between about 0.1 mg/mL and about 70 mg/mL, between about 0.1 mg/mL and about 60 mg/mL, between about 0.1 mg/mL and about 50 mg/mL, between about 0.1 mg/mL and about 40 mg/mL, between about 2.5 mg/mL and about 7.5 mg/mL, between about 0.1 mg/mL and about 30 mg/mL, between about 0.1 mg/mL and about 20 mg/mL, between 0.5 mg/mL and about 20 mg/mL, between about 0.1 mg/mL and about 15 mg/mL, between about 0.5 mg/mL and about 15 mg/mL, between about 0.1 mg/mL and about 10 mg/mL, or between about 0.5 mg/mL and about 10 mg/mL recombinant antibody.

The at least one chromatography column or chromatography membrane that can be used to perform the unit operation of polishing the recombinant antibody can include a resin that can be used to perform cation exchange, anion exchange, hydrophobic, mixed-mode, or molecular sieve chromatography. As can be appreciated in the art, polishing can include the steps of loading, chasing, and regenerating the chromatography column or chromatographic membrane. For example, when the steps of loading, chasing, and regenerating are used to perform the polishing, the recombinant antibody does not bind the resin in the at least one chromatography column or chromatography membrane, and the recombinant protein is eluted from the chromatography column or chromatographic membrane in the loading and chasing steps, and the regenerating step is used to remove any impurities from the chromatography column or chromatographic membrane. Exemplary linear flow rates and buffer volumes to be used in each of the loading, chasing, and regenerating steps are described below.

The size, shape, and volume of the chromatography column or chromatography membrane for polishing the recombinant antibody can any of combination of the exemplary sizes, shapes, and volumes of chromatography columns or chromatographic membranes described herein. For example, the size of the at least one chromatography column or chromatographic membrane can have a volume between about 2.0 mL and about 650 L, between about 2.0 mL and about 600 L, between about 2.0 mL and about 550 L, between about 2.0 mL and about 500 L, between about 2.0 mL and about 450 L, between about 2.0 mL and about 400 L, between about 2.0 mL and about 350 L, between about 2.0 mL and about 300 L, between about 2.0 mL and about 250 L, between about 2.0 mL and about 200 L, between about 2.0 mL and about 150 L, between about 2.0 mL and about 100 L, between about 2.0 mL and about 50 L, between about 2.0 mL and about 25 L, between about 2.0 mL and about 10 L, between about 2.0 L and about 5 L, between about 2.0 mL and about 2 L, between about 2.0 mL and about 1 L, between about 2.0 mL and about 800 mL, between about 2.0 mL and about 600 mL, between about 2.0 mL and about 400 mL, between about 2.0 mL and about 200 mL, between about 2.0 mL and about 180 mL, between about 2.0 mL and about 160 mL, between about 2.0 mL and about 140 mL, between about 2.0 mL and about 120 mL, between about 2.0 mL and about 100 mL, between about 2.0 mL and about 80 mL, between about 2.0 mL and about 60 mL, between about 2.0 mL and about 40 mL, between about 2.0 mL and about 40 mL, between about 2.0 mL and about 30 mL, between about 5.0 mL and about 30 mL, between about 2.0 mL and about 25 mL, between about 2.0 mL and about 10 mL, or between about 2.0 mL and about 5 mL. The at least one chromatography column can also be described in terms of its diameter. For example, the at least one chromatography column provided herein can have a diameter of between about 1 cm and about 200 cm, between about 1 cm and about 180 cm, between about 1 cm and about 160 cm, between about 1 cm and about 140 cm, between about 1 cm and about 120 cm, between about 1 cm and about 100 cm, between about 1 cm and about 80 cm, between about 1 cm and about 60 cm, between about 1 cm and about 40 cm, between about 1 cm and about 20 cm, or between about 1 cm and about 10 cm. The linear flow rate of the fluid including the recombinant antibody as it is loaded onto the chromatography column or chromatographic membrane can be between about 25 cm/hour and about 600 cm/hour, between about 25 cm/hour and about 550 cm/hour, between about 25 cm/hour and about 500 cm/hour, between about 25 cm/hour and about 450 cm/hour, between about 25 cm/hour and about 400 cm/hour, between about 25 cm/hour and about 350 cm/hour, between about 25 cm/hour and about 300 cm/hour, between about 25 cm/hour and about 250 cm/hour, between about 25 cm/hour and about 200 cm/hour, between about 25 cm/hour and about 150 cm/hour, or between about 25 cm/hour and about 100 cm/hour (e.g., for a chromatography column have a diameter of between about 100 cm and about 200 cm). The amount of recombinant protein loaded per mL of resin can be between about 5 mg/mL and about 250 mg/mL, between about 5 mg/mL and about 200 mg/mL, between about 5 mg/mL and about 150 mg/mL, between about 5 mg/mL and about 100 mg/mL, between about 5 mg/mL and about 80 mg/mL, between about 5 mg/mL and about 60 mg/mL, between about 5 mg/mL and about 40 mg/mL, between about 5 mg/mL and about 20 mg/mL, between about 5 mg/mL and about 15 mg/mL, or between about 5 mg/mL and about 10 mg/mL. The resin in the chromatography column or chromatographic membrane for polishing can be an anion exchange or cation exchange resin. The resin can be, e.g., a cationic exchange resin.

Following the loading step, a chasing step is performed. For example, a chase buffer can be passed through the at least one chromatography membrane or chromatographic membrane to collect the recombinant antibody that does not substantially bind to the column or membrane). In these examples, the chase buffer can be passed through the column or membrane at a linear flow rate of between about 25 cm/hour and about 600 cm/hour, between about 25 cm/hour and about 550 cm/hour, between about 25 cm/hour and about 500 cm/hour, between about 25 cm/hour and about 450 cm/hour, between about 25 cm/hour and about 400 cm/hour, between about 25 cm/hour and about 350 cm/hour, between about 25 cm/hour and about 300 cm/hour, between about 25 cm/hour and about 250 cm/hour, between about 25 cm/hour and about 200 cm/hour, between about 25 cm/hour and about 150 cm/hour, or between about 25 cm/hour and about 100 cm/hour (e.g., for a chromatography column have a diameter of between about 100 cm and about 200 cm). The volume of chase buffer used can be between about 1× column volume (CV) and about 20×CV, between about 1×CV and about 15×CV, between about 5×CV and about 20×CV, between about 1×CV and about 14×CV, about 1×CV and about 13×CV, about 1×CV and about 12×CV, about 1×CV and about 11×CV, about 2×CV and about 11×CV, about 3×CV and about 11×CV, about 4×CV and about 11×CV, about 2.5×CV and about 5.0×CV, about 5×CV and about 11×CV, or about 5×CV and about 10×CV. The total time of the chasing can be between about 2 minutes and about 3 hours, between about 2 minutes and about 2.5 hours, between about 2 minutes and about 2.0 hours, between about 2 minutes and about 1.5 hours, between about 2 minutes and about 1.25 hours, between about 2 minute and about 5 minutes, between about 2 minute and about 10 minutes, between about 2 minutes and about 4 minutes, between about 30 minutes and about 1 hour, between about 2 minutes and 15 minutes, or between about 2 minutes and 30 minutes. The combined concentration of recombinant antibody present in the filtrate coming through the column in the loading step and the chasing step can be between about 0.1 mg/mL and about 250 mg/mL recombinant antibody, between about 0.1 mg/mL and about 200 mg/mL recombinant antibody, between about 0.1 mg/mL and about 150 mg/mL recombinant antibody, between about 0.1 mg/mL and about 100 mg/mL recombinant antibody, between about 0.1 mg/mL and about 80 mg/mL recombinant antibody, between about 0.1 mg/mL and about 70 mg/mL recombinant antibody, between about 0.1 mg/mL and about 60 mg/mL recombinant antibody, between about 0.1 mg/mL and about 50 mg/mL recombinant antibody, between about 0.1 mg/mL and about 40 mg/mL recombinant antibody, between about 2.5 mg/mL and about 7.5 mg/mL recombinant antibody, between about 0.1 mg/mL and about 30 mg/mL recombinant antibody, between about 0.1 mg/mL and about 20 mg/mL recombinant antibody, between 0.5 mg/mL and about 20 mg/mL recombinant antibody, between about 0.1 mg/mL and about 15 mg/mL recombinant antibody, between about 0.5 mg/mL and about 15 mg/mL recombinant antibody, between about 0.1 mg/mL and about 10 mg/mL recombinant antibody, between about 0.5 mg/mL and about 10 mg/mL recombinant antibody, or between about 1 mg/mL and about 5 mg/mL recombinant antibody.

Following the chasing step and before the next volume of fluid is loaded, the column or membrane must be regenerated using a regeneration buffer. Regeneration buffer can be passed through the column or membrane for polishing at a linear flow rate of between about 25 cm/hour and about 600 cm/hour, between about 25 cm/hour and about 550 cm/hour, between about 25 cm/hour and about 500 cm/hour, between about 25 cm/hour and about 450 cm/hour, between about 25 cm/hour and about 400 cm/hour, between about 25 cm/hour and about 350 cm/hour, between about 25 cm/hour and about 300 cm/hour, between about 25 cm/hour and about 250 cm/hour, between about 25 cm/hour and about 200 cm/hour, between about 25 cm/hour and about 150 cm/hour, or between about 25 cm/hour and about 100 cm/hour. The volume of regeneration buffer used to regenerate can be between about 1× column volume (CV) and about 20×CV, between about 1×CV and about 15×CV, between about 5×CV and about 20×CV, between about 1×CV and about 14×CV, about 1×CV and about 13×CV, about 1×CV and about 12×CV, about 1×CV and about 11×CV, about 2×CV and about 11×CV, about 3×CV and about 11×CV, about 4×CV and about 11×CV, about 2.5×CV and about 5.0×CV, about 5×CV and about 11×CV, or about 5×CV and about 10×CV.

In other examples, the one or more chromatography column(s) and/or chromatographic membranes used to perform the unit operation of polishing include a resin that selectively binds or retains impurities present in a fluid including the recombinant antibody, and instead of regenerating the one or more column(s) and/or membrane(s), the one or more column(s) and/or membrane(s) are replaced (such as with a similar column or membrane) once the binding capacity of the resin in the one or more column(s) and/or membrane(s) has been reached or is substantially close to being reached.

Inactivation of Viruses and Viral Filtration

The unit operation of inactivating viruses present in a fluid including the recombinant antibody can be performed using a chromatography column, a chromatography membrane, or a holding tank that is capable of incubating a fluid including the recombinant antibody at a pH of between about 3.0 to 5.0, between about 3.5 and about 4.5, between about 3.5 and about 4.25, between about 3.5 and about 4.0, between about 3.5 and about 3.8, or about 3.75 for a period of at least 25 minutes, a period of between about 30 minutes to 1.5 hours, a period of between about 30 minutes to 1.25 hours, a period of between about 0.75 hours to 1.25 hours, or a period of about 1 hour.

The unit operation of viral filtration can be performed using any of the methods of performing viral filtration described herein.

Adjusting the pH and/or Ionic Concentration

Some methods described herein can include one or more steps of adjusting (e.g., increasing or decreasing) the pH and/or ionic concentration of a fluid including the recombinant antibody. As described herein, the pH and/or ionic concentration of a fluid including the recombinant antibody can be adjusted (e.g., increased or decreased) by adding a buffer to the fluid (e.g., through the use of an in-line buffer adjustment reservoir).

Formulating the Purified Recombinant Antibody

Some embodiments of any of the methods described herein further include a step of formulating the recombinant antibody into a pharmaceutical composition. For example, formulating can include adding a pharmaceutically acceptable excipient to the purified recombinant antibody (e.g., produced by any of the methods of purifying or manufacturing a recombinant antibody described herein). Formulating can include mixing a pharmaceutically acceptable excipient with the purified recombinant antibody. Examples of pharmaceutically acceptable excipients (e.g., non-naturally occurring pharmaceutically acceptable excipients) are well known in the art. In some embodiments, the purified recombinant antibody is formulated for intravenous, intraarterial, subcutaneous, intraperitoneal, or intramuscular administration.

EXAMPLES

Several general protocols are described below, which may be used in any of the methods described herein and do not limit the scope of the invention described in the claims.

Example 1. Effect of Different Pre-Filters, pH, Arginine Concentration, and Sodium Chloride Concentration on Viral Filtration of BNJ441 Antibody A set of experiments were performed in order to test the effect of different pre-filters, pH, arginine concentration, and sodium chloride concentration on viral filtration. In these experiments, a variety of different fluids having a pH of between 5.5 to 7.6, a sodium chloride concentration of between 65 mM to 300 mM, an L-arginine concentration of 0 or 50 mM, and between 2.91 mg/mL to 3.54 mg/mL of BNJ441 monoclonal antibody that have been pre-filtered with either a 0.1 µm pre-filter or a Sartorius Virosart® Max pre-filter, where each flowed through a Virosart® CPV virus filter. The flux decay and the flow through (g/m²) of the Virosart® CPV filter as each fluid was flowed through the Virosart® CPV filter was determined.

Figure 1:
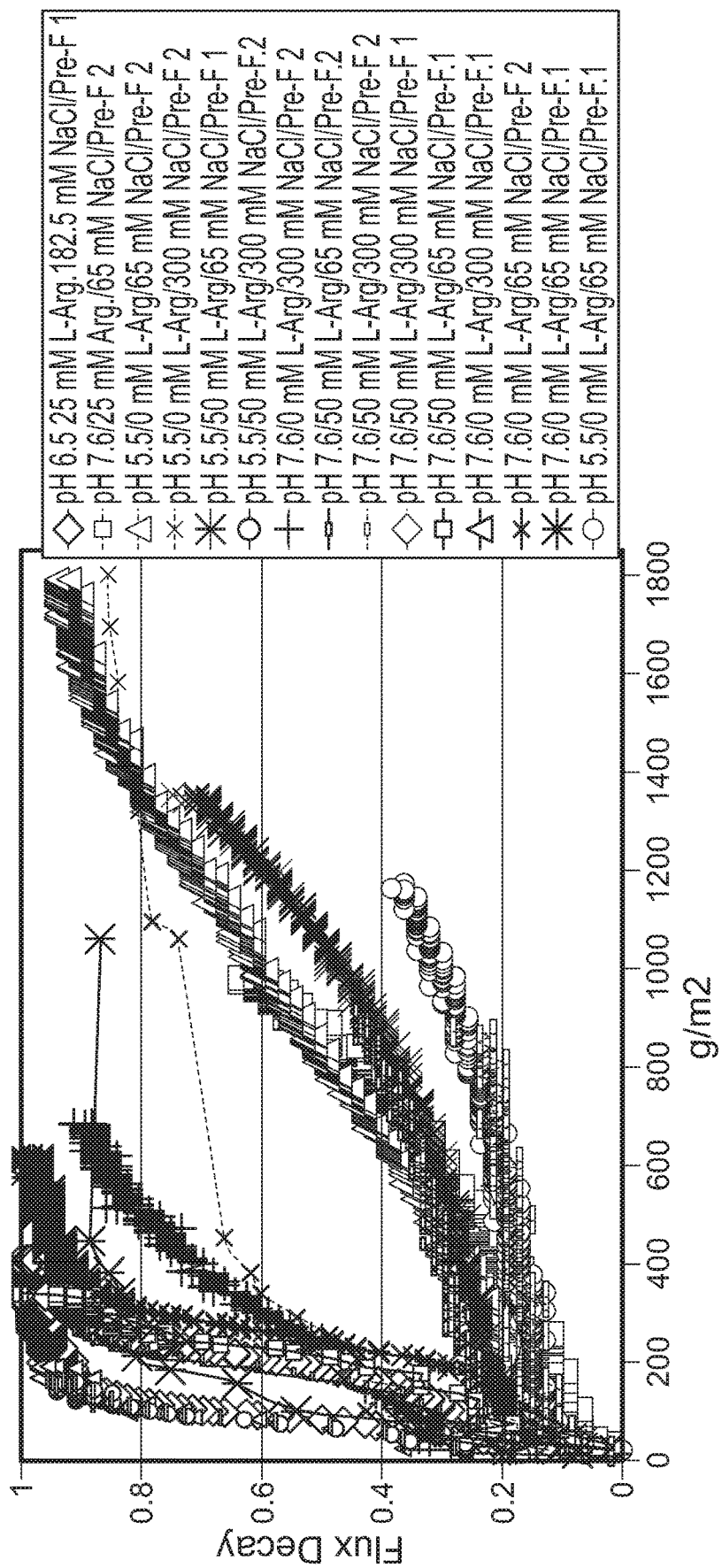
FIG. 1 is graph showing the flux decay as compared to the throughput of a Virosart® CPV virus filter when a fluid containing between 2.91 mg/mL to 3.54 mg/mL of BNJ441 human monoclonal antibody, between 65 mM to 300 mM sodium chloride, and 0 or 50 mM L-arginine, and having a pH of between 5.5 and 7.6 is passed through the filter. Each fluid passed through the Virosart® CPV virus filter had first been pre-filtered using a 0.1 µm filter or a Sartorius Virosart® Max pre-filter.
Figures 3, 4:
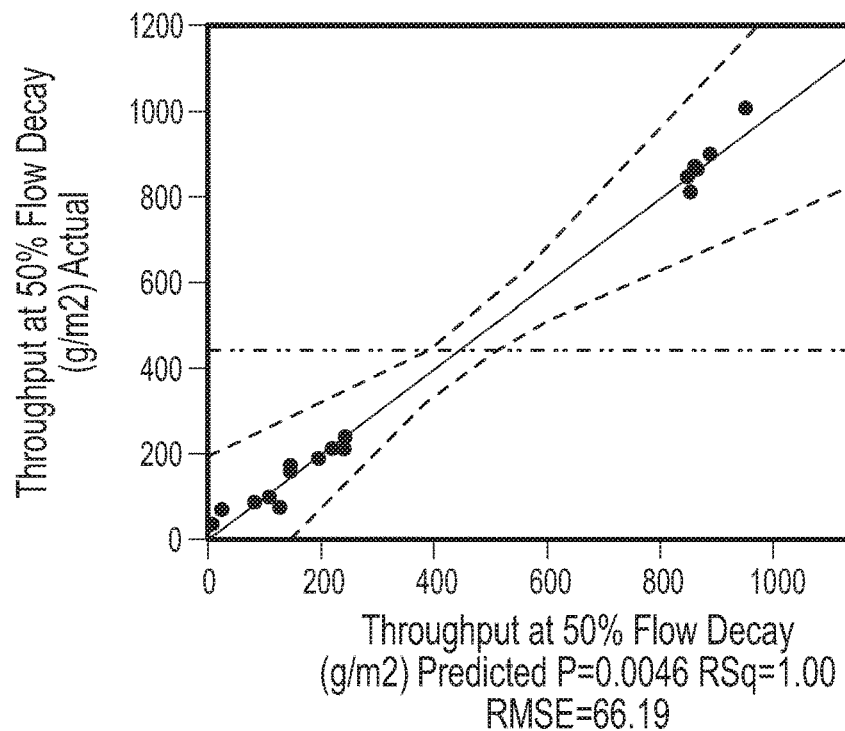
FIG. 3 is a graph showing the relationship of the actual Virosart® CPV virus filter throughput at the time point at which 50% flow decay observed when fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that have been pre-filtered using a 0.1 µm or a Sartorius Virosart® Max pre-filter, are passed through the Virosart® CPV virus filter, to the predicted throughput at 50% flow decay for a Virosart® CPV virus filter using statistical analysis.
FIG. 4 is a graph showing the significance of different parameters on the Virosart® CPV virus filter throughput at the time point at which 50% flow decay is observed (derived from data gathered from flowing fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that have been pre-filtered using a 0.1 µm or a Sartorius Virosart® Max pre-filter, through a Virosart® CPV virus filter).
Figure 5:
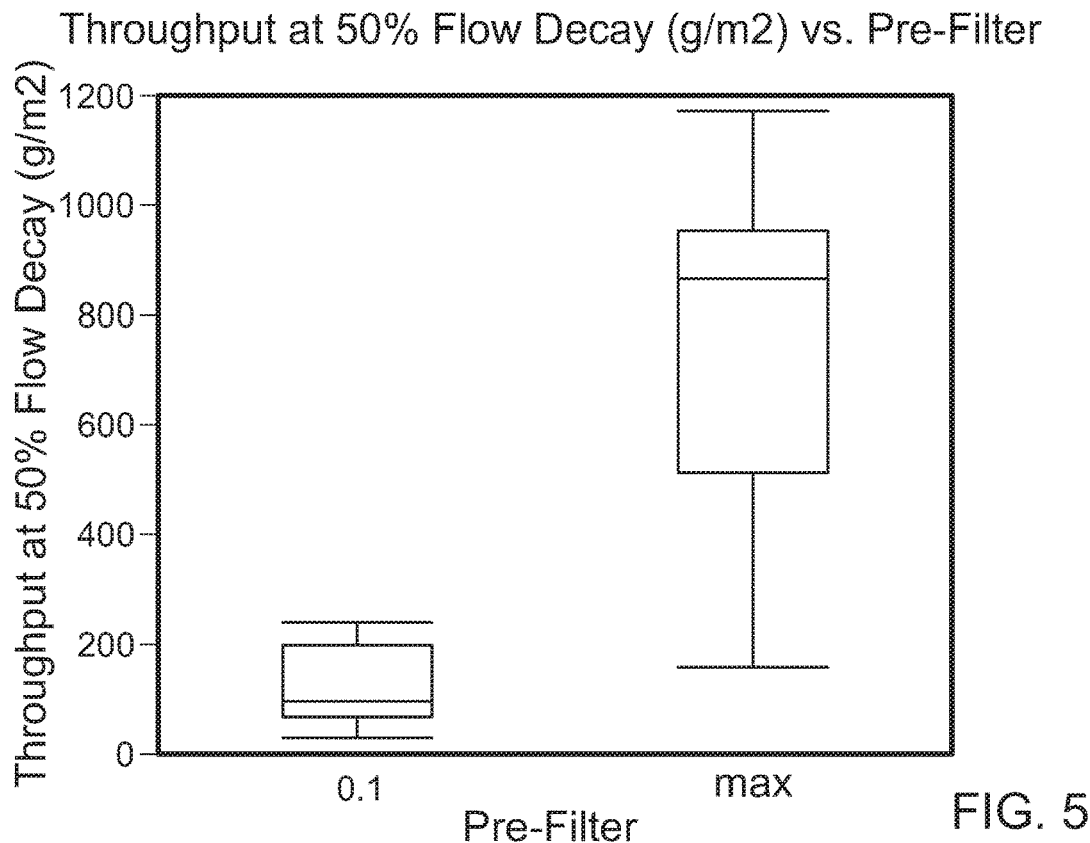
FIG. 5 is a graph showing the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using a 0.1 µm filter (left bar) or a Sartorius Virosart® Max pre-filter (right bar).

The data show that better Virosart® CPV virus filter throughput was observed for fluids that were prefiltered using a Sartorius Virosart® Max pre-filter and also generally fluids having a pH of 5.5 and not including any L-arginine or fluids having a pH of 7.6 and including 25 mM arginine (see, FIGS. 1 and 2). Statistical analysis was used to predict the throughput at 50% flow decay for a Virosart® CPV virus filter (FIG. 3) using the parameters listed in FIG. 4. The data in FIG. 4 also show that the type of pre-filter significantly effects the virus filter throughput. The data in FIG. 5 show that the average throughput of the virus filter at 50% flow decay is increased in fluids that have been pre-filtered using a Sartorius Virosart® Max pre-filter (as compared to fluids that have been pre-filtered using a 0.1 µm-filter).

Figure 6:
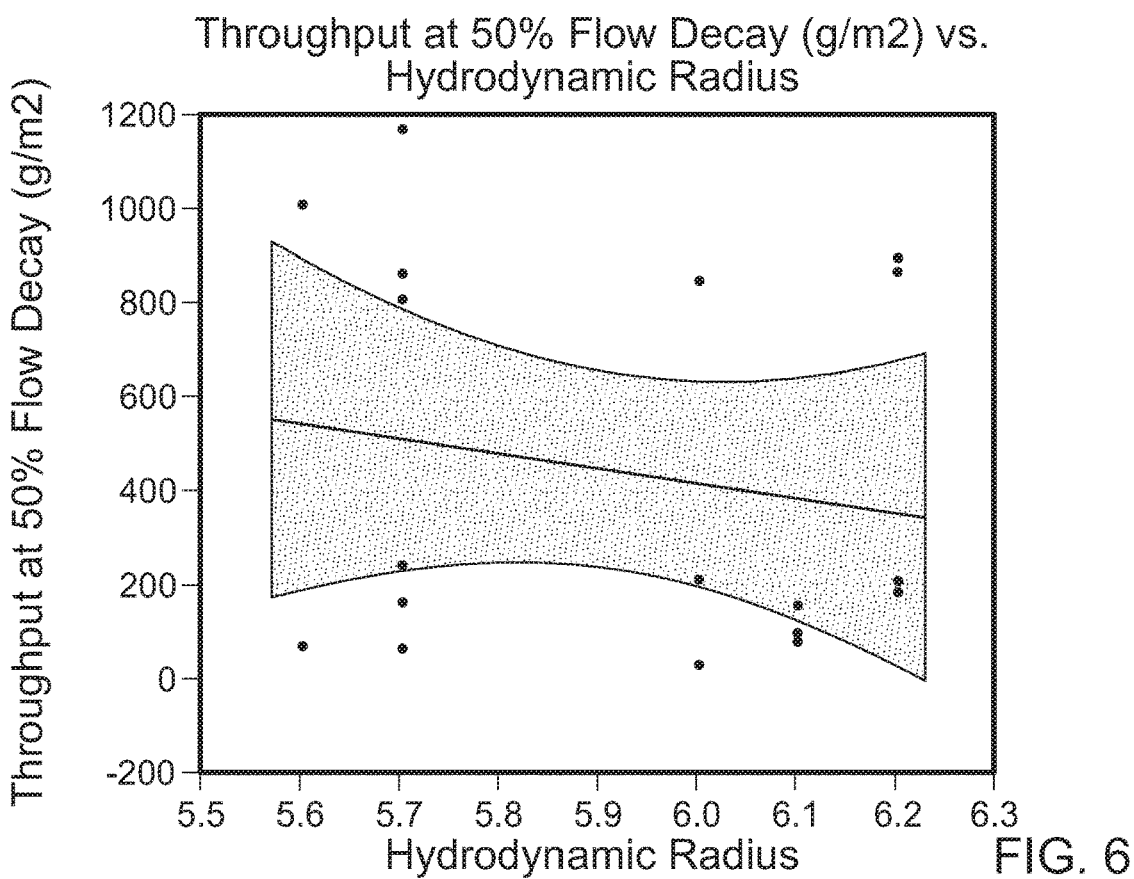
FIG. 6 is a graph showing the relationship of the throughput at 50% flow decay for a Virosart® CPV virus filter for fluids including between 2.91 mg/mL to 3.54 mg/mL BNJ441 human monoclonal antibody, between 65 mM to 300 mM sodium chloride, and 0 or 50 mM L-arginine, and having a pH of between 5.5 and 7.6, that were either pre-filtered using a 0.1 µm filter or a Sartorius Virosart® Max pre-filter, to the hydrodynamic radius of BNJ441 human monoclonal antibody measured in each fluid.

FIG. 6 shows the relationship of the virus filter throughput at 50% flow decay to the hydrodynamic radius of the BNJ441 monoclonal antibody. The data in FIG. 6 shows that as the hydrodynamic radius decreases, the throughput of the virus filter increases.

Figure 7:
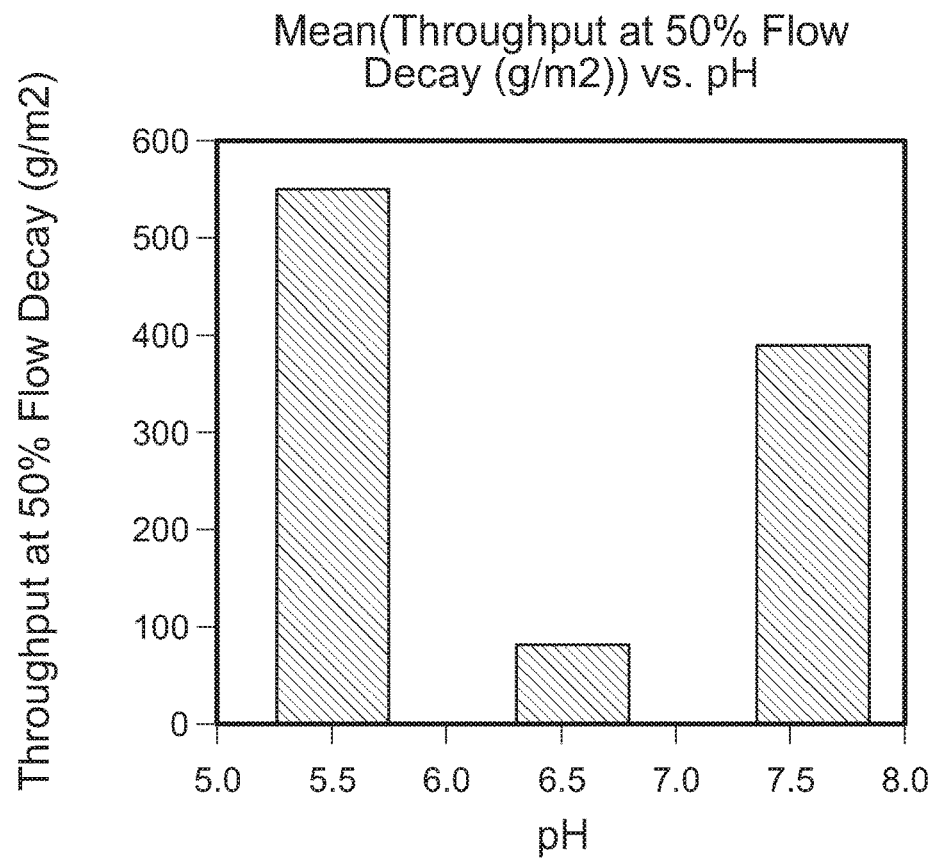
FIG. 7 is a graph showing the mean throughput at 50% flow decay for a Virosart® CPV virus filter for fluids having a pH of 5.5, 6.5 or 7.5, and including between 2.91 mg/mL to 3.54 mg/mL BNJ441 human monoclonal antibody, between 65 mM to 300 mM sodium chloride, and 0 or 50 mM L-arginine, and the fluids having been either pre-filtered using a 0.1 μm filter or a Sartorius Virosart® Max pre-filter.

FIG. 7 shows the throughput of the virus filter at 50% flow decay for fluids having a pH of 5.5, 6.5, or 7.5. These data show that fluids having a pH of 5.5 have better throughput through a virus filter as compared to fluids having a pH of 6.5 or pH 7.5, with fluids having a pH of 6.5 having the lowest throughput through the virus filter.

FIG. 8 shows the relationship of the virus filter throughput at 50% flow decay to the concentration of stabilizing agent in the fluid. These data show that generally the virus filter throughput increases as the concentration of stabilizing agent in the fluid increases. The data in FIGS. 9 and 10 show that there is no significant relationship of the virus filter throughput at 50% flow decay to the concentration of sodium chloride or the percentage of protein aggregates in the fluid, respectively. The data in FIG. 11 show that, as the average particle concentration of the fluid increases, the throughput of the virus filter at 50% flow decay decreases.

FIG. 12 shows the effect of the concentration of sodium chloride at pH 5.5, 6.5, or 7.6 on the throughput of the virus filter at 50% flow decay. These data show that increasing sodium chloride concentrations from 50 mM to 300 mM increase the virus filter throughput at pH 5.5, while increasing sodium chloride concentrations from 50 mM to 300 mM decreases the virus filter throughput at pH 7.6.

FIG. 13 shows the effect of the concentration of sodium chloride at pH 5.5, 6.5, or 7.6 on the percentage of protein aggregates. The data show that increasing sodium chloride concentrations at pH 5.5 results in an increase in the percentage of protein aggregates, while increasing sodium chloride concentrations at pH 7.6 results in a decrease in the percentage of protein aggregates.

FIG. 14 shows the effect of the concentration of sodium chloride, the pH of the fluid, and the type of pre-filter used (0.1 µm pre-filter or Sartorius Virosart® Max pre-filter) on the virus filter throughput at 50% flow decay. These data show that fluids pre-filtered with a Sartorius Virosart® Max pre-filter have higher virus throughput values as compared to fluids pre-filtered with a 0.1 µm pre-filter. For fluids pre-filtered using a Sartorius Virosart® Max pre-filter, increases in sodium chloride concentration correlated with increased virus filter throughput at pH 5.5, while increases in sodium chloride concentration correlated with decreased virus filter throughput at pH 7.6.

The data in FIG. 15 show that at pH 5.5, increasing concentrations of sodium chloride in the fluid correlate with a decrease in the hydrodynamic radius of the BNJ441 monoclonal antibody, while at pH 7.6, increasing concentrations of sodium chloride in the fluid only modestly correlate with a decrease in the hydrodynamic radius of the BNJ441 monoclonal antibody.

The data in FIG. 16 show that the hydrodynamic radius of the BNJ441 monoclonal antibody generally increases with the increasing pH of the fluid. The data in FIG. 17 show the relationship between the percentage of aggregates in the fluids with the sodium chloride concentrations in the fluids.

FIG. 18 shows the optimal concentrations of L-arginine that should be included in a fluid including BNJ441 monoclonal antibody to achieve a virus filter flow rate of greater than 750 g/m$^2$ (the non-shaded area in the graph).

These data show indicate that for fluids including an antibody having at least one histidine in a CDR of the light or heavy chain (such as the BNJ441 monoclonal antibody), that a pH of between about 5.0 and about 6.7 improves the virus filter throughput, and optionally, that adjusting (e.g., increasing or decreasing) the fluid to a stabilizing agent concentration of between about 0 mM and about 25 mM can further increase virus filter throughput. The data also indicate that for fluids including an antibody having at least one histidine in a CDR of the light or heavy chain (such as the BNJ441 monoclonal antibody) and having a pH of between about 6.7 and about 8.5, that adjusting the stabilizing agent concentration of the fluid to between about 10 mM and about 100 mM will improve the virus filter throughput. In addition, for all fluids, the data show that the use of a Sartorius Virosart® Max pre-filter improves the virus filter throughput.

Example 2. Effect of pH on Viral Filtration of BNJ441 Monoclonal Antibody

A set of experiments were performed to test the effect of the pH of a fluid including 4 mg/mL BNJ441 monoclonal antibody on viral filtration performed using an Asahi Planova BioEx or an Asahi 20N viral filter. Each tested fluid contained 65 mM sodium chloride and had a pH of between 7 and 8.5 (see, Table 1 below).

TABLE 1

Tested Fluids including BNJ441 Monoclonal Antibody

| Filter | pH | Salt Concentration (mM) | Product Concentration (mg/mL) |
| --- | --- | --- | --- |
| Bio EX | 7 | 65 | 4 |
| Bio EX | 7.75 | 65 | 4 |
| Bio EX | 8.5 | 65 | 4 |
| 20N | 7.75 | 65 | 4 |

The data in FIGS. 19-22 show that the best flux to throughput was achieved when a fluid having a pH of 7.75 and containing 65 mM sodium chloride and 4 mg/mL BNJ441 monoclonal antibody was flowed through an Asahi 20N viral filter.

Example 3. Statistical Analysis to Determine Factors Important for Viral Filtration of Samalizumab Statistical analyses were performed to determine what parameters (factors) were most important for throughput of samalizumab through a Sartorius Virosart® CPV virus filter. The fluids tested in these experiments included between 5 mg/mL to 15 mg/mL of samalizumab and between 75 mM to 300 mM sodium chloride, and had a pH of between 5 and 6. The fluids tested in this experiment are listed in Table 2.

TABLE 2

Tested Fluids including Samalizumab

| pH | Salt Concentration (mM) | Product Concentration (mg/mL) |
| --- | --- | --- |
| 5 | 75 | 5 |
| 5 | 75 | 15 |
| 5 | 300 | 5 |
| 5 | 300 | 15 |
| 5.5 | 190 | 10 |
| 6 | 75 | 5 |
| 6 | 75 | 15 |
| 6 | 300 | 5 |
| 6 | 300 | 15 |

The relationship between the percentage flux decay and the throughput of the Virosart® CPV virus filter when each fluid was flowed through the Virosart® CPV virus filter is shown in FIG. 23. Statistical analyses was performed to test the relationship of the pH of each fluid, the sodium chloride concentration of each fluid, and the samalizumab concentration of each fluid on the virus filter throughput (FIG. 24). The statistical analyses show that virus filter throughput increases as pH is increases between pH 5 and pH 6, that virus filter throughput increases as the sodium concentration increases between 75 mM and 300 mM, and that virus filter throughput decreases as the samalizumab concentration increases between 5 mg/mL and 15 mg/mL.

Example 4. Statistical Analyses to Determine Factors Important for Viral Filtration of BNJ383 Monoclonal Antibody Statistical analyses were performed to determine what parameters (factors) were most important for throughput of BNJ383 monoclonal antibody through a Sartorius Virosart® CPV virus filter or a Virosart HF virus filter. The fluids tested in these experiments included 10 mg/mL of BNJ383 monoclonal antibody and between 80 mM to 300 mM sodium chloride, and had a pH of between 7 and 8.5. The fluids tested in this experiment are listed in Table 3.

TABLE 3

Tested Fluids including BNJ383 Monoclonal Antibody

| Viral Filter Type | pH | Salt Concentration (mM) | Product Concentration (mg/mL) |
| --- | --- | --- | --- |
| HF | 7 | 80 | 10 |
| HF | 8.5 | 80 | 10 |
| HF | 7.75 | 190 | 10 |
| HF | 7 | 300 | 10 |
| HF | 8.5 | 300 | 10 |
| CPV | 7.75 | 80 | 10 |

The data show that the best flux decay as compared to throughput is achieved when a fluid including 10 mg/mL BNJ383 monoclonal antibody and 80 mM sodium chloride, and having a pH of 7 was flowed through a Virosart HF virus filter (FIG. 25). Statistical analyses of the data for each fluid show that virus filter throughput decreases as pH in the fluid increases between 7 and 8.5, and that virus filter throughput decreases a sodium chloride concentration increases between 80 mM to 300 mM (FIG. 26).

Example 5. Effect of Different Pre-Filters on Viral Filtration of Eculizumab A set of experiments was performed to test the effect of pre-filtration using a number of different pre-filters on downstream viral filtration of a fluid including 7.1 mg/mL eculizumab and 80 mM sodium chloride, and having a pH of 6.5, using a Virosart® CPV viral filter. The different pre-filters tested were: a Millipore 0.5/0.2 µm and 0.5/0.1 µm pre-filter, a Sartorius Virosart® Max pre-filter, a Sartopore 2 pre-filter, Sartobind STIC pre-filter, Sartobind Q pre-filter, Sartobind HIC Phenyl pre-filter, or a Sartobind S pre-filter.

The data show that the best flux decay as compared to throughput of the virus filter occurred when a fluid including 7.1 mg/mL eculizumab and 80 mM sodium chloride, and having a pH of 6.5 was flowed through a Sartorius Virosart® Max pre-filter prior to flowing the fluid through a Virosart® CPV virus filter (FIG. 27). The data also show that passing a fluid including 7.1 mg/mL eculizumab and 80 mM sodium chloride, and having a pH of 6.5 through a Sartorius Virosart® Max pre-filter also significantly reduced the percentage of soluble protein aggregates in fluid before it is flowed into the Virosart® CPV virus filter (FIG. 28). The data also show that flowing a fluid including XX mg/mL eculizumab and 80 mM sodium chloride, and having a pH of 6.5 through a Sartorius Virosart® Max pre-filter also reduces the insoluble particle concentration in the fluid (compare the data for Q1 Pool to the data for Sartorius Virosart® Max Pool) (FIG. 29).

These data show that flowing a fluid including eculizumab through a pre-filter (e.g., a pre-filtering including a polyamide membrane, such as Sartorius Virosart® Max pre-filter) reduces the concentration of soluble protein aggregates and insoluble particles in the fluid, and increases the throughput of viral filtration (as the fluid is subsequently flowed through a virus filter, such as a Virosart® CPV virus filter).

Example 6. Study of Virosart® CPV Virus Filter Lot-to-Lot Variability

A set of experiments was performed to evaluate the lot-to-lot variability of the Virosart® CPV virus filter on the throughput of eculizumab. In these experiments, three different lots of the 5 cm² Virosart® CPV virus filter were tested using the same loading material.

Materials and Methods

The starting material for these experiments was prepared by performing the following steps: capturing eculizumab from a concentrated clarified culture medium using Protein A chromatography, performing low pH viral inactivation, performing ultrafiltration and diafiltration, and performing Q Sepharose chromatography. The starting material was then flowed through a pre-filter in each experiment, (i.e., immediately before being flowed through a Virosart® CPV virus filter).

In the experiments, 218 mL of the starting material was filtered across a 3.5 cm² Millipore 0.5/0.2 µm pre-filter (SHC), and a 0.5 µm/0.1 µm pre-filter (SHR). One hundred mL of the resulting filtrate was filtered across a 5 cm² Virosart® CPV virus filter to determine the filter throughput of eculizumab in 20 mM sodium phosphate, 80 mM sodium chloride, pH 6.50. The remaining 100 mL was processed over another lot of Virosart® CPV virus filter until the flux declined to ~0% of the initial value (FIG. 30). The process was performed two additional times to evaluate three different lots of Virosart® CPV virus filters in duplicate. Table 4 lists the processing conditions for the virus filter testing. The virus filter flux, flux decay, and feed pressure were monitored. The starting material and the viral filtrate were assessed for protein concentration using absorbance at 280 nm, and level of soluble protein aggregates.

TABLE 4

Process Conditions for Testing Lot-to-Lot Variability in Viral Filters

| Parameter | Experimental Condition |
|---|---|
| Equilibration buffer | 20 mM sodium phosphate, 80 mM sodium chloride, pH 6.50 |
| Pre-Filters area | 3.5 cm² |
| CPV Filter Area | 5 cm² |
| Pre-Filter Load (L/m²) | 623 (218 mL) |
| Virus filter load (L/m²) | 200 |
| Load volume | 100 mL |
| Feed pressure (psi) | 27-33 |
| Buffer Chase | 12.5 mL |

Results

The data in FIGS. 31 and 32 show that there is significant lot-to-lot variability in the flux of Virosart® CPV virus filters, and also significant variability in Virosart® CPV virus filters from the same lot.

Example 7. Study of Effect of Pre-Filtering Loading Parameters on the Throughput of Downstream Virus Filter A set of experiments was performed to test the effect of pre-filter loading parameters on the throughput of a downstream Virosart® CPV virus filter.

Materials and Methods

The starting material for these experiments was prepared by performing the following steps: capturing eculizumab from a concentrated clarified culture medium using Protein A chromatography, performing low pH viral inactivation, performing ultrafiltration and diafiltration, and performing Q Sepharose chromatography. The starting material was pre-filtered using a 3.5 cm² Millipore 0.5/0.2 µm pre-filter (SHC), and a 3.5 cm² 0.5 µm/0.1 µm pre-filter (SHR) under two different conditions: 622 L/m² (218 mL flowed through the 3.5 cm² SHC and 3.5 cm² SHR) or 311 L/m² (109 mL through the 3.5 cm² SHC and 3.5 cm² SHR), and then 100 mL of each filtrate (including 20 mM sodium phosphate, 80 mM sodium chloride, pH of 6.5) was passed through a 5 cm² Virosart® CPV virus filter at 200 L/m², with a feed pressure of 27-33 psi, and a buffer chase of 12.5 mL. Each experiment was performed in duplicate. The flux over time of the Virosart® CPV virus filter was measured.

Results

The data in FIGS. 33 and 34 show that there was no significant difference in the throughput of the Virosart® CPV virus filters when pre-filters were loaded at 311 L/m² or 622 L/m².

Example 8. Study of Effect of Feed Pressure on Throughput of Virus Filters

A set of experiments was performed to determine the effect of feed pressure on throughput of Virosart® CPV virus filters.

Materials and Methods

The starting material for these experiments was prepared by performing the following steps: capturing eculizumab from a concentrated clarified culture medium using Protein A chromatography, performing low pH viral inactivation, performing ultrafiltration and diafiltration, and performing Q Sepharose chromatography. The starting material was filtered using a 3.5 cm$^2$ Millipore 0.5/0.2 µm pre-filter (SHC), and a 3.5 cm$^2$ 0.5 µm/0.1 µm pre-filter (SHR), or a Sartorius Virosart® Max pre-filter (5 cm$^2$) to yield a including 20 mM sodium phosphate, 80 mM sodium chloride, pH of 6.5, which was then further filtered in-line with a 5 cm$^2$ Virosart® CPV virus filter, with a feed pressure of 15 psi or 30 psi for SHC/SHR pre-filter runs and 30 psi for the Virosart Max Pre-filter run. Each experiment was performed in duplicate. The flux over time of the Virosart® CPV virus filter was measured.

Results

The data in FIGS. 35 and 36 show that there is no significant difference in the throughput of the Virosart® CPV virus filter when it is loaded using different inlet pressures, and that there is a significant improvement in Virosart® CPV virus filter throughput when a Sartorius Virosart® Max pre-filter is used prior to the Virosart® CPV virus filter. The viral filtration operation time was significantly reduced with the Virosart® Max pre-filter.

Example 8. Effect of Protein Concentration During Pre-Filtration on Throughput of Downstream Viral Filter A set of experiments was performed to test the effect of protein concentration during pre-filtration on the throughput of an immediately downstream Virosart® CPV virus filter.

Materials and Methods

The starting material for these experiments was prepared by performing the following steps: capturing eculizumab from a concentrated clarified culture medium using Protein A chromatography, performing low pH viral inactivation, performing ultrafiltration and diafiltration, and performing Q Sepharose chromatography. The starting material (218 mL) having concentration of eculizumab of 4 mg/mL or 8 mg/mL was loaded at 623 L/m$^2$ onto a 3.5 cm$^2$ Millipore 0.5/0.2 µm pre-filter (SHC), and a 3.5 cm$^2$ 0.5 µm/0.1 µm pre-filter (SHR), or a Sartorius Virosart® Max pre-filter (5 cm$^2$), and then 100 mL of each filtrate (including 20 mM sodium phosphate, 80 mM sodium chloride, pH of 6.5) was passed through a 5 cm$^2$ Virosart® CPV virus filter at 200 L/m$^2$, with a feed pressure of 27-33 psi, and a buffer chase of 12.5 mL. The flux over time of the Virosart® CPV virus filter was measured.

Results

The data in FIGS. 37 and 38 show that a significant increase in the volumetric throughput of the Virosart® CPV virus filter occurs when the pre-filter is loaded with a lower concentration of eculizumab, and that there is a significant improvement in Virosart® CPV virus filter throughput when a Sartorius Virosart® Max pre-filter is used prior to the Virosart® CPV virus filter.

Example 9. Purification of Eculizumab Using Pre-Filtration Prior to Viral Filtration A set of experiments was performed to test the effect of different pre-filters on a process for purifying eculizumab that includes the use of a pre-filter immediately prior to viral filtration.

Materials and Methods

The starting material for these experiments was prepared by performing the following steps: capturing eculizumab from a concentrated clarified culture medium using Protein A chromatography, performing low pH viral inactivation, performing ultrafiltration and diafiltration, and performing Q Sepharose chromatography. The starting material was loaded with a pressure of 30 psi and at 623 L/m$^2$ onto a 3.5 cm$^2$ Millipore 0.5/0.2 µm pre-filter (SHC), and a 3.5 cm$^2$ 0.5 µm/0.1 µm pre-filter (SHR), or a Sartorius Virosart® Max pre-filter (5 cm$^2$), and each filtrate (including 20 mM sodium phosphate, 80 mM sodium chloride, pH of 6.5) was then passed through a 5 cm$^2$ Virosart® CPV virus filter at 200 L/m$^2$, with a feed pressure of 30 psi, and 25 mL of a chase buffer was flowed through the Virosart® CPV virus filter 60 minutes after the last of the pre-filter eluate has been flowed through the Virosart® CPV virus filter. During filtration with the Virosart® CPV virus filter, if an 80% flux decay was reached, the filtration was paused for 60 minutes and the pre-filter eluate loaded onto the Virosart® CPV virus filter was diluted 4-fold in buffer. The flux over time of the Virosart® CPV virus filter was measured.

Results

The data in FIGS. 39 and 40 show that an improved throughput of the Virosart® CPV virus filter was achieved when a Sartorius Virosart® Max pre-filter was used prior to the Virosart® CPV virus filter, and that the pause and dilution used when a 80% flux decay was reached, was not necessary when a Sartorius Virosart® Max pre-filter was used prior to the Virosart® CPV virus filter. In contrast, in one of the two experiments where a 3.5 cm$^2$ Millipore 0.5/0.2 µm pre-filter (SHC), and a 3.5 cm$^2$ 0.5 µm/0.1 µm pre-filter (SHR) was used as a pre-filter, an 80% flux decay was reached, and it was necessary to use the 60 minute pause and four-fold dilution (FIGS. 39 and 40; Run 1—SHC/SHR).

Example 10. Use of Depth Filtration Between Different Steps of an Eculizumab Purification Process A set of experiments was performed to test the effect of performing depth filtration between different steps of a recombinant protein purification process.

Materials and Methods

A depth filtration step was inserted between different steps of starting recombinant protein purification process. The starting recombinant protein purification process uses the steps of preparing a clarified culture medium, concentrating the recombinant protein using ultrafiltration/diafiltration, solvent/detergent viral inactivation, capturing the recombinant protein using protein A chromatography (capture), polishing the recombinant protein, performing ultrafiltration/diafiltration, performing viral filtration, performing final polishing of the recombinant protein, and performing ultrafiltration/diafiltration (shown in FIG. 41A). A depth filtration step that includes flowing a fluid including the recombinant protein through a CUNO Delipid filter was performed between two different steps in the starting recombinant protein purification process (see, FIGS. 41B to 41D). The impact of performing the depth filtration step in each tested process was determined by detecting the flux in a downstream Virosart® CPV virus filter and detecting the level of soluble protein aggregates and insoluble protein particles in the final purified recombinant protein at the end of the tested purification process.

In a second set of experiments, three different depth filters were tested for their ability to reduce host cell protein levels. One of the three tested filters was a depth filter having anionic and hydrophobic properties (Filter 2, which is a CUNO Delipid filter). Alexion 1210 (also called BNJ441) was purified using an eculizumab purification process as shown in FIG. 41D, where the depth filter was the depth filter having anionic and hydrophobic properties (Filter 2), and where the depth filtration step was performed using original conditions or under conditions optimized to maximize impurity removal while maintaining greater than 85% yield of eculizumab. The depth filter having anionic and hydrophobic properties (Filter 2) was also tested to determine if the level of Murine Minute Virus (MMV) and Xenotrophic Murine Leukemia Virus (XMuLV) in a fluid could be reduced by flowing the fluid through the depth filter.

Results

The data in FIGS. 42 and 43 show that a significant improvement in aggregate removal and particulate content was observed when depth filtration was performed immediately prior to virus filtration. The data in FIGS. 44A and 44B show that a depth filter having anionic and hydrophobic properties results in significant removal of host cell protein and soluble protein aggregates (Filter 2). The data in Table 5 show the result of performing depth filtration using a depth filter having anionic and hydrophobic properties on the level of MMV and XMuLV.

TABLE 5

Viral Clearance Results for Adsorptive Depth Filtration

| Virus | $Log_{10}$ Reduction |
| --- | --- |
| MVM | 0.72 ± 0.33 |
| X-MuLV | 1.46 ± 0.20 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of performing viral filtration, the method comprising the steps of:
   (a) adjusting the pH of a fluid comprising a recombinant antibody to between about 5.0 and about 6.7, and adding a stabilizing agent to the fluid in an amount sufficient to yield a final concentration of between about 0.1 mM and about 25 mM stabilizing agent in the fluid;
   (b) flowing the fluid through a pre-filter, wherein the pre-filter comprises a polyamide membrane; and
   (c) immediately following step (b), flowing the fluid through a virus filter to produce a filtrate comprising the recombinant antibody,
   wherein:
   (i) the stabilizing agent is selected from the group consisting of arginine, alanine, aspartic acid, glutamic acid, leucine, lysine, histidine, glycine, sucrose, trehalose, mannitol, and sorbitol; and
   (ii) (ii) the recombinant antibody comprises:
      a heavy chain variable region comprising:
         a CDR1 comprising a sequence of SEQ ID NO: 1;
         a CDR2 comprising a sequence of SEQ ID NO: 2; and
         a CDR3 comprising a sequence of SEQ ID NO: 3; and
      a light chain variable region comprising
         a CDR1 comprising a sequence of SEQ ID NO: 6;
         a CDR2 comprising a sequence of SEQ ID NO: 7; and
         a CDR3 comprising a sequence of SEQ ID NO: 8.

2. The method of claim 1, wherein the fluid further comprises between about 5 mM and about 300 mM sodium chloride.

3. The method of claim 1, wherein the virus filter comprises a polyethersulfone membrane.

4. The method of claim 1, wherein the virus filter comprises a polyvinylidene fluoride (PVDF) membrane.

5. The method of claim 1, wherein the virus filter comprises a cuprammonium-regenerated cellulose membrane.

6. The method of claim 1, wherein prior to (a), the pH of the fluid is between about 7.4 and about 7.8.

7. The method of claim 1, wherein the heavy chain variable domain comprises a sequence of SEQ ID NO: 4.

8. The method of claim 1, wherein the recombinant antibody comprises a heavy chain comprising a sequence of SEQ ID NO: 5.

9. The method of claim 1, wherein the recombinant antibody comprises a light chain variable region comprising a sequence of SEQ ID NO: 9.

10. The method of claim 1, wherein the recombinant antibody comprises a light chain comprising a sequence of SEQ ID NO: 10.

11. The method of claim 1, wherein the recombinant antibody comprises a heavy chain variable domain comprises a sequence of SEQ ID NO: 4 and a light chain variable region comprising a sequence of SEQ ID NO: 9.

12. The method of claim 1, wherein the recombinant antibody comprises a heavy chain comprising a sequence of SEQ ID NO: 5 and a light chain comprising a sequence of SEQ ID NO: 10.

13. A method of performing viral filtration, the method comprising the steps of:
   (a) adjusting the pH of a fluid comprising a recombinant antibody to between about 5.0 and about 6.7, and adding a stabilizing agent to the fluid in an amount sufficient to yield a final concentration of between about 0.1 mM and about 25 mM stabilizing agent in the fluid;
   (b) performing ultrafiltration/diafiltration on the fluid;
   (c) following step (b), flowing the fluid through a pre-filter, wherein the pre-filter comprises a polyamide membrane; and
   (d) immediately following step (c), flowing the fluid through a virus filter to produce a filtrate comprising the recombinant antibody,
   wherein:
   (i) the stabilizing agent is selected from the group consisting of arginine, alanine, aspartic
   acid, glutamic acid, leucine, lysine, histidine, glycine, sucrose, trehalose, mannitol, and sorbitol;
   (ii) the recombinant antibody comprises: a heavy chain variable region comprising: the CDR1 comprising a sequence of SEQ ID NO: 1, the CDR2 comprising a sequence of SEQ ID NO: 2, and the CDR3 comprising a sequence of SEQ ID NO: 3, and a light chain variable region comprising: a CDR1 comprising a sequence of SEQ ID NO: 6, a CDR2 comprising a sequence of SEQ ID NO: 7, and a CDR3 comprising a sequence of SEQ ID NO: 8.

* * * * *